US012662676B2

(12) United States Patent
Yang et al.

(10) Patent No.: US 12,662,676 B2
(45) Date of Patent: Jun. 23, 2026

(54) APTAMER NUCLEIC ACID MOLECULE, AND COMPLEX AND APPLICATION THEREOF

(71) Applicant: EAST CHINA UNIVERSITY OF SCIENCE AND TECHNOLOGY, Shanghai (CN)

(72) Inventors: Yi Yang, Shanghai (CN); Linyong Zhu, Shanghai (CN); Xianjun Chen, Shanghai (CN); Dasheng Zhang, Shanghai (CN); Ni Su, Shanghai (CN); Qiuning Lin, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 199 days.

(21) Appl. No.: 17/607,102

(22) PCT Filed: Apr. 28, 2020

(86) PCT No.: PCT/CN2020/087415

§ 371 (c)(1),
(2) Date: Oct. 28, 2021

(87) PCT Pub. No.: WO2020/221238

PCT Pub. Date: Nov. 5, 2020

(65) Prior Publication Data

US 2023/0002769 A1 Jan. 5, 2023

(30) Foreign Application Priority Data

Apr. 28, 2019 (CN) ......................... 201910348701.7

(51) Int. Cl.

| | |
|---|---|
| ***C12N 15/115*** | (2010.01) |
| ***C07C 255/53*** | (2006.01) |
| ***C07C 255/58*** | (2006.01) |
| ***C07D 213/74*** | (2006.01) |
| ***C07D 213/85*** | (2006.01) |
| ***C07D 239/42*** | (2006.01) |
| ***C07D 241/20*** | (2006.01) |
| ***C07D 241/24*** | (2006.01) |
| ***C07D 263/56*** | (2006.01) |
| ***C07D 277/64*** | (2006.01) |
| ***C07D 333/60*** | (2006.01) |
| ***C07D 495/04*** | (2006.01) |
| ***C09K 11/06*** | (2006.01) |
| ***C12N 15/10*** | (2006.01) |
| ***C12Q 1/6876*** | (2018.01) |

(52) U.S. Cl.

CPC .......... *C12N 15/115* (2013.01); *C07C 255/53* (2013.01); *C07C 255/58* (2013.01); *C07D 213/74* (2013.01); *C07D 213/85* (2013.01); *C07D 239/42* (2013.01); *C07D 241/20* (2013.01); *C07D 241/24* (2013.01); *C07D 263/56* (2013.01); *C07D 277/64* (2013.01); *C07D 333/60* (2013.01); *C07D 495/04* (2013.01); *C09K 11/06* (2013.01); *C12N 15/1003* (2013.01); *C12Q 1/6876* (2013.01); *C09K 2211/1007* (2013.01); *C09K 2211/1018* (2013.01); *C12N 2310/16* (2013.01); *C12N 2310/351* (2013.01); *C12N 2320/10* (2013.01)

(58) Field of Classification Search

None

See application file for complete search history.

(56) References Cited

U.S. PATENT DOCUMENTS 11,629,131 B2 4/2023 Jaffrey et al.

FOREIGN PATENT DOCUMENTS

| | | | |
|---|---|---|---|
| CN | 1764729 | A | 4/2006 |
| CN | 102171234 | A | 8/2011 |
| CN | 102405212 | A | 4/2012 |
| CN | 103710030 | A | 4/2014 |
| JP | 2007043917 | A | 2/2007 |

OTHER PUBLICATIONS

Journal of the American Chemical Society, year2014, Vo1.136, pp. 16299-16308.

Science, year2011, vol. 333, pp. 642-646.

Nat Chem Biol. Author manuscript, year2017 , vol. 13, No. 11, pp. 1187-1194 (27 pages).

Nature Biotechnology, Sep. 23, 2019, vol. 37, pp. 1287-1293.

Visualizing RNA dynamics in live cells with bright and stable fluorescent RNAs Xianjun Chen et al. Nature Biotechnology, vol. 37 No. 11, Sep. 23, 2019.

Programmable RNA detection with a fluorescent RNA aptamer using optimized three-way junction formation Yuichi Furuhata et. al. RNA, vol. 25 No. 5, Feb. 11, 2019.

A Fluorescent Split Aptamer for Visualizing RNA-RNA Assembly In Vivo Khalid K. Alam et al. ACS Synth. Biol. vol. 6, No. 9, May 26, 2017.

(Continued)

*Primary Examiner* — Ekaterina Poliakova-Georgantas

(74) *Attorney, Agent, or Firm* — Rivka Friedman

(57) ABSTRACT

The present application relates to an aptamer nucleic acid molecule, a complex containing the aptamer nucleic acid molecules, a method of detecting intracellular or extracellular RNA, DNA or other target molecules, and a kit containing the aptamer. The aptamer of the present application is capable of specifically binding a kind of fluorophore micromolecules, and can significantly enhance fluorescence intensity under excitation light of appropriate wavelength.

1 Claim, 7 Drawing Sheets

Specification includes a Sequence Listing.

(56) References Cited

OTHER PUBLICATIONS

Aixiang Ding, ?The Applications of Amine α-Cyanostilbene-modified Derivatives in Fluorescence Liquid Crystals and Environmental Sensing§, Sep. 15, 2014.
Imaging dynamics of endogenous mitochondrial RNA in single living cells Ozawa et al. Nature Methods 2007. 4 413-419.
Dual-colour imaging of RNAs using quencher- and fluorophore-binding aptamers Arora et al. Nucleic Acids Research 2015. 21 e144.
RNA Mimics of Green Fluorescent Protein Paige et al. Science 2011. 333 642-646.
A superfolding Spinach2 reveals the dynamic nature of trinucleotide repeat-containing RNRNA Strack et al. Nature Methods 2013. 10 1219-1224.
Fluorescence Imaging of Cellular Metabolites with RNA Paige et al. Science 2012. 335 1194.
Understanding the Photophysics of the Spinach-DFHBI RNA Han et al. Journal of the American Chemical Society 2013.
Plug- and-Play Fluorophores Extend the Spectral Properties of Spinach Song et al. Journal of the American Chemical Society 2014.
Broccoli Rapid Selection of an RNA Mimic of Green Fluorescent Protein by Fluorescence-Based Selection and Directed Evolution Filonov et al. Journal of the American Chemical Society 2014.
Imaging RNA polymerase III transcription using a photostable RNA-fluorophore complex Song et al.Nature chemical biology 2017.
Saskia Neubacher et al: “RNA Structure and Cellular Applications of Fluorescent Light-Up Aptamers”, Angewandte Chemie International Edition, vol. 58, No. 5, Nov. 5, 2018 (Nov. 5, 2018), pp. 1266-1279, XP055741164, ISSN: 1433-7851, DOI: 10.1002/anie.201806482, the whole document.
Robert J. Trachman et al: “Structural Principles of Fluorescent RNA Aptamers”, Trends in Pharmacological Sciences., vol. 38, No. 10, Oct. 1, 2017 (Oct. 1, 2017), pp. 928-939, XP055486696, GB ISSN: 0165-6147, DOI: 10.1016/j.tips.2017.06.007, the whole document.

A B

APTAMER NUCLEIC ACID MOLECULE, AND COMPLEX AND APPLICATION THEREOF

FIELD OF THE INVENTION

The present application relates to an aptamer nucleic acid molecule, a complex containing the aptamer nucleic acid molecules, a method of detecting intracellular or extracellular RNA, DNA or other target molecules, and a kit containing the aptamer. The aptamer of the present application is capable of specifically binding a kind of fluorophore micromolecules, and can significantly enhance fluorescence intensity under excitation light of appropriate wavelength.

BACKGROUND OF THE INVENTION

Among all biomacromolecules, RNA exhibits the most diverse biological functions. In the Central Dogma of biology, RNA serves as the transmitter of genetic material (messenger RNA), template for protein synthesis (ribosomal RNA), and amino acid transporter (transfer RNA), constitutes a series of physiological processes, and finally realizes gene transcription and expression. In the past few decades, scientists have gradually discovered the crucial functions of RNA in a variety of vital activities, including many RNA-protein complexes, such as telomerase, splicing enzyme, ribozyme, and riboswitch or the like. In addition, some non-coding RNAs, such as short interfering RNA (siRNA), microRNA (microRNA), and long non-coding RNA (lncRNA), have played an irreplaceable role in the regulation of gene expression at the post-transcriptional level for the past few years. Real-time monitoring of RNA transport and metabolic processes in cells is critical for studying the relationship between RNA localization and gene expression, as well as cell regulation. At present, scientists have identified several mechanisms that can lead to different subcellular localizations of RNA, such as active transport, passive diffusion, and anchoring and so on. In many polar cells, especially nerve cells, the spatial specific expression of mRNA is closely related to the plasticity, learning and memory of neurons. Therefore, once these regulation processes of RNA are damaged, it will cause neuronal dysfunction and neurological diseases.

RNA fluorescence in situ hybridization technology is a method that has been widely used for a long time in the study of the level and distribution of RNA in cells, and uses molecular hybridization in the fluorescent labeling and imaging of specific RNA molecules. However, its operation is relatively complicated and contains an elution step, so it can only be used for the study of immobilized cells, i.e. dead cells, rather than for real-time monitoring of the dynamic changes of RNA in living cells. Molecular Beacon is the first developed RNA imaging technology of living cells. It is a stem-loop double-labeled oligonucleotide probe using an auto hairpin structure formed at the 5' and 3' ends, and, when it binds to the target RNA, the quenching effect of a quenched group labeled at one end on the fluorescence group is eliminated and the fluorescent group produces fluorescence, or the FRET of the fluorescent groups at both ends disappears. However, Molecular Beacons have disadvantages such as low fluorescence signals, difficulty in entering cells, being easily degradable, serious non-specific aggregation in the nucleus, being susceptible to RNA secondary structure and a custom oligonucleotide probes being needed for each RNA, etc., and these shortcomings limit the wide application of this technology.

The current methods of RNA imaging for living cells mainly use the MCP-FPs system, which can specifically recognize mRNA molecules fused with multiple-copies of MS2 sequences, and monitor mRNA synthesis and distribution in real time by detecting fluorescent protein signals (Ozawa et al., Nature Methods, 2007. 4: 413-419). However, due to the high background fluorescence generated by MCP-FPs not bound to mRNA molecules, the signal-to-noise ratio of this method is very low. Then, scientists added nuclear localization signals to MCP-FPs fusion protein so that GFP-MS2 not bound to mRNA molecules were localized in the nucleus, thereby reducing the non-specific fluorescence in cytoplasm to a certain extent and increasing the signal-to-noise ratio of the detection.

In addition to cellular RNA detection by means of the RNA-binding protein-fluorescent protein technology, scientists have been looking for RNA fluorescent label, which is similar to GFP, for RNA imaging. Scientists constructed a fluorophore-quencher combination, wherein the quencher cannot quench the fluorescent signal of the fluorophore when the fluorophore aptamer (Aptamer) binds to the fluorophore, and the complex formed of aptamer-fluorophore-quencher is fluorescent at this moment. When the aptamer of the fluorophore is not present, the fluorescence signal of the fluorophore will be quenched by the quencher. Based on this principle, scientists have realized the imaging of mRNA in bacteria (Arora et al., Nucleic Acids Research, 2015. 21: e144). In addition, a label named IMAGE (intracellular multi aptamer genetic) has also been developed, which is formed of two different aptamer-micromolecule complexes. When the micromolecules bind to the aptamer in RNA sequence, the fluorophore carried by two adjacent micromolecules will undergo fluorescence resonance energy transfer (FRET), and RNA in cells can be detected by the detection of changes in the fluorescence signal. However, neither of these two methods has achieved real-time monitoring of RNA in mammalian cells. In 2011, S. Jaffrey's research group obtained a nucleic acid aptamer called "Spinach", which can specifically bind to a fluorophore (3,5-difluoro-4-hydroxybenzyli-dene imidazolinone, DFHBI) and thus significantly increases its fluorescence (Paige et al., Science, 2011. 333: 642-646; Strack et al., Nature Methods, 2013. 10: 1219-1224). "Spinach2", which is a "Spinach" mutant, is more stable and provides an excellent tool for labeling RNA in living cells by means of genetic coding. The research group replaced a stem-loop structure in "Spinach" with a nucleic acid aptamer which can specifically bind to cell metabolites, and developed a tool that can detect cell metabolites based on Spinach-DFHBI complex (Paige et al., Science, 2012. 335: 1194). So far, this method has been successfully used to monitor and analyze the dynamic changes of RNA in bacteria, yeast and mammalian cells. Subsequently, the research group also developed a Corn-DFHO complex for the activity detection of RNA polymerase III promoter in mammalian cells (Song et al., Nature Chemical Biology, 2017. 13: 1187-1194). However, the wide application of this method has been greatly limited by the following shortcomings: (1) the binding ability of the aptamer-fluorophore complex is weak with a dissociation constant (kd) of tens to hundreds nM; (2) the fluorescence signal of the aptamer-fluorophore complex is unstable and can be easily quenched, making its fluorescence signal undetectable (Han et al., Journal of the American Chemical Society, 2013. 135: 19033-19038); (3) so far, the spectrum is only green and yellow, lacking longer wavelengths for the imaging of RNA in living animals (Song et al., Journal of the American Chemical Society, 2014. 136: 1198-1201); (4)

Corn is a dimer, which may interfere with the functions of target RNA; (5) currently, there are no other aptamer-fluorophore complexes capable of simultaneously monitoring multiple RNAs in cells.

To sum up, the currently used RNA labeling technologies have their own obvious shortcomings. MCP-FPs labeling technology has strong unbound background fluorescence and low signal-to-noise ratio. The RNA labeling technology based on the complex formed of aptamer-fluorophore-quencher currently realizes the labeling of RNA only in bacteria, and has not yet realized the labeling of RNA in mammalian cells. RNA labeling technology based on single fluorophore-nucleic acid aptamer seems to be a perfect RNA labeling technology, but it has not been widely used due to the non-ideal nature of the complex formed by the current fluorophore (DFHBI, DFHBI-1T, DFHO) and nucleic acid aptamer. Therefore, more effective fluorophore-nucleic acid aptamer complexes, which can overcome the shortcomings of the previous fluorophore-nucleic acid aptamer complexes in real-time labeling of RNA or DNA in living cells, have always been needed in the scientific and industrial communities.

SUMMARY

The present application provides a nucleic acid aptamer molecule, a DNA molecule encoding the nucleic acid aptamer molecule, a complex of nucleic acid aptamer molecules and fluorophore molecules, and uses of the complex.

The technical solutions provided by the present application are as follows.

The present application provides a nucleic acid aptamer molecule containing following nucleotide sequences (a), (b) or (c):

- (a): a nucleotide sequence $N_1$CCAAUCGUGGCGUGUCG$N_{19}$-$N_{20}$-$N_{21}$ACUGGCGCCG$N_{32}$, set forth by SEQ ID NO: 71 (called as General Formula Pepper structure), wherein $N_1$, $N_{19}$, $N_{20}$, $N_{21}$ and $N_{32}$ represent nucleotide fragments greater than or equal to 1 in length, and at least one base pair in $N_1$ and $N_{32}$ nucleotide sequences forms a complementary pair, and at least one base p air in $N_{19}$ and $N_{21}$ nucleotide sequences forms a complementary pair;
- (b): a nucleotide sequence with an identity of at least 70% to the nucleotide sequence defined by (a); and
- (c): a nucleic acid aptamer molecule derived from (a) at a position not including $N_1$, $N_{19}$, $N_{20}$, $N_{21}$ and $N_{32}$ in the nucleotide sequence defined by (a), with substitution, missing and/or addition of one or several nucleotides, and having an aptamer function.

In some embodiments, the nucleotide sequence (b) has an identity of at least 75%, 76%, 78%, 80%, 82%, 85%, 87%, 90%, 93%, 95%, 96%, 97%, 98%, 99% or 100% to the General Formula Pepper structure nucleotide sequence defined by the nucleotide sequence (a). In some embodiments, the nucleotide sequence (c) is nucleic acid aptamer molecules obtained with substitution, missing and/or addition of 10, 9, 8, 7, 6, 5, 4, 3, 2 or one nucleotide at a position in the General Formula Pepper structure nucleotide sequence defined by the nucleotide sequence (a) and not including $N_1$, $N_{19}$, $N_{20}$, $N_{21}$ and $N_{32}$. In some embodiments, the nucleotide sequence (c) is nucleic acid aptamer molecules obtained with substitution, missing and/or addition of 7, 6, 5, 4, 3, 2 or one nucleotide at a position in the General Formula Pepper structure nucleotide sequence defined by the nucleotide sequence (a) and not including $N_1$, $N_{19}$, $N_{20}$, $N_{21}$ and $N_{32}$.

In some embodiments, when $N_1$ and $N_{32}$ in the nucleotide sequence (a) form a complementary pair, a direction of $N_1$ nucleotide sequence is 5'-3', and a direction of $N_{32}$ nucleotide sequence is 3'-5'; and when $N_{19}$ and $N_{21}$ form a complementary pair, a direction of $N_{19}$ nucleotide sequence is 5'-3', and a direction of $N_{21}$ nucleotide sequence is 3'-5'.

In some embodiments, when at least one fragment of $N_1$ and $N_{32}$ in the nucleotide sequence (a) is greater than or equal to 5 nucleotide bases in length, at least two base pairs in $N_1$ and $N_{32}$ nucleotide sequences form complementary pairs; when at least one fragment of $N_{19}$ and $N_{21}$ is greater than or equal to 5 nucleotide bases in length, at least two base pairs in $N_{19}$ and $N_{21}$ nucleotide sequences form complementary pairs.

In some embodiments, the nucleotide substitution in the General Formula Pepper structure is selected from one of the following groups: C3A, C3U, A4U, A4G, A4C, A5G, A5C, U6A, U6G, U6C, C7A, C7U, G8C, U9A, G11A, G11U, C12G, C12A, C12U, G13C, U14A, U14G, C17U, G18U, G18C, C27G, C27U, G28U, C29G, C29U, C30A, C30U, C2G/G31C, C2U/G31A, C2A/G31U, G10A/C30U, G10C/C30G, G10U/C30A, C2G/G31C/C3A, C2G/G31C/A4C, C2G/G31C/A5C, C2G/G31C/G8C, C2G/G31C/C12U, C2G/G31C/U14G, C2G/G31C/C27U, C2G/G31C/C29G, C2G/G31C/C30U, C2G/G31C/G10A/C30U, C2G/G31C/G10C/C30G, C2G/G31C/G10U/C30A, C2U/G31A/G10A/C30U, C2U/G31A/G10C/C30G, C2U/G31A/G10U/C30A, C2A/G31U/G10A/C30U, C2A/G31U/G10C/C30G, C2A/G31U/G10U/C30A, C2G/G31C/G10C/C30G/C3A, C2G/G31C/G10C/C30G/A4C, C2G/G31C/G10C/C30G/A5C, C2G/G31C/G10C/C30G/G8C, C2G/G31C/G10C/C30G/C12U, C2G/G31C/G10C/C30G/U14G, C2G/G31C/G10C/C30G/C27U, C2G/G31C/G10C/C30G/C29G, C2G/G31C/G10A/C30U/U6G/C27U, C2G/G31C/G10C/C30G/U6G/C27U, C2G/G31C/G10U/C30A/U9A/U14G/C27U and C2A/G31U/G10U/C30A/U9A/U14G/C27U.

In some embodiments, the nucleotide substitution in the General Formula Pepper structure is selected from one of the following groups: C3A, C3U, A4C, A5C, C7U, G8C, U9A, C12G, C12U, U14G, C27U, C29G, C30U, C2G/G31C, C2U/G31A, C2A/G31U, G10A/C30U, G10C/C30G, G10U/C30A, C2G/G31C/C3A, C2G/G31C/A4C, C2G/G31C/A5C, C2G/G31C/G8C, C2G/G31C/C12U, C2G/G31C/U14G, C2G/G31C/C27U, C2G/G31C/C29G, C2G/G31C/C30U, C2G/G31C/G10A/C30U, C2G/G31C/G10C/C30G, C2G/G31C/G10U/C30A, C2U/G31A/G10A/C30U, C2U/G31A/G10C/C30G, C2U/G31A/G10U/C30A, C2A/G31U/G10A/C30U, C2A/G31U/G10C/C30G, C2A/G31U/G10U/C30A, C2G/G31C/G10C/C30G/C3A, C2G/G31C/G10C/C30G/A4C, C2G/G31C/G10C/C30G/A5C, C2G/G31C/G10C/C30G/G8C, C2G/G31C/G10C/C30G/C12U, C2G/G31C/G10C/C30G/U14G, C2G/G31C/G10C/C30G/C27U, C2G/G31C/G10C/C30G/C29G, C2G/G31C/G10A/C30U/U6G/C27U and C2G/G31C/G10C/C30G/U6G/C27U.

In some embodiments, the nucleotide substitution in the General Formula Pepper structure is selected from one of the following groups: C3A, G3U, A4C, A5C, C7U, G8C, U9A, C12G, C12U, U14G, C27U, C29G, C30U, C2G/G31C, C2U/G31A, C2A/G31U, G10A/C30U, G10C/C30G, G10U/C30A, C2G/G31C/C3A, C2G/G31C/A4C, C2G/G31C/A5C, C2G/G31C/G8C, C2G/G31C/C12U, C2G/G31C/U14G, C2G/G31C/C27U, C2G/G31C/C29G, C2G/G31C/C30U, C2G/G31C/G10A/C30U, C2G/G31C/G10C/C30G, C2G/G31C/G10U/C30A, C2U/G31A/G10A/C30U, C2U/

G31A/G10C/C30G, C2U/G31A/G10U/C30A, C2A/G31U/G10A/C30U, C2A/G31U/G10C/C30G and C2A/G31U/G10U/C30A.

In some embodiments, nucleotide sequences at $N_1$ and $N_{32}$ in the nucleotide sequence (a) are F30 or tRNA scaffold RNA sequences.

In some embodiments, the nucleic acid aptamer molecules are RNA molecules or RNA base-modified molecules.

In some embodiments, the nucleic acid aptamer molecules are DNA-RNA hybrid molecules or DNA-RNA base-modified molecules.

In some embodiments, $N_{19}$-$N_{20}$-$N_{21}$ in the nucleotide sequence (a) contains a nucleotide sequence capable of identifying target molecules.

In some embodiments, the target molecules include but are not limited to: proteins, nucleic acid, lipid molecules, carbohydrates, hormones, cytokines, chemokines, and metabolite metal ions.

In some embodiments, $N_{19}$-$N_{20}$-$N_{21}$ in the nucleotide sequence (a) is a nucleotide sequence capable of identifying GTP and adenosine molecules.

In some embodiments, the aptamer function refers to that the nucleic acid aptamer can enhance fluorescence intensity of fluorophore molecules under excitation light of appropriate wavelength by at least two times, at least 5 to 10 times, at least 20 to 50 times, at least 100 to 200 times or at least 500 to 1,000 times.

In some embodiments, the nucleic acid aptamer molecules may further include concatemers that can bind multiple fluorophore molecules, and the concatemers are connected by spacer sequences of appropriate length having 2, 3, 4, 5, 6, 7, 8 or more nucleotide fragments. Nucleotides of the concatemers can be selected from but are not limited to a sequence SEQ ID No: 8, 9, 10, 11, 12, 13, 14, 15, 16, 17, 18 and 19.

In some embodiments, the nucleic acid aptamer molecules have a sequence SEQ ID No: 1, 2, 3, 6, 7, 8, 9, 10, 11, 12, 13, 14, 15, 16, 17, 18, 19, 21, 22 or 23.

The present application further provides a complex of nucleic acid aptamer molecules and fluorophore molecules, wherein the nucleic acid aptamer molecules are any kind of the afore-mentioned nucleic acid aptamer molecules, and the fluorophore molecules have a structure shown in Formula (I) below:

(I)

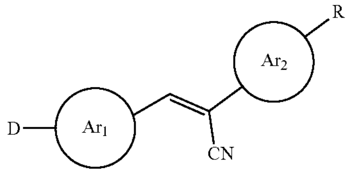

wherein: D- is $X_1O$— or $N(X_2)(X_3)$—; $X_1$, $X_2$, $X_3$ are respectively and independently selected from hydrogen, straight or branched alkyl and modified alkyl with 1 to 10 carbons, and $X_2$ and $X_3$ are optionally interconnected to be a satured or unsatured ring; R— is selected from hydrogen, cyano group, carboxyl, amide group, ester group, hydroxy, and straight or branched alkyl or modified alkyl with 1 to 10 carbons; $Ar_1$ and $Ar_2$ are respectively and independently selected from monocyclic aryl subunits, monocyclic heteroaryl subunits, or aromatic subunits with 2 to 3 ring structures condensed from one or both of monocyclic aryl group and monocyclic heteroaryl group;

wherein: hydrogen atoms in $Ar_1$ and $Ar_2$ can be independently substituted by F, Cl, Br, I, hydroxyl group, nitro group, aldehyde group, carboxyl group, cyano group, sulfonic acid group, sulfuric acid group, phosphoric acid group, amino group, primary amino group, secondary amino group, straight or branched alkyl and modified alkyl with 1 to 10 carbons;

wherein: the modified alkyl is a group obtained by replacing any carbon atom of the alkyl with at least one group selected from F, Cl, Br, I, —O—, —OH, —CO—, —$NO_2$, —CN, —S—, —$SO_2$—, —(S=O)—, azide group, phenylene, primary amino group, secondary amino group, tertiary amino group, quaternary ammonium group, ethylene oxide, succinate, isocyanate, isothiocyanate, acyl chloride, sulfonyl chloride, saturated or unsaturated monocyclic or dicyclic subcyclic hydroxyl, bridged ester heterocycle, and the modified alkyl has 1 to 10 carbon atoms, wherein the carbon-carbon single bond is optionally and independently replaced by a carbon-carbon double bond or a carbon-carbon triple bond; and wherein the nucleic acid aptamer molecules and the fluorophore molecules in the complex respectively exist in an individual solution, or the nucleic acid aptamer molecules and the fluorophore molecules are in the same solution.

In some embodiments, the modified alkyl contains at least one group selected from —OH, —O—, glycol unit, monosaccharide unit, disaccharide unit, —O—CO—, —NH—CO—, —$SO_2$—O—, —SO—, $Me_2N$—, $Et_2N$—, —S—S—, —CH=CH—, F, Cl, Br, I, —$NO_2$ and cyano group.

In some embodiments, aromatic rings contained in the fluorophore molecules are selected from structures represented by the following formulae (II-1) to (II-15):

(II-1)

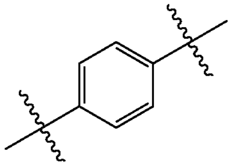

, (II-2)

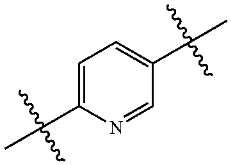

, (II-3)

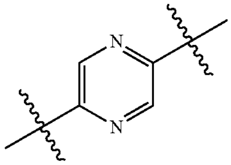

, (II-4)

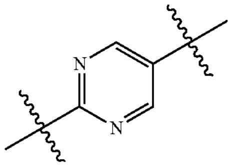

,

-continued
(II-5)
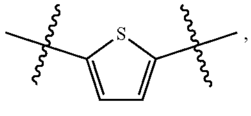
(II-6)
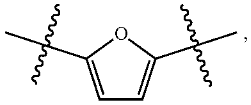
(II-7)
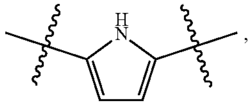
(II-8)
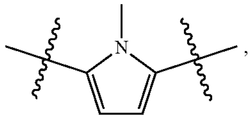
(II-9)
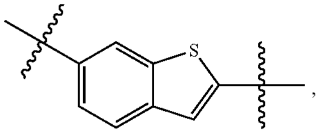
(II-10)
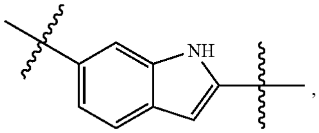
(II-11)
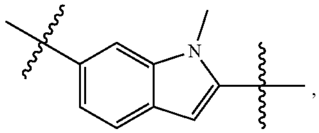
(II-12)
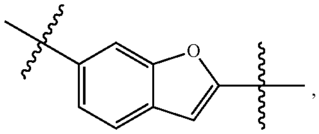
(II-13)
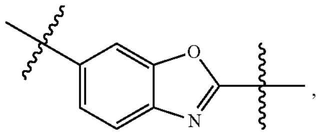
(II-14)
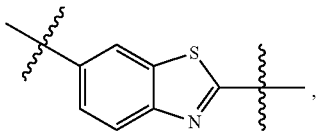
(II-15)
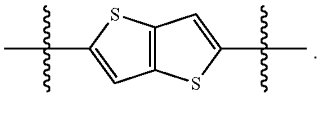
In some embodiments, fluorophore molecules are selected from the following compounds represented by the following formulae:
III-1
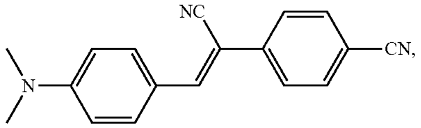
III-2
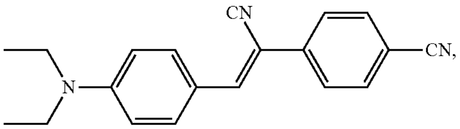
III-3
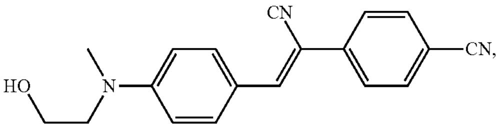
III-4
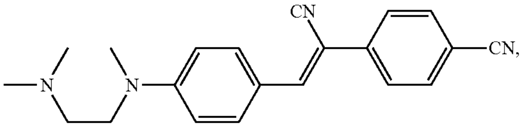
III-5
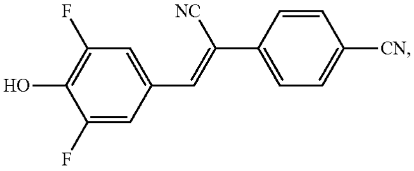
III-6
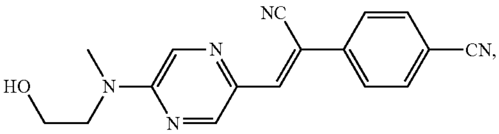
III-7
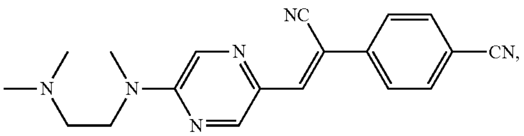
III-8
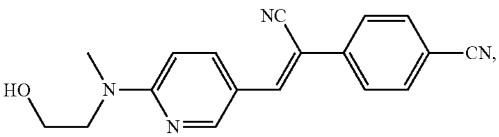
III-9
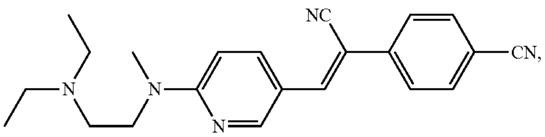
III-10
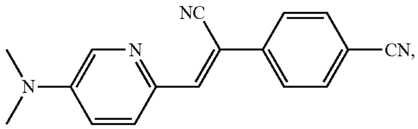

-continued

III-11

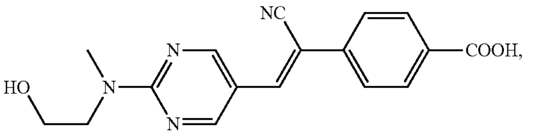

III-12

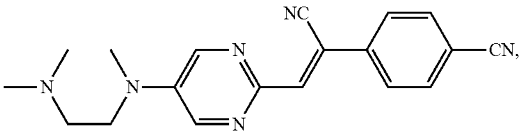

III-13

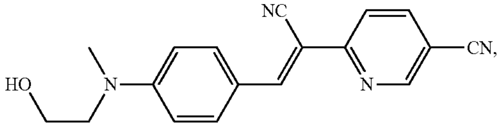

III-14

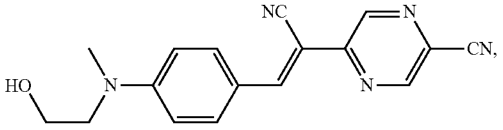

III-15

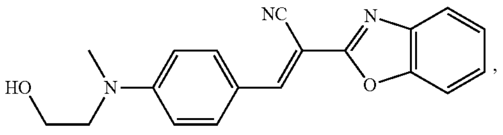

III-16

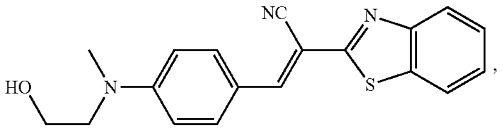

III-17

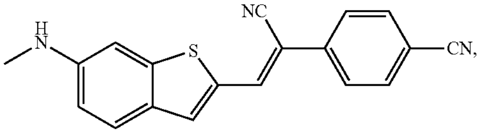

III-17

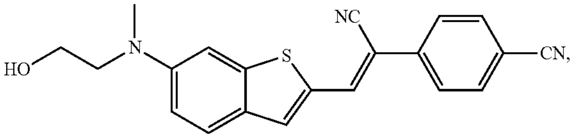

III-19

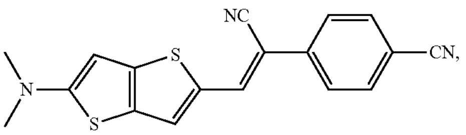

III-20

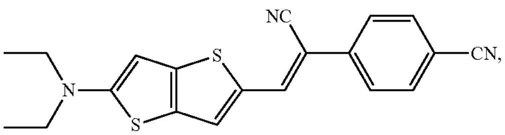

-continued

III-21

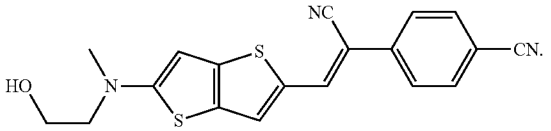

In some embodiments, the fluorophore molecules in the complex are selected from III-1, III-2, III-3, III-4, III-5, III-6, III-7, III-8, III-9, III-10, III-11, III-12, III-13, III-14, III-15, III-16, III-17, III-18, III-19, III-20 and III-21.

In some embodiments, the aptamer molecules in the complex contain nucleotide sequence SEQ ID No: 1, 2, 3, 6, 7, 8, 9, 10, 11, 12, 13, 14, 15, 16, 17, 18, 19, 21, 22, 23, 24, 25, 26, 27, 28, 29, 30 or 31.

The present application further provides any of the aforementioned complexes used for detection or labeling of target nucleic acid molecules in vitro or in vivo.

The present application further provides any of the aforementioned complexes used for detection or labeling of extracellular or intracellular target molecules.

The present application further provides any of the aforementioned complexes used for imaging of genomic DNA.

The present application further provides any of the aforementioned complexes used for detecting a relationship between mRNA and protein content in cells.

The present application further provides a DNA molecule which transcribes any of the nucleic acid aptamer molecules.

The present application further provides an expression vector containing the DNA molecules.

The present application further provides a host cell containing the expression vector.

The present application further provides a kit containing any of the nucleic acid aptamer molecules and/or any of the expression vectors and/or any of the host cells and/or any of the complexes.

The present application further provides a method of detecting target molecules, including:

adding any of the complexes to a solution containing the target molecules;

exciting the complex with light of appropriate wavelength; and detecting fluorescence of the complex.

The present application further provides a method of detecting genome DNA, including imaging genome DNA with any of the complexes.

The present application further provides a method of extracting and purifying RNA, including extracting and purifying RNA with any of the complexes.

The inventor designed brand new nucleic acid aptamer molecules, and synthesized brand new fluorophore molecules, so as to form a brand new fluorophore-nucleic acid aptamer complex. After binding of the aptamer molecules to the fluorophore molecules, the fluorescence intensity of the fluorophore molecules can be significantly increased under the excitation light of appropriate wavelength. They overcome the shortcomings of previous fluorophore-nucleic acid aptamer complexes, and can be used for effective real-time RNA/DNA labeling in living cells. The nucleic acid aptamer of the present application have a strong affinity for fluorophore molecules, and shows different fluorescence spectra and fine light and temperature stability. These nucleic acid aptamer-fluorophore molecule complexes can be used for real-time labeling and imaging of RNA/DNA in prokaryotic and eukaryotic cells, detecting protein-RNA interactions, exploring the relationship between mRNA content and protein in cells, or as labels for RNA extraction and purification.

EXAMPLES

Figure 1:
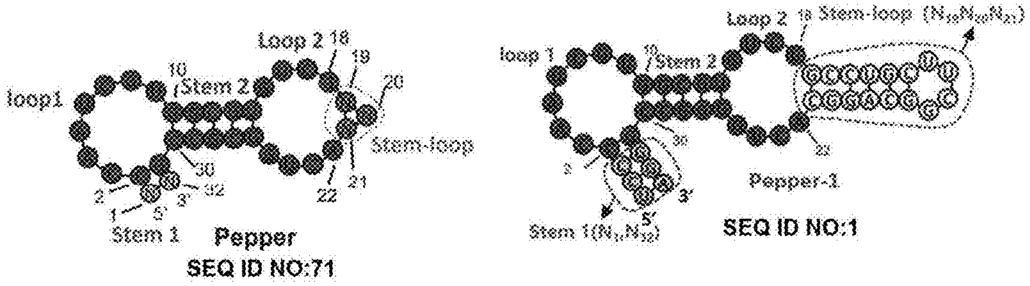
FIG. 1 Secondary structure prediction of nucleic acid aptamer molecules. (A) is the predicted general structure of Pepper, comprising $N_1$ and $N_{32}$ that can form a stem structure, and $N_{19}$, $N_{20}$ and $N_{21}$ that can form a stem-loop structure. (B) is the predicted general structure of Pepper-1, wherein the base sequence of $N_1$ and $N_{32}$ is shown in the dotted box corresponding to Stem 1 in the drawing, and the base sequence of $N_{19}$, $N_{20}$ and $N_{21}$ is shown in the dotted box corresponding to the stem-loop.

The following definitions and embodiments cited in the present application will be described in details here. The contents of all patents and published literature referred to herein, including all sequences disclosed in these patents and published literature, are expressly incorporated herein by reference. Hereinafter, "nucleotides" and "nucleotide bases" are used interchangeably and stand for the same meaning.

Following are detailed explanations of some terms used in the present application.

Nucleic Acid Aptamer Molecules

The "nucleic acid aptamer molecules" of the present application are also referred to as "a ptamer molecules". The nucleic acid aptamer molecule contains (a) a nucleotide sequence $N_1$CCA AUCGUGGCGUGUCG$N_{19}$-$N_{20}$-$N_{21}$ACUGGCGCCG$N_{32}$, set forth by SEQ ID NO: 71 (corresponding to the General Formula Pepper structure in FIG. 1A); or (b) which is a nucleotide sequence with an identity of at least 70% to the nucleotide sequence of (a); wherein at least one base pair in $N_1$ and $N_{32}$ nucleotide sequences forms a reverse complementary pair, namely, the direction of $N_1$ nucleotide sequence is 5'-3', and the direction of $N_{32}$ nucleotide sequence is 3'-5'. When the length of at least one nucleotide base of $N_1$ and $N_{32}$ is smaller than or equal to 4, at least one base pair is needed for forming the complementary pair; and when the length of at least one nucleotide base of $N_1$ and $N_{32}$ is greater than or equal to 5, at least two base pairs are needed for forming the complementary pair. Wherein, at least one base pair in $N_{19}$ and $N_{21}$ nucleotide sequences forms a reverse complementary pair, namely, the direction of $N_{19}$ nucleotide sequence is 5'-3', and the direction of $N_{21}$ nucleotide sequence is 3'-5'. When the length of at least one nucleotide base of $N_{19}$ and $N_{21}$ is smaller than or equal to 4, at least one base pair is needed for forming the complementary p air; and when the length of at least one nucleotide base of $N_{19}$ and $N_{21}$ is greater than or equal to 5, at least two base pairs are needed for forming the complementary pair. $N_{20}$ therein is a nucleotide base of any length or composition; or (c) which is at any position in the nucleotide sequence (a) with the substitution, missing and/or addition of 1 to 7 nucleotides.

The nucleic acid aptamer molecules contain substitution of the nucleotides in General Formula Pepper structure, the substitution being selected from one of the following groups: C3A, C3U, A4U, A4G, A4C, A5G, A5C, U6A, U6G, U6C, C7A, C7U, G8C, U9A, G11A, G11U, C12G, C12A, C12U, G13C, U14A, U14G, C17U, G18U, G18C, C27G, C27U, G28U, C29G, C29U, C30A, C30U, C2G/

G31C, C2U/G31A, C2A/G31U, G10A/C30U, G10C/C30G, G10U/C30A, C2G/G31C/C3A, C2G/G31C/A4C, C2G/G31C/A5C, C2G/G31C/G8C, C2G/G31C/C12U, C2G/G31C/U14G, C2G/G31C/C27U, C2G/G31C/C29G, C2G/G31C/C30U, C2G/G31C/G10A/C30U, C2G/G31C/G10C/C30G, C2G/G31C/G10U/C30A, C2U/G31A/G10A/C30U, C2U/G31A/G10C/C30G, C2U/G31A/G10U/C30A, C2A/G31U/G10A/C30U, C2A/G31U/G10C/C30G, C2A/G31U/G10U/C30A, C2G/G31C/G10C/C30G/C3A, C2G/G31C/G10C/C30G/A4C, C2G/G31C/G10C/C30G/A5C, C2G/G31C/G10C/C30G/G8C, C2G/G31C/G10C/C30G/C12U, C2G/G31C/G10C/C30G/U14G, C2G/G31C/G11C/C30G/C27U, C2G/G31C/G10C/C30G/C29G, C2G/G31C/G10A/C30U/U6G/C27U, C2G/G31C/G10C/C30G/U6G/C27U, C2G/G31C/G10U/C30A/U9A/U14G/C27U and C2A/G31U/G10U/C30A/U9A/U14G/C27U (which are the aptamer molecule structures in Table 1). These mutants can specifically bind fluorophore molecules, and can significantly increase fluorescence intensity of fluorophore molecules under excitation light of appropriate wavelength after binding. The nucleotide position sequence corresponds to the position shown in FIG. 1A.

The afore-mentioned mutants indicate that nucleotide substitution occurs at the corresponding sites of the aptamer nucleotide sequence of the General Formula Pepper structure. For example, C3A indicates that the cytosine nucleotide C at the third position of Pepper is substituted by adenine nucleotide A, i.e. Pepper (C3A) in Table 1; C2G/G31C indicates that C at the second position of Pepper is substituted by G, and G at the 31$^{st}$ position is substituted by C, i.e. Pepper (C2G/G31C) in Table 1.

Table 1: Aptamer structure of Pepper general formula structure after substitution of 7, 6, 5, 4, 3, 2 or one nucleotide

TABLE 1

Aptamer structure of Pepper general formula structure after substitution of 7, 6, 5, 4, 3, 2 or one nucleotide

| Substitutions of Pepper general formula structure | SEQ ID NO | Aptamer structure general formula after substitution (underlined are bases after substitution) |
|---|---|---|
| Pepper (C3A) | 72 | $N_1$CAAAUCGUGGCGUGUCG$N_{19}$-$N_{20}$-$N_{21}$ACUGGCGCCG$N_{32}$ |
| Pepper (C3U) | 73 | $N_1$CUAAUCGUGGCGUGUCG$N_{19}$-$N_{20}$-$N_{21}$ACUGGCGCCG$N_{32}$ |
| Pepper (A4U) | 78 | $N_1$CCUAUCGUGGCGUGUCG$N_{19}$-$N_{20}$-$N_{21}$ACUGGCGCCG$N_{32}$ |
| Pepper (A4G) | 79 | $N_1$CCGAUCGUGGCGUGUCG$N_{19}$-$N_{20}$-$N_{21}$ACUGGCGCCG$N_{32}$ |
| Pepper (A4C) | 80 | $N_1$CCCAUCGUGGCGUGUCG$N_{19}$-$N_{20}$-$N_{21}$ACUGGCGCCG$N_{32}$ |
| Pepper (A5G) | 81 | $N_1$CCAGUCGUGGCGUGUCG$N_{19}$-$N_{20}$-$N_{21}$ACUGGCGCCG$N_{32}$ |
| Pepper (A5C) | 82 | $N_1$CCACUCGUGGCGUGUCG$N_{19}$-$N_{20}$-$N_{21}$ACUGGCGCCG$N_{32}$ |
| Pepper (U6A) | 83 | $N_1$CCAAACGUGGCGUGUCG$N_{19}$-$N_{20}$-$N_{21}$ACUGGCGCCG$N_{32}$ |
| Pepper (U6G) | 84 | $N_1$CCAAGCGUGGCGUGUCG$N_{19}$-$N_{20}$-$N_{21}$ACUGGCGCCG$N_{32}$ |
| Pepper (U6C) | 85 | $N_1$CCAACCGUGGCGUGUCG$N_{19}$-$N_{20}$-$N_{21}$ACUGGCGCCG$N_{32}$ |
| Pepper (C7A) | 86 | $N_1$CCAAUAGUGGCGUGUCG$N_{19}$-$N_{20}$-$N_{21}$ACUGGCGCCG$N_{32}$ |
| Pepper (C7U) | 87 | $N_1$CCAAUUGUGGCGUGUCG$N_{19}$-$N_{20}$-$N_{21}$ACUGGCGCCG$N_{32}$ |
| Pepper (G8C) | 88 | $N_1$CCAAUCCUGGCGUGUCG$N_{19}$-$N_{20}$-$N_{21}$ACUGGCGCCG$N_{32}$ |
| Pepper (U9A) | 89 | $N_1$CCAAUCGAGGCGUGUCG$N_{19}$-$N_{20}$-$N_{21}$ACUGGCGCCG$N_{32}$ |
| Pepper (G11A) | 90 | $N_1$CCAAUCGUGACGUGUCG$N_{19}$-$N_{20}$-$N_{21}$ACUGGCGCCG$N_{32}$ |
| Pepper (G11U) | 91 | $N_1$CCAAUCGUGUCGUGUCG$N_{19}$-$N_{20}$-$N_{21}$ACUGGCGCCG$N_{32}$ |
| Pepper (C12G) | 92 | $N_1$CCAAUCGUGGGGUGUCG$N_{19}$-$N_{20}$-$N_{21}$ACUGGCGCCG$N_{32}$ |
| Pepper (C12A) | 93 | $N_1$CCAAUCGUGGAGUGUCG$N_{19}$-$N_{20}$-$N_{21}$ACUGGCGCCG$N_{32}$ |
| Pepper (C12U) | 94 | $N_1$CCAAUCGUGGUGUGUCG$N_{19}$-$N_{20}$-$N_{21}$ACUGGCGCCG$N_{32}$ |
| Pepper (G13C) | 95 | $N_1$CCAAUCGUGGCCUGUCG$N_{19}$-$N_{20}$-$N_{21}$ACUGGCGCCG$N_{32}$ |
| Pepper (U14A) | 96 | $N_1$CCAAUCGUGGCGAGUCG$N_{19}$-$N_{20}$-$N_{21}$ACUGGCGCCG$N_{32}$ |
| Pepper (U14G) | 97 | $N_1$CCAAUCGUGGCGGGUCG$N_{19}$-$N_{20}$-$N_{21}$ACUGGCGCCG$N_{32}$ |
| Pepper (C17U) | 98 | $N_1$CCAAUCGUGGCGUGUUG$N_{19}$-$N_{20}$-$N_{21}$ACUGGCGCCG$N_{32}$ |
| Pepper (G18U) | 99 | $N_1$CCAAUCGUGGCGUGUCU$N_{19}$-$N_{20}$-$N_{21}$ACUGGCGCCG$N_{32}$ |
| Pepper (G18C) | 100 | $N_1$CCAAUCGUGGCGUGUCC$N_{19}$-$N_{20}$-$N_{21}$ACUGGCGCCG$N_{32}$ |
| Pepper (C27G) | 101 | $N_1$CCAAUCGUGGCGUGUCG$N_{19}$-$N_{20}$-$N_{21}$ACUGGGGCCG$N_{32}$ |
| Pepper (C27U) | 102 | $N_1$CCAAUCGUGGCGUGUCG$N_{19}$-$N_{20}$-$N_{21}$ACUGGUGCCG$N_{32}$ |
| Pepper (G28U) | 103 | $N_1$CCAAUCGUGGCGUGUCG$N_{19}$-$N_{20}$-$N_{21}$ACUGGCUCCG$N_{32}$ |
| Pepper (C29G) | 104 | $N_1$CCAAUCGUGGCGUGUCG$N_{19}$-$N_{20}$-$N_{21}$ACUGGCGGCG$N_{32}$ |
| Pepper (C29U) | 105 | $N_1$CCAAUCGUGGCGUGUCG$N_{19}$-$N_{20}$-$N_{21}$ACUGGCGUCG$N_{32}$ |
| Pepper (C30A) | 106 | $N_1$CCAAUCGUGGCGUGUCG$N_{19}$-$N_{20}$-$N_{21}$ACUGGCGCAG$N_{32}$ |
| Pepper (C30U) | 107 | $N_1$CCAAUCGUGGCGUGUCG$N_{19}$-$N_{20}$-$N_{21}$ACUGGCGCUG$N_{32}$ |
| Pepper (C2G/G31C) | 108 | $N_1$GCAAUCGUGGCGUGUCG$N_{19}$-$N_{20}$-$N_{21}$ACUGGCGCCC$N_{32}$ |
| Pepper (C2U/G31A) | 109 | $N_1$UCAAUCGUGGCGUGUCG$N_{19}$-$N_{20}$-$N_{21}$ACUGGCGCCA$N_{32}$ |
| Pepper (C2A/G31U) | 110 | $N_1$ACAAUCGUGGCGUGUCG$N_{19}$-$N_{20}$-$N_{21}$ACUGGCGCCU$N_{32}$ |
| Pepper (C10A/C30U) | 111 | $N_1$CCAAUCGUAGCGUGUCG$N_{19}$-$N_{20}$-$N_{21}$ACUGGCGCUG$N_{32}$ |
| Pepper (C10C/C30G) | 112 | $N_1$CCAAUCGUCGCGUGUCG$N_{19}$-$N_{20}$-$N_{21}$ACUGGCGCGG$N_{32}$ |
| Pepper (C10U/C30A) | 113 | $N_1$CCAAUCGUUGCGUGUCG$N_{19}$-$N_{20}$-$N_{21}$ACUGGCGCAG$N_{32}$ |
| Pepper (C2G/G31/C3A) | 114 | $N_1$GAAAUCGUGGCGUGUCG$N_{19}$-$N_{20}$-$N_{21}$ACUGGCGCCC$N_{32}$ |
| Pepper (C2G/G31C/A4C) | 115 | $N_1$GCCAUCGUGGCGUGUCG$N_{19}$-$N_{20}$-$N_{21}$ACUGGCGCCC$N_{32}$ |
| Pepper (C2G/G31C/A5C) | 116 | $N_1$GCACUCGUGGCGUGUCG$N_{19}$-$N_{20}$-$N_{21}$ACUGGCGCCC$N_{32}$ |
| Pepper (C2G/G31C/G8C) | 117 | $N_1$GCAAUCCUGGCGUGUCG$N_{19}$-$N_{20}$-$N_{21}$ACUGGCGCCC$N_{32}$ |
| Pepper (C2G/G31C/C12U) | 118 | $N_1$GCAAUCGUGGUGUGUCG$N_{19}$-$N_{20}$-$N_{21}$ACUGGCGCCC$N_{32}$ |
| Pepper (C2G/G31C/U14G) | 119 | $N_1$GCAAUCGUGGCGGGUCG$N_{19}$-$N_{20}$-$N_{21}$ACUGGCGCCC$N_{32}$ |
| Pepper (C2G/G31C/C27U) | 120 | $N_1$GCAAUCGUGGCGUGUCG$N_{19}$-$N_{20}$-$N_{21}$ACUGGUGCCC$N_{32}$ |
| Pepper (C2G/G31C/C29G) | 121 | $N_1$GCAAUCGUGGCGUGUCG$N_{19}$-$N_{20}$-$N_{21}$ACUGGCGGCC$N_{32}$ |
| Pepper (C2G/G31C/C30U) | 122 | $N_1$GCAAUCGUGGCGUGUCG$N_{19}$-$N_{20}$-$N_{21}$ACUGGCGCUC$N_{32}$ |
| Pepper (C2G/G31C/G10A/C30U) | 123 | $N_1$GCAAUCGUAGCGUGUCG$N_{19}$-$N_{20}$-$N_{21}$ACUGGCGCUC$N_{32}$ |

TABLE 1-continued

Aptamer structure of Pepper general formula structure after substitution of 7, 6, 5, 4, 3, 2 or one nucleotide

| Substitutions of Pepper general formula structure | SEQ ID NO | Aptamer structure general formula after substitution (underlined are bases after substitution) |
|---|---|---|
| Pepper (C2G/G31C/G10C/C30G) | 124 | $N_1$GCAAUCGUCGCGUGUCG$N_{19}$-$N_{20}$-$N_{21}$ACUGGCGCGC$N_{32}$ |
| Pepper (C2G/G31C/G10U/C30A) | 125 | $N_1$GCAAUCGUUGCGUGUCG$N_{19}$-$N_{20}$-$N_{21}$ACUGGCGCAC$N_{32}$ |
| Pepper (C2U/G31A/G10C/C30G) | 126 | $N_1$UCAAUCGUCGCGUGUCG$N_{19}$-$N_{20}$-$N_{21}$ACUGGCGCGA$N_{32}$ |
| Pepper (C2U/G31A/G10U/C30A) | 127 | $N_1$UCAAUCGUUGCGUGUCG$N_{19}$-$N_{20}$-$N_{21}$ACUGGCGCAA$N_{32}$ |
| Pepper (C2A/G31U/G10A/C30U) | 128 | $N_1$ACAAUCGUAGCGUGUCG$N_{19}$-$N_{20}$-$N_{21}$ACUGGCGCUU$N_{32}$ |
| Pepper (C2A/G31U/G10C/C30G) | 129 | $N_1$ACAAUCGUCGCGUGUCG$N_{19}$-$N_{20}$-$N_{21}$ACUGGCGCGU$N_{32}$ |
| Pepper (C2A/G31U/G10U/C30A) | 130 | $N_1$ACAAUCGUUGCGUGUCG$N_{19}$-$N_{20}$-$N_{21}$ACUGGCGCAU$N_{32}$ |
| Pepper (C2G/G31C/G10C/C30G/C3A) | 131 | $N_1$GAAAUCGUCGCGUGUCG$N_{19}$-$N_{20}$-$N_{21}$ACUGGCGCGC$N_{32}$ |
| Pepper (C2G/G31C/G10C/C30G/A4C) | 132 | $N_1$GCCAUCGUCGCGUGUCG$N_{19}$-$N_{20}$-$N_{21}$ACUGGCGCGC$N_{32}$ |
| Pepper (C2G/G31C/G10C/C30G/A5C) | 133 | $N_1$GCACUCGUCGCGUGUCG$N_{19}$-$N_{20}$-$N_{21}$ACUGGCGCGC$N_{32}$ |
| Pepper (C2G/G31C/G10C/C30G/G8C) | 134 | $N_1$GCAAUCCUCGCGUGUCG$N_{19}$-$N_{20}$-$N_{21}$ACUGGCGCGC$N_{32}$ |
| Pepper (C2G/G31C/G10C/C30G/C12U) | 135 | $N_1$GCAAUCGUCGUGUGUCG$N_{19}$-$N_{20}$-$N_{21}$ACUGGCGCGC$N_{32}$ |
| Pepper (C2G/G31C/G10C/C30G/U14G) | 136 | $N_1$GCAAUCGUCGCGGGUCG$N_{19}$-$N_{20}$-$N_{21}$ACUGGCGCGC$N_{32}$ |
| Pepper (C2G/G31C/G10C/C30G/C27U) | 13 | $N_1$GCAAUCGUCGCGGGUCG$N_{19}$-$N_{20}$-$N_{21}$ACUGGUGCGC$N_{32}$ |
| Pepper (C2G/G31C/G10C/C30G/C29G) | 138 | $N_1$GCAAUCGUCGCGGGUCG$N_{19}$-$N_{20}$-$N_{21}$ACUGGCGGGC$N_{32}$ |
| Pepper (C2G/G31C/G10C/C30G/C29G) | 139 | $N_1$GCAAUCGUCGCGGGUCG$N_{19}$-$N_{20}$-$N_{21}$ACUGGCGGGC$N_{32}$ |
| Pepper (C2G/G31C/G10A/C30U/U6G/C27U) | 140 | $N_1$GCAAGCGUAGCGUGUCG$N_{19}$-$N_{20}$-$N_{21}$ACUGGUGCUC$N_{32}$ |
| Pepper (C2G/G31C/G10C/C30G/U6G/C27U) | 141 | $N_1$GCAAGCGUCGCGUGUCG$N_{19}$-$N_{20}$-$N_{21}$ACUGGUGCGC$N_{32}$ |
| Pepper (C2G/G31C/G10U/C30A/U9A/U14G/C27U) | 142 | $N_1$GCAAUCGAUGCGGGUCG$N_{19}$-$N_{20}$-$N_{21}$ACUGGUGCAC$N_{32}$ |
| Pepper (C2A/G31U/G10U/C30A/U9A/U14G/C27U) | 143 | $N_1$ACAAUCGAUGCGGGUCG$N_{19}$-$N_{20}$-$N_{21}$ACUGGUGCAU$N_{32}$ |

Aptamer molecules are single-stranded nucleic acid molecules that have a secondary structure (FIG. 1) consisting of one or more base pairing regions (stem) and one or more unpaired regions (loop). The nucleic acid molecules of the present application contain a secondary structure as predicted in FIG. 1. The secondary structure comprises two loop structures, two stem structures and a stem-loop structure, wherein Stem 1 plays the role of stabilizing the entire nucleic acid aptamer molecule structure, and can be substituted by other nucleotide base pairs of any length and any composition that can form stem structures. The 5' end or 3' end of Stem 1 structure can be fused with any objective RNA molecule for extracellular or intracellular detection of the target RNA molecules. In a preferable embodiment of the present application, the 5' end of the nucleic acid aptamer molecule is fused with a 5S RNA sequence (Genebank: NR_023377.1); in another preferable embodiment of the present application, the 5' end of the nucleic acid aptamer molecule is fused with a GAPDH RNA sequence (Genebank: BC009081).

The stem-loop structure in FIG. 1 plays the role of stabilizing the entire nucleic acid aptamer molecule structure, and can be replaced with other nucleotide base pairs of any length and any composition that can form stem-loop structures. The aptamer molecules of the present application may also contain other nucleotide sequences that can be inserted into the position of $N_{19}$-$N_{20}$-$N_{21}$, wherein the inserted nucleotide sequence replaces the stem-loop structure in FIG. 1A. The nucleotide sequence can specifically identify/bind target molecules. In the absence of target molecules, the binding of aptamer molecules and fluorophore molecules is weak, as a result of which the fluorophore molecules show weak fluorescence light; in the presence of target molecules, the binding of target molecules and the aptamer will promote binding of the aptamer and fluorophore molecules, and thus can significantly enhance the fluorescence of fluorophore molecules under excitation light of appropriate wavelength. The target molecules can be small molecules, and signal molecules on the cell surface, etc. These nucleic acid aptamers. bind to specific target molecules through non-covalent binding, which mainly depends on intermolecular ionic forces, dipole force, hydrogen bonds, Van der Waals forces, positron and negative electron interactions, stacking or the combination of the above forces. The stem-loop structure can be replaced with an RNA sequence that identifies the target molecules for extracellular or intracellular detection of the target molecules. In a preferable embodiment of the present application, the stem-loop structure of aptamer molecules can bind GTP molecules; in another preferable embodiment of the present application, the stem-loop structures can bind adenosine molecules.

In a preferable embodiment of the present application, the nucleic acid aptamer molecules are preferably SEQ ID NO: 1, 2, 3, 6, 7, 8, 9, 10, 11, 12, 13, 14, 15, 16, 17, 18, 19, 21, 22 or 23, or their mutation sequence which can bind fluorophore molecules so as to significantly enhance the fluorescence of fluorophore molecules under excitation light of appropriate wavelength.

Figure 2:
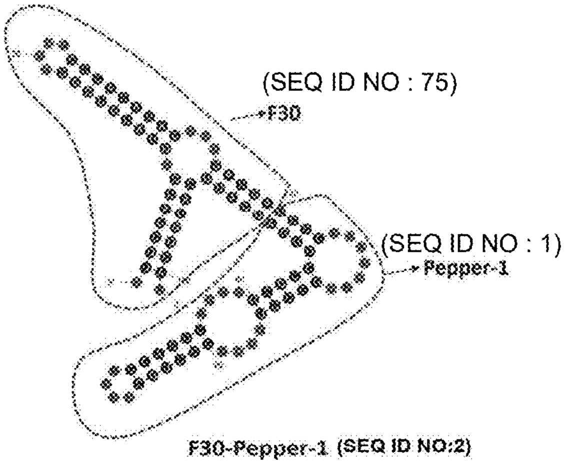
FIG. 2 Secondary structure prediction of F30-Pepper-1.
Figure 3:
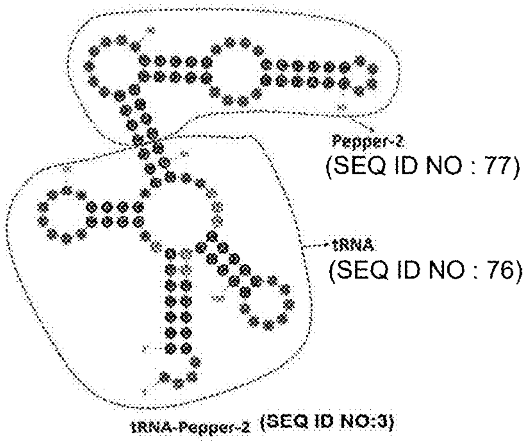
FIG. 3 Secondary structure prediction of tRNA-Pepper-2.

The nucleic acid aptamer molecules of the present application can also comprise a fragment of nucleotide sequence that increases its stability. In a preferable embodiment of the present application, F30 scaffold RNA (F30, SEQ ID NO: 752) was adopted, and the connection mode of the nucleic acid aptamer molecules including the F30 scaffold RNA (F30-Pepper-1, SEQ ID NO: 2) is shown in FIG. 2; in another preferable embodiment of the present invention, tRNA scaffold RNA (SEQ ID NO: 76) was adopted, and the connection mode of the nucleic acid aptamer molecules having the tRNA scaffold RNA (tRNA-Pepper-2, SEQ ID NO: 3) is shown in FIG. 3.

The "nucleic acid aptamer molecules" in the present application are RNA molecules, or DNA-RNA hybrid molecules with part of nucleotides being replaced with deoxyribonucleotides, wherein the nucleotides can be in a form of D and L enantiomers thereof and also contain derivatives thereof, including but not limited to 2'-F, 2'-amino, 2'-methoxyl, 5'-iodo, 5'-bromine-modified polynucleotide. Nucleic acids contain various modified nucleotides.

Identity

"Identity" describes the correlation between two nucleotide sequences in the present application. The calculation of identity of two aptamer nucleotide sequences in the present application does not include $N_1$, $N_{19}$, $N_{20}$, $N_{21}$, $N_{32}$ in Sequence (a). As for the present application, identity of two aptamer nucleotide sequences is determined by using, for instance, Needle program, preferably Needleman-Wunsch Algorithm (Needleman and Wunsch, 1970, J. Mol. Biol. 48: 443-453) executed in 3.0.0 version or later, of EMBOSS software package (EMBOSS: The European Molecular Biology Open Software Suite, Rice etc., 2000, Trends in Genetics 16: 276-277). Optional parameters in use are gap penalty 10, gap extension penalty 0.5 and EBLOSUM62 substitution matrix (EMBOSS version of BLOSUM62). Output result marked by Needle as "longest identity" (obtained by using the "–nobrief" option) serves as the percentage identity, and is calculated in a way as follows:

$$(\text{Identical residue} \times 100)/(\text{Alignment length} - \text{Total number of gaps in alignment}).$$

For instance, the sequence of Pepper (C3A) in Table 1 of the present application is N1CAAAUCGUGGCGUGUCGN19-N20-N21ACUGGCGCCGN32, set forth by SEQ ID NO: 72, and the sequence of Pepper (C3U) is NICUAAUCGUGGCGUGUCGN19-N20-N21ACUGGCGCCGN32, set forth by SEQ ID NO: 73, and, according to the definition of the present application, their identity alignment should not include the nucleotide bases of N1, N19-N20-N21 and N32, so the alignment result of their sequence identity is 96.3% (the difference being one nucleotide).

Fluorophore Molecules

The "fluorophore molecules" in the present application are also called as "fluorophore" or "fluorescence molecules". "Fluorophore molecules" in the present application are a kind of fluorophore molecules that can be conditionally activated, and show a relatively low quantum yield in the absence of nucleic acid aptamers. In specific embodiments, when a fluorophore is not bound to specific aptamers, its quantum yield is lower than 0.1, preferably lower than 0.01, and optimally lower than 0.001; when the fluorophore is bound to specific aptamers, its quantum yield will be enhanced by more than two times, preferably by more than 10 times, and optimally by more than 100 times. Fluorophore molecules are preferably water-soluble, non-toxic to cells and easy to penetrate membranes. Fluorophore of the present application can preferably enter cytoplasm or pericytoplasm through membrane or cell wall by means of active transport or passive diffusion. In the embodiments of the present application, the fluorophore can penetrate outer and inner membranes of Gram-negative bacteria, cell walls and membranes of plant cells, cell walls and membranes of fungi, membranes of animal cells, and GI and endothelial membranes of living animals.

The nucleic acid aptamer molecules in the present application can specifically bind a fluorophore and significantly increase its fluorescence value under excitation light of specific wavelength. The expressions such as "improving fluorescence signals", "fluorescence increase", "enhancing fluorescence intensity", "improving fluorescence intensity" in the present application refers to the increase of the quantum yield of the fluorophore or the migration (relative to emission peaks of fluorophore itself in ethanol or aqueous solution) of the maximum emission peak of fluorescence signals under the excitation light of appropriate wavelength, or an increase of molar extinction coefficient, or two or more of the above. In a preferable embodiment of the present application, the quantum yield is increased by at least two times; in another preferable embodiment of the present application, the quantum yield is increased by at least 5 to 10 times; in another more preferable embodiment of the present application, the quantum yield is increased by at least 20 to 50 times; in another more preferable embodiment of the present application, the quantum yield is increased by at least 100 to 200 times; in another more preferable embodiment of the present application, the quantum yield is increased by at least 500 to 1,000 times; in another more preferable embodiment of the present application, the quantum yield is increased by at least 1,000 to 10,000 times; in another more preferable embodiment of the present application, the quantum yield is increased by more than 10,000 times; the light source used for exciting the fluorophore to produce fluorescence signals can be any appropriate lighting device, such as LED lamp, incandescent lamp, fluorescent lamp and laser; excitation light can be either emitted directly from these devices or obtained indirectly by means of other fluorophores, such as donor fluorophores of FERT, or donor luminophors of BRET.

Target Molecules

The target molecules of the present application can be any biomaterial or micromolecules, including but not limited to: proteins, nucleic acid (RNA or DNA), lipid molecules, carbohydrates, hormones, cytokines, chemokines, and metabolite metal ions and so on. Target molecules can be molecules associated with diseases or pathogen infection.

In the structure shown in FIG. 1, the inserted nucleotide sequence replaced the stem-loop structures of $N_{19}$, $N_{20}$, $N_{21}$ in FIG. 1 by means of the aptamer molecules in the present application, wherein the nucleotide sequence can specifically identify/bind target molecules. In the absence of target molecules, aptamer molecules do not or weakly bind fluorophore molecules, and thus cannot significantly improve the fluorescence of fluorophore molecules under excitation light of appropriate wavelength; in the presence of target molecules, the binding of target molecules and the nucleotide sequence will promote binding of the aptamer molecules and fluorophore molecules, and thus can significantly improve the fluorescence of fluorophore molecules under excitation light of appropriate wavelength, thereby realizing detection, imaging and quantitative analysis of target molecules.

Target molecules can also be whole cells or molecules expressed on the entire cell surface. Typical cells include but are not limited to cancer cells, bacterial cells, fungal cells and normal animal cells. The target molecules can also be virus particles. At present, many aptamers of the aforementioned target molecules have been identified, and can be integrated into the polyvalent nucleic acid aptamers of the present application. RNA aptamers that have been reported to bind target molecules include but are not limited to: T4 RNA polymerase aptamer, HIV reverse transcriptase aptamer, and phage R17 capsid protein aptamer.

Figure 10:
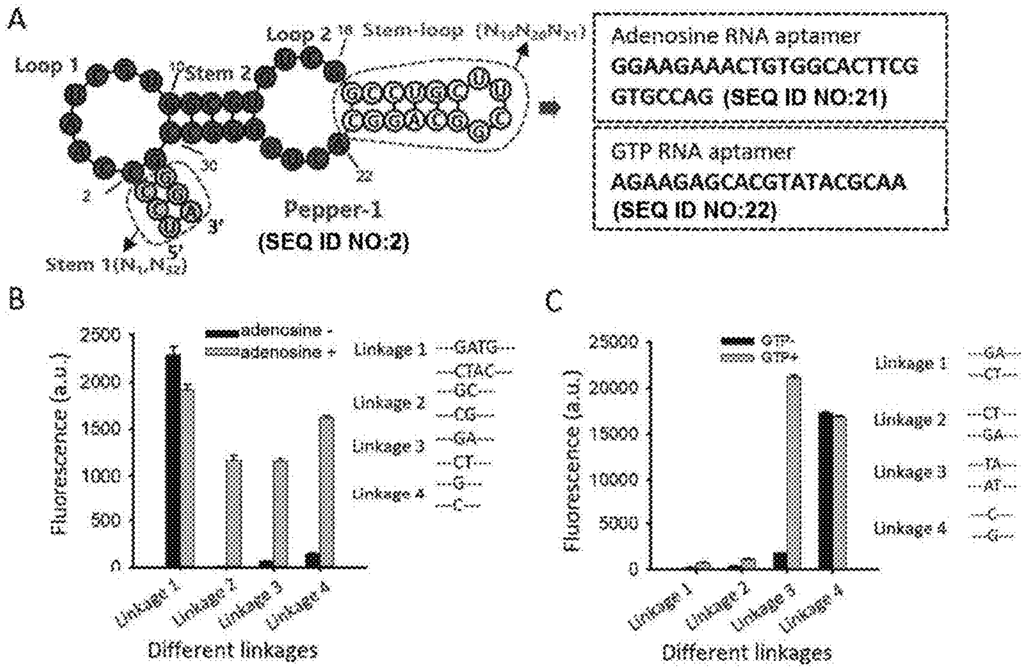
FIG. 10 Probe construction based on Pepper-1. (A) Diagram of probe construction, wherein the stem-loop structure can identify adenosine or GTP; (B) detection effect of adenosine probe; (C) detection effect of GTP probe.

In a preferable embodiment of the present application, the target molecule is adenosine, and the corresponding probe sequence for identifying the target molecule is SEQ ID NO: 21 (as shown in FIG. 10A); in a preferable embodiment of the present application, the target molecule is GTP, and the corresponding probe sequence for identifying the target molecule is SEQ ID NO: 22 (as shown in FIG. 10A).

Objective Nucleic Acid Molecules

"Objective nucleic acid molecules", also called as "target nucleic acid molecules", refer to the nucleic acid molecules to be detected, which can be either intracellular or extracellular; objective nucleic acid molecules include objective RNA molecules and objective DNA molecules. Objective nucleic acid molecules are connected with the nucleic acid aptamer molecules, and are bound to the nucleic acid aptamer molecules via fluorophore molecules so as to significantly improve the fluorescence value of fluorophore molecules under excitation light of appropriate wavelength, thereby detecting the content and distribution of objective nucleic acid molecules.

"Objective RNA molecules" in the present application include any RNA molecule, including but not limited to pre-mRNA, mRNA, pre-rRNA, rRNA, tRNA, hnRNA, snRNA, miRNA, siRNA, shRNA, sgRNA, crRNA, and long non-coding RNA of coding cells per se or exogenous expression products thereof, wherein phage capsid protein MCP identifies the binding sequence MS2RNA, phage capsid protein PCP identifies the binding sequence PP7RNA, X phage transcription termination protein N identifies the binding sequence boxB RNA or the like. Target RNA can be fused at 5' end or 3' end or the position of $N_{19}$-$N_{20}$-$N_{21}$ of the RNA aptamer molecules of the present application.

"sgRNA" in the present application refers to single guide RNA (single guide RNA, sgRNA) formed by modifying tracrRNA and crRNA in the CRISPR/Cas9 system, wherein the sequence of about 20 nt at the 5' end of the system targets DNA site via base pair complementation, and promotes the Cas9 protein to induce DNA double-strand break at this site.

Concatemers of Nucleic Acid Aptamer

The nucleic acid aptamer molecules of the present application may further include concatemers that can bind multiple fluorophore molecules. The concatemers are connected by spacer sequences of appropriate length, and the number of Pepper structures in series may be 2, 3, 4, 5, 6, 7, 8, 9, 10 or greater. The concatermers may be in many forms. In a preferable embodiment of the present application, the series form is "Series 1", as shown in FIG. 6A, and a preferable nucleotide sequence is SEQ ID NO: 8, 9, 10, 11 or 12, wherein 2Pepper-5 indicates Concatemer 1 with 2 Pepper-5 structures; in another preferable embodiment of the present application, the series form is "Series 2", as shown in FIG. 6B, and a preferable nucleotide sequence is SEQ ID NO: 13, 14, 15 or 16, wherein 2×Pepper-6 indicates Concatemer 2 with 2 Pepper-6 structures; in another preferable embodiment of the present application, the series form is "Series 3", as shown in FIG. 6C, and a preferable nucleotide sequence is SEQ ID NO: 17, 18 or 19, wherein 2×2Pepper-5 indicates Concatemer 3 with 4 Pepper-5 structures; in any form, the spacer sequences between the concatemers can be changed.

The monomer aptamers of the present application refer to aptamers containing only one Pepper structure, that is, the aptamers containing two stem structures, two loop structures and one stem-loop structure (FIG. 1A).

Figure 6:
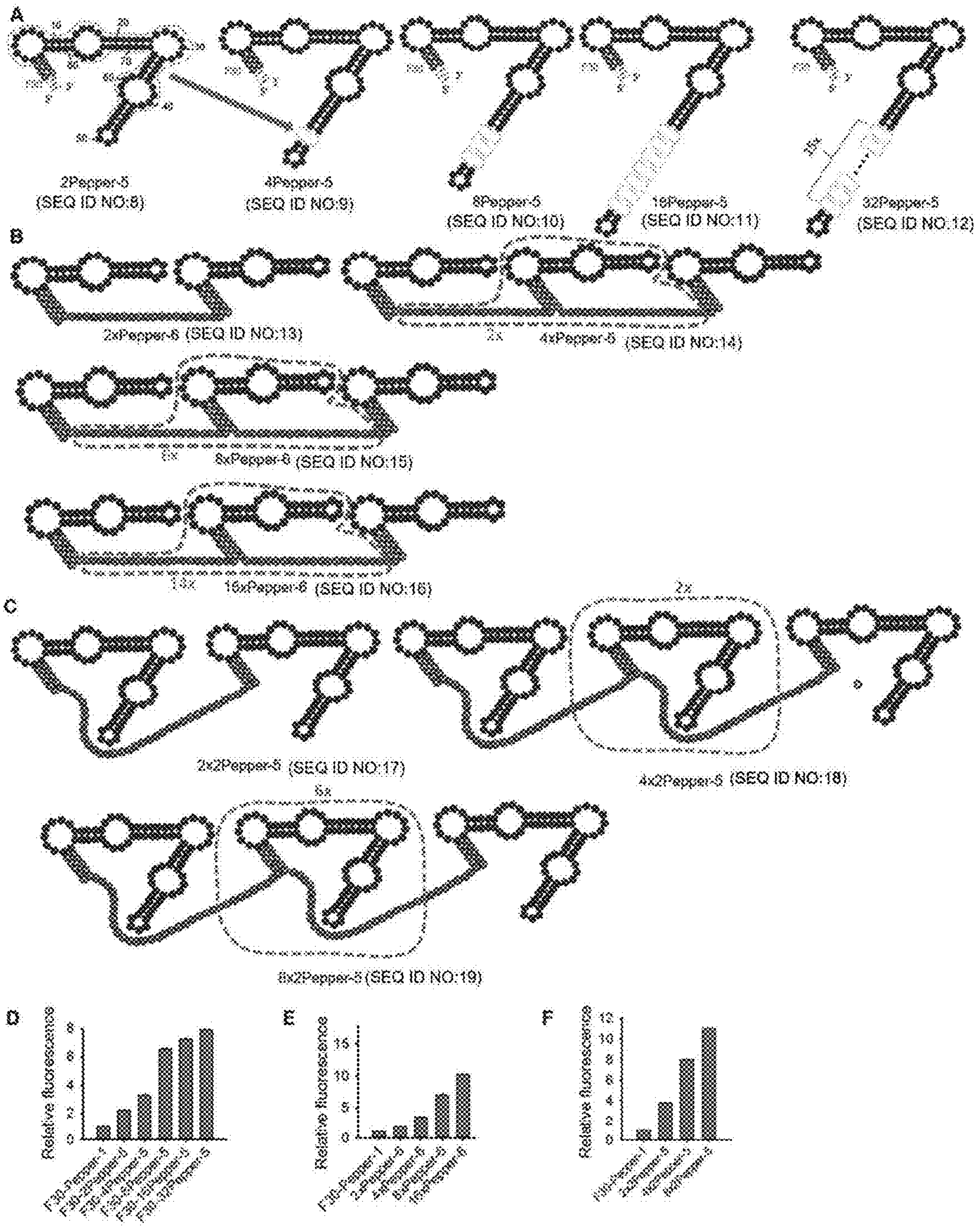
FIG. 6 Activation effects of different Pepper concatemers on III-3. (A) Obtaining Pepper concatemers in a way of "Tandem 1"; (B) obtaining Pepper concatemers in a way of "Tandem 2"; (C) obtaining Pepper concatemers in a way of "Tandem 3"; (D) activation effects of different Pepper concatemers obtained in the way of "Tandem 1" on III-3; (E) activation effects of different Pepper concatemers obtained in the way of "Tandem 2" on III-3; (F) activation effects of different Pepper concatemers obtained in the way of "Tandem 3" on III-3.

The polymer aptamers refer to aptamers containing more than one Pepper structure, including but not limited to the aptamer composed of several series forms as shown in FIG. 6.

Aptamer-Fluorophore Complex

The aptamer-fluorophore complex of the present application contains one nucleic acid aptamer molecule and one or more fluorophore molecules. In an embodiment of the present application, the molecule complex containing one nucleic acid molecule and one fluorophore molecule is F30-Pepper-2-III-3, F30-Pepper-2-III-7, F30-Pepper-2-III-6, F30-Pepper-2-III-8, F30-Pepper-2-III-4, F30-Pepper-2-III-15, F30-Pepper-2-III-18 and F30-Pepper-2-III-21.

In another embodiment of the present application, nucleic acid molecules of the concatemer and a plurality of fluorophore molecules forms a complex, for instance, a complex 8Pepper-5-8×(III-3) formed in the way of "Series 1" by F30-8Pepper-5 containing 8 aptamer units and 8 fluorophore molecules, namely, III-3, 8Pepper-5-8×(III-7), 8Pepper-5-8×(III-6), 8Pepper-5-8×(III-8), 8Pepper-5-8×(II-4), 8Pepper-5-8×(II-15), 8Pepper-5-8×(III-18) and 8Pepper-5-8×(III-21). The molecule complexes may exist in vitro in the form of two separate solutions, or in the same solution, or in cells.

Nucleic Acid Aptamer Function

The aptamer function of the present application means to significantly enhance fluorescence intensity of fluorophore molecules under excitation light of appropriate wavelength, and aptamers can be detected by function detection of nucleic acid aptamer as shown in common Experimental Method (V) in the embodiments. In a preferable embodiment of the present application, the fluorescence intensity is increased by at least two times (the fluorescence intensity is detected according to the Experimental Method (V)); in another preferable embodiment of the present application, the fluorescence intensity is increased by at least 5 to 10 times; in another more preferable embodiment of the present application, the fluorescence intensity is increased by at least 20 to 50 times; in another more preferable embodiment of the present application, the fluorescence intensity is increased by at least 100 to 200 times; in another more preferable embodiment of the present application, the fluorescence intensity is increased by at least 500 to 1,000 times; in another more preferable embodiment of the present application, the fluorescence intensity is increased by at least 1,000 to 10,000 times; in another more preferable embodiment of the present application, the fluorescence intensity is increased by more than 10,000 times.

Secondary Structure of Nucleic Acid Aptamers

In the present application, the secondary structure of nucleic acid aptamers is obtained by simulation and prediction using mFold online analysis software (http://unafold.rna.albany.edu/?q=mfold). The stem structure in the secondary structure refers to a local double-strand structure formed by complementary pairing of hydrogen bonds in some regions of the single strand of nucleic acid aptamer molecules. In general, the formation of the double-strand structure does not require complementary pairing of all nucleotides in this region; in general, the stem structure will be formed when complementary pairing occurs between at least 50% of the nucleotides in a fragment of sequences $N_1$ and $N_{32}$, as well as $N_{19}$ and $N_{21}$ and the other fragment. If $N_1$ and $N_{32}$ are single nucleotides, the stem structure can be formed with complete complement of $N_1$ and $N_{32}$ (as shown in FIG. 1).

DNA Molecules Expressing Nucleic Acid Aptamers

The DNA molecules contain a DNA sequence which can encode the nucleic acid aptamer molecules of the present application. The DNA molecules contain a nucleotide sequence $R_1$CCAATCGTGGCGTGTCG$R_{19}$-$R_{20}$-$R_{21}$ACTGGCGCCG$N_{32}$, set forth by SEQ ID NO: 74, as well as a nucleotide sequence with identity of at least 70%, wherein $R_1$ encodes $N_1$ in the General Formula Pepper structure, $R_{19}$ encodes $N_{19}$ in the General Formula Pepper structure, $R_{20}$ encodes $N_{20}$ in the General Formula Pepper structure, $R_{21}$ encodes $N_{21}$ in the General Formula Pepper structure, and $R_{32}$ encodes $N_{32}$ in the General Formula Pepper structure. The DNA molecules may also contain a promoter which controls DNA transcription, wherein the promoter is in operable connection to the DNA sequence encoding the nucleic acid aptamer. In an embodiment of the present application, the DNA molecule contains an U6 promoter; in another embodiment of the present application, the DNA molecules contain a CMV promoter. The DNA molecules may further contain a DNA sequence which encodes any objective nucleic acid molecule. In an embodiment of the present application, the DNA molecules encoding the objective RNA contain a DNA sequence (sequences for embedding RNA are respectively SEQ ID No: 24, 25) encoding glyceraldehyde-3-phosphate dehydrogenase (GAPDH) and transmembrane emp24 domain-containing protein 2 (TMED2). In another embodiment of the present application, the DNA molecules encoding the objective RNA contain a DNA sequence (sequences for embedding RNA are respectively SEQ ID No: 26, 27) encoding mCherry and TagBFP.

Promoters

"Promoters" in the present application include promoters of eukaryotic and prokaryotic cells. Promoter sequences of eukaryotic cells are totally different from those of prokaryotic cells. Generally, eukaryotic promoters cannot be identified by RNA polymerases in prokaryotic cells or mediate RNA transcription. Similarly, prokaryotic promoters cannot be identified by RNA polymerases in eukaryotic cells or mediate RNA transcription either. The strength of different promoters varies greatly (strength refers to the ability to mediate transcription). According to actual application, strong promoters can be used for achieving high level transcription. For instance, high level expression is better for labeling, and, for evaluation of transcription behavior, lower level transcription will allow cells to process transcription in a timely manner. One or more suitable promoters can be selected for different host cells. For instance, being used in *Escherichia coli* cells, T7 phage promoter, lac promoter, trp promoter, recA promoter, ribosome RNA promoter, PR and PL promoters in X phage, and other promoters, but not limited to: lacUV5 promoter, ompF promoter, bla promoter, lpp promoter etc. Moreover, a hybrid trp-lacUV5 promoter (tac promoter) or other *Escherichia coli* cells obtained through recombinant or synthetic DNA technology can all be used for transcribing the RNA aptamers of the present application. Some of the operator sequences in bacteria per se can combine with promoter sequences to form inducible promoters, and specific inducers need to be added at this moment to induce transcription of DNA molecules. For instance, the expression of lac operator needs to be induced by the addition of lactose or lactose analogues (IPTG), other operators including trp, pro or the like.

As mentioned above, the regulating sequence of 5' end of DNA molecule decoding sequence is promoters. Suitable promoters need to be selected according to the promoter intensity either to obtain RNA apatmers via in vitro transcription or to express aptamers in cultured cells or tissues. Since the expression of aptamers in vivo can be genetically manipulated, another type of promoters is inducible promoters that induce DNA transcription in response to a specific environment, such as in a specific tissue, at a specific time, and in a specific developmental stage. These different promoters can be identified by RNA polymerase I, II or III.

Promotion of transcription in eukaryotic cells also needs suitable promoters, including but not limited to β-globulin promoter, CAG promoter, GAPDH promoter, β-actin promoter, actin promoter, Cstf2t promoter, SV40 promoter, PGK promoter, MMTV promoter, adenovirus Ela promoter, CMV promoter and so on. Termination of transcription in eukaryotic cells depends on the specific cleavage site in RNA sequence. Similarly, since the transcription genes of RNA polymerase are different, transcriptional terminators also vary significantly. However, those skilled in the art can realize screening of suitable 3' transcriptional terminator sub-regions by means of routine experimental skills.

Expression System

The "expression system" of the present application, also called as "expression vector", contains and is integrated with DNA molecules expressing nucleic acid aptamer. The expression system of the present application can be a plasmid or a virus particle.

Recombinant virus of "expression vector" can be obtained by transfection of plasmids into viral-infected cells. Suitable vectors include but are not limited to virus vectors such as a, vector system gt11, gt WES.tB, Charon 4, and plasmid vectors include pBR322, pBR325, pACYC177, pACYC184, pUC8, pUC9, pUC18, pUC19, pLG399, pR290, pKC37, pKC101, pBluescript II SK+/− or KS+/− (see Stratagene cloning system), pET28 series, pACYC-Duet1, pCDFDuet1, pRSET series, pBAD series, pQE, pIH821, pGEX, pIIIEx426 RPR and so on.

A large number of host expression systems can be used for expressing the DNA molecules of the present application. Mostly, the vector system has to be compatible to the host cells in use, wherein the host vector system includes but is not limited to: transformed phage DNA, or plasmid DNA, or bacteria with cosmid DNA; yeast containing yeast vector; mammalian cells infected with a virus (e.g. adenovirus, adeno-associated virus, retrovirus); insect cells infected with a virus (e.g. baculovirus); and plant cells infected with bacteria or transformed by means of particle bombardment. Expression elements in the vectors are significantly different in strength and characteristics. Any one or more suitable transcription elements can be selected according to the host-vector system in use.

Once the constructed DNA molecules are cloned into the vector system, it will be easy to transfer them into host cells. Based on different vector or host cell systems, the method includes but is not limited to transformation, transduction, conjugation, fixation, electrical transfer or the like.

An embodiment of the present application provides expression plasmids pET28a-T7-F30-Pepper-2, pLKO.1-F30-Pepper-2 and pYES2.1-F30-Pepper-2 containing DNA molecules for encoding F30-Pepper-2 RNA. Another embodiment of the present application provides expression plasmid pLKO.1-F30-8Pepper-5 containing DNA molecules for encoding F30-8Pepper-5 RNA. Another embodiment of the present application provides expression plasmids pCDNA3.1 hygro(+)-BFP-4Pepper-7, pCDNA3.1 hygro(+)-mCherry-4Pepper-7, pCDNA3.1 hygro(+)-GAPDH-4Pepper-7 and pCDNA3.1 hygro(+)-TMED2-4Pepper-7 containing DNA molecules for encoding BFP-4Pepper-7, mCherry-4Pepper-7, GAPDH-4Pepper-7 and TMED2-4Pepper-7. Another embodiment of the present application provides expression plasmids psgRNA-Pepper-8 (loop 1), psgRNA-Pepper-8 (tetraloop) and psgRNA-Pepper-8 (loop 1 and tetraloop) containing DNA molecules for encoding sgRNA-Pepper-8 (loop 1), sgRNA-Pepper-8 (tetraloop), sgRNA-Pepper-8 (loop 1 and tetraloop). Another embodiment of the present application provides an expression plasmid pLKO.1-4Pepper-9-MS2 containing DNA molecules for encoding 4Pepper-9-MS2.

The present application further provides expression vectors integrated with DNA molecules for encoding nucleic acid aptamers, but with vacant encoding DNA sequences of objective RNA molecules, wherein the vacancy of encoding DNA sequences of objective RNA molecules allows the users to choose DNA sequences of objective RNA molecules to be detected, for instance, corresponding encoding DNA sequence of GAPDH mRNA inserts the DNA sequence into the expression vector of the present application by means of standard recombination DNA technology, and guides the obtained expression vector into the host cells of (transfection, transform, infection and so on), thereby detecting the content and distribution of objective RNA.

Host Cells

"Host cells" in the present application include but are not limited to bacteria, yeast, mammalian cells, insect cells, plant cells, zebra fish cells, fruit fly cells, and nematode cells. Host cells preferably are cultured cells in vitro or whole in vivo living tissue. Mammalian cells contained in the host cells of the present application include but are not limited to 297T, COS-7, BHK, CHO, HEK293, HeLa, H1299, stem cells of fertilized eggs, inducible totipotent stem cell, and primary cells isolated directly from mammalian tissues and so on; *Escherichia coli* cells contained therein include but are not limited to BL21 (DE3), BL21 (DE3, Star), TOP10, Mach1, and DH5a; and yeast cells contained therein include but are not limited to BY4741, BY4742, and AH109.

Detection Array

The detection array of the present application includes one or more nucleic acid aptamer molecules of the present application, wherein the nucleic acid aptamer molecules are anchored at discrete locations on the array surface composed of solid supports, including but not limited to glass, metals, and ceramic and so on. The nucleic acid aptamer molecules of the present application can be anchored to the array surface by, but not limited to, the following methods: (1) labeling the 5' end or 3' end of the nucleic acid aptamer molecule with biotin, coating the array surface with streptavidin, and anchoring the nucleic acid aptamer molecule by specific binding of biotin and streptavidin; (2) identifying the binding sequence MS2 by using the phage capsid protein MCP, identifying the biding sequence PP7 by using the phage capsid protein PCP or identifying the binding sequence boxB by using the λ phase transcription terminating protein N, fusing the RNA sequence at the 5', 3' or stem-loop structure of the nucleic acid aptamer molecules, coating the array surface with protein MCP, PP7 or $\lambda_N$ protein identified and bound thereby, and anchoring the nucleic acid aptamer molecules through the specific effects of MS2 with MCP protein, PP7 with PCP protein or boxB RNA with $X_N$ protein; (3) fusing a fragment of RNA or DNA sequence at the 5' end or 3' end of the nucleic acid aptamer molecules, anchoring an RNA sequence in complementary pairing with the RNA sequence segment or an DNA sequence in complementary pairing with the DNA sequence segment on the array surface, and anchoring the nucleic acid aptamer molecules on the array surface by means of the molecular hybridization principle. The detection array can be used for detecting the presence or absence of the target molecule as well as the concentration level, as a result, the nucleic acid aptamer molecules be bound with the fluorophore molecules and significantly improve the fluorescence intensity under excitation light of appropriate wavelength only with the presence of target molecules; and, within a certain range, the higher the concentration of the target molecules, the higher the fluorescence intensity.

Kit

Kit of the present application includes the nucleic acid aptamer molecules and/or the fluorophore molecules of the present application, and corresponding instructions; or includes an expression system for expressing the nucleic acid aptamer molecules and/or the fluorophore molecules, and corresponding instructions; or includes host cells expressing the aptamer molecular expression system and/or the fluorophore molecules, and corresponding instructions. The nucleic acid aptamer molecules and the fluorophore molecules in the kits respectively exist in individual solutions, or exist in the same solution.

The present application will be further elaborated in the following examples, which are merely used for giving examples, rather than limiting the scope of the present application. The examples mainly adopt conventional cloning methods of molecular biology in genetic engineering, which are well known to ordinary technicians in this field, for instance, relevant chapters from *Lab Ref: A Handbook of Recipes, Reagents, and Other Reference Tools for Use at the Bench* by Jane Roskams et al, and *Molecular Cloning—A Laboratory Manual* (Third Edition, August 2002, Science Press, Beijing) written by Sambrook. J, D. W. Russell and translated by Peitang HUANG et al. Based on the following examples, it easy for one skilled in the art to successfully implement the present application after slight amendment and change made according to actual situations.

In the examples, the pCDNA3.1 hygro (+) plasmid vector was purchased from Invitrogen Company, pLKO.1-puro plasmid vector was purchased from Sigma Company, pET28a plasmid vector was purchased from Novagen Company, pYES2.1 TOPO TA plasmid vector was purchased from Invitrogen. All primers used for PCR were synthesized, purified and identified correct via mass spectrometry by Shanghai Generay Biotech Co., Ltd. Expression plasmids constructed in the examples all went through the sequence determination accomplished by JIE LI BIOLOGY. Taq DNA polymerase used in all examples was purchased from Yeasen Biotechnology (Shanghai) Co., Ltd., PrimeSTAR DNA polymerase was purchased from TaKaRa Company, and corresponding polymerase buffers and dNTP were included during purchasing of these three kinds of polymerases. EcoRI, BamHI, BglII, HindIII, NdeI, XhoI, SacI, XbaI, SpeI and other restriction endonuclease, T4 ligase, T4 phosphorylase (T4 PNK), and T7 RNA polymerase were purchased from Fermentas company, and corresponding polymerase buffers and so on were included during purchasing. Hieff Clone™ One Step cloning kits used in the examples were purchased from Yeasen Biotechnology (Shanghai) Co., Ltd. Unless otherwise stated, chemical reagents such as inorganic salts were all purchased from Shanghai Chemical Reagent Company of Sinopharm. Kanamycin was purchased from Ameresco Company; Amp was purchased from Ameresco Company; and 384-well and 96-well fluorescence detection blackboard was purchased from Grenier Company. DFHBI-1T and DFHO were purchased form Lucerna Company. GTP and SAM were purchased from Sigma Company.

DNA purification kits used in the examples were purchased from BBI Company (Canada), ordinary plasmid micro extraction kits were purchased from Tiangen Biotech (Beijing) Co., Ltd. BL21 (DE3, Star) bacterial strains were purchased from Invitrogen Company. 293T/17 cells and COS-7 cells were purchased from Cell Bank of Committee of Typical Culture Collection, Chinese Academy of Sciences. BY4741 yeast strain was purchased from Shanghai Weidi Biotechnology Co., Ltd.

Main instruments used in the examples: Synergy Neo2 Multiscan Spectrum (Bio-Tek Company of America), X-15R high speed freezing centrifuge (Beckman Company of America), Microfuge22R tabletop high speed freezing centrifuge (Beckman Company of America), PCR amplifier (Biometra Company of German), in vivo imaging system (Kodak Company of America), photometer (Wako Company of Japan), nucleic acid electrophoresis apparatus (Shenneng Bocai Company).

Meanings of abbreviations are as follows: "h" refers to hours, "min" refers to minutes, "s" refers to seconds, "d" refers to days, "μL" refers to micro-liters, "ml" refers to milliliters, "L" refers to liters, "bp" refers to base pairs, "mM" refers to millimoles, and "μM" refers to micromoles.

Commonly Used Experimental Methods and Materials in the Examples

1. Preparation of Nucleic Acid Aptamer

The cDNA corresponding to the RNA to be detected was amplified using primers containing T7 promoter, and the RNA was transcribed using T7 RNA polymerase (purchased from Fermentas) using the double-stranded cDNA as the template. 10 μL 3 M NaAc, 115 μL DEPC water were added into the 20 μL transcription system and mixed well. Then 150 μL phenol-chloroform-isopropanol mixture (phenol:chloroform:isopropanol=25:24:1) was added and shaken to mix well. The mixture was centrifugated at 10,000 rpm for 5 min, and the supernatant was taken. An equal volume of chloroform solution was added into the supernatant, shaken, mixed, centrifugated at 10,000 rpm for 5 min. The supernatant was taken and the same procedure was repeated once again. 2.5 times the volume of absolute ethanol was added into the supernatant and mixed. The mixture was placed in a refrigerator at −20° C. for 30 min, and centrifugated at 12000 rpm at 4° C. for 5 min. The supernatant was discarded and the precipitate was washed twice with pre-cooled 75% ethanol. After the ethanol was evaporated, an appropriate amount of screening buffer was added to resuspend the pellet. The solution was treated at 75° C. for 5 minutes and placed at room temperature for more than 10 minutes for subsequent experiments.

2. Cell Culture and Transfection

All the cells in this example were cultured in DMEM (high glucose) supplemented with 10% FBS, streptomycin and penicillin in a CO2 incubator. All cell lines were split at a confluence of 80-90%. The FuGENE®HD (purchased from Promega) was used for transfection according to the instructions.

3. Fluorescence Imaging

The main imaging experiments in the examples were carried out using a Leica SP8 confocal laser scanning microscope equipped with a HCXPL APO 63.0×1.47 OIL objective, and a HyD detector. A 488 nm laser was used to image the fluorescence of Pepper-III-3 complex. A 405 nm and a 561 nm laser were used to image the fluorescence of BFP and mCherry, respectively. A 458 nm laser, a 458 nm laser, a 488 nm laser, a 488 nm laser, a 488 nm laser, a 561 nm laser and a 561 nm laser were used to image the fluorescence of Pepper-III-7, Pepper-III-6, Pepper-III-8, Pepper-III-4, Pepper-III-15, Pepper-III-18 and Pepper-III-21, respectively. A 448 nm laser was used to image the fluorescence of Broccoli-DFHBI-1T and Corn-DFHO.

4. Homologous Recombination-Based Construction of Recombinant Plasmids (1) Preparation of linearized vector: select a suitable cloning site and linearize the vector by restriction enzyme-based digestion or inverse PCR amplification.
(2) PCR amplification of the insertion fragments: use the forward and reverse PCR primers containing 15-25 bp (excluding restriction site) homologous sequence of the linearized vector to amplify the template to obtain insertion fragment harboring the identical sequences corresponding to the two ends of the linearized vector.
(3) Determination of the concentrations of linearized vector and insertion fragment: dilute the linearized vector and insertion fragment, take 1 μL of the original solution and diluted solution to perform agarose gel electrophoresis, determine the concentration of the fragments by comparing the intensities of the bands to those of the DNA molecular weight standard (DNA maker).
(4) Recombination reaction: the optimal amount of vector used in the recombination reaction system is 0.03 pmol; the optimal molar ratio of linearized vector to insertion fragment is 1:2-1:3, i.e., the optimal amount of insertion fragment is 0.06-0.09 pmol.

| Component | Recombination reaction |
|---|---|
| $ddH_2O$ | Maximum to 20 μL |
| 2 × Hieff Clone Enzyme Premix (from Yeasen) | 10 μL |
| linearized vector | X μL |
| insertion fragment | Y μL |

X and Y are calculated according to the formula to obtain the linearized vector and insert fragment. After the preparation of the system, mix the components and place at 50° C. for 20 min. When the insertion fragment>5 kb, the incubation temperature can be extended to 25 min. After the reaction is complete, it is recommended to cool the reaction tube on ice for 5 min. The reaction product can be transformed directly, or stored at −20° C. before transformation needed.

5. Characterization of the Aptamers

Preparation of Pepper or Pepper mutant aptamer according to the commonly used experimental method (1). 5 μM aptamer and 1 μM fluorophore were incubated in the detection buffer (40 mM HEPES, pH 7.4, 125 mM KCl, 5 mM MgCl2, 5% DMSO). The maximal excitation and emission peaks of the aptamer-fluorophore complexes were determined using a Synergy Neo2 multifunctional microplate reader. The fluorescence intensities of the aptamer-fluorophore complexes at the maximal excitation and emission peaks were determined using a Synergy Neo2 multifunctional microplate reader. The control sample (1 μM fluorophore without aptamer) was also measured under the same conditions. Then the ratios of fluorescence intensity were calculated. For example, the fluorescence maximal excitation and emission peaks of the complex of 5 μM F30-Pepper-2 and 1 μM III-3 fluorophore are 485 nm and 530 nm, respectively. The fluorescence intensity of the complex at 485±10 nm excitation and 530 nm±10 nm emission was 36,000, the fluorescence intensity of the control sample (1 μM III-3 fluorophore only) under the same detection conditions was 10. Thus, the activation ratio of F30-Pepper-2 aptamer on III-3 fluorophore was 3,600-fold.

Example 1. The Secondary Structure of Pepper Aptamer

The secondary structure of Pepper aptamer was analyzed using the mFold online RNA structure analysis software. Pepper contains two stems, two loops and one stem-loop structures (FIG. 1A). For one of the stem 1 and stem-loop, the predicted secondary structure of Pepper-1 (SEQ ID NO: 1) was shown in FIG. 1B.

Example 2. Characterization of Pepper-III-3 Complex

Figure 4:
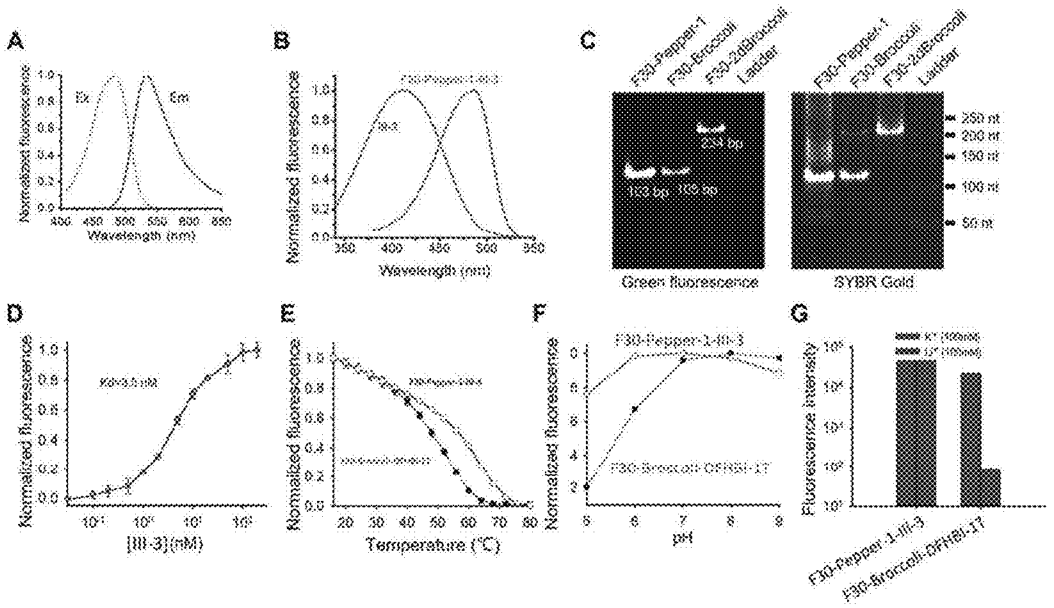
FIG. 4 Nature identification of F30-Pepper-1-III-3 complex. (A) Fluorescence excitation spectrum and emission spectrum of F30-Pepper-1-III-3 complex; (B) absorption spectra of F30-Pepper-1-III-3 complex and III-3; (C) oligomerization identification of F30-Pepper-1-III-3 complex; the "ruler" is a single-stranded DNA standard used for calibrating size of the aptamer; (D) dissociation constant determination of the binding of F30-Pepper-1 to 11-3; (E) temperature stability determination of F30-Pepper-1-III-3 complex; (F) pH stability determination of F30-Pepper-1-III-3 complex; (G) determination of dependence of F30-Pepper-1-III-3 complex on K+.

In order to detect the spectral properties of the Pepper-III-3 complex, F30-Pepper-1 (SEQ ID NO: 2) RNA was prepared according to the commonly used experimental method (1). 1 μM III-3 with 5 μM F30-Pepper-1 was incubated. The results showed that the maximum excitation and emission of the F30-Pepper-1-III-3 complex were 485 nm, and 530 nm, respectively (FIG. 4A). In order to detect the absorption difference between F30-Pepper-1III-3 complex and III-3 fluorophore itself, the absorption of F30-Pepper-1 and III-3 complex (5 μM III-3 and 25 μM F30-Pepper-1) or 5 μM alone III-3 was detected. The results showed that the maximum absorption of F30-Pepper-1-JII-3 complex has a large red shift relative to III-3 itself, and the maximum light absorption is 484 nm (FIG. 4B).

In order to detect whether Pepper binds to III-3 in the form of monomer or polymer, F30-Pepper-1 was identified by the Native PAGE using the monomeric F30-Broccoli (SEQ ID NO: 4) and F30-2dBroccoli (SEQ ID NO: 5) (Filonov et al. Journal of the American Chemical Society 2014. 136: 16299-16308; Filonov et al. Chemistry & biology 2015. 22: 649-660) as the controls. The fluorescence imaging result was compared with the staining result by SYBR Gold (universal nucleic acid dye that was purchased from Invitrogen). The results showed that F30-Pepper-1 was located at about 100 bp similar to F30-Broccoli, which was consistent with its actual size of 103 bp. Therefore, the results indicate that F30-Pepper-1 binds to III-3 in the form of monomer (FIG. 4C).

In order to detect the binding constant of Pepper and III-3, 2 nM F30-Pepper-1 was incubated with different concentrations of III-3 and their fluorescence was determined. The results showed that the binding constant of F30-Pepper-1 and II-3 was 3.5 nM (FIG. 4D).

In order to test the thermostability of Pepper, 10 μM III-3 was incubated with 1 μM F30-Pepper-1, and then was placed at different temperatures for 5 minutes before the fluorescence was determined. 10 μM DFHBI-1T was incubated with 1 μM F30-Broccoli to be as the control. The results showed that the $T_m$ of F30-Pepper-1 is 55° C., which is significantly higher than the 48° C. of F30-Broccoli (FIG. 4E), indicating that F30-Pepper-1 has better thermostability.

In order to test the stability of Pepper-III-3 complex at different pH, F30-Pepper-1-II-3 complex was incubated in different pH environment for 60 min before the fluorescence was detected. The F30-Broccoli-DFHBI-1T complex was used as the control. The results showed that the F30-Pepper-1-II-3 complex maintained a high fluorescence in the range of pH 5-9, while the fluorescence of F30-Broccoli-DFHBI-1T decreased rapidly with the decrease of pH (FIG. 4F), indicating that the F30-Pepper-1-III-3 complex has better pH stability.

In order to detect the dependence of Pepper-III-3 complex on $K^+$, 1 μM F30-Pepper-1 and 5 μM III-3 were incubated in buffer containing 100 mM KCl or 100 mM LiCl, respectively. The solution was treated at 70° C.5 for 5 min and placed at room temperature for more than 15 min before the fluorescence was detected. The F30-Broccoli-DFHBI-1T complex was used as the control. Previous studies have shown that the structure of Broccoli contains a G-quadruplex, and the stability of the G-quadruplex structure is highly dependent on $K^+$, which was consistent with the results. The fluorescence of F30-Broccoli-DFHBI-1T complex in LiCl buffer was a few percent of that in KCl buffer (FIG. 4G). In comparison, the fluorescence of the F30-Pepper-1-III-3 complex did not depend on $K^+$ (FIG. 4G), indicating that Pepper does not contain G-quadruplex on its structure.

Example 3. Fluorescence Activation of III-3 Fluorophore by Different Pepper Mutants In order to detect the fluorescence activation of III-3 fluorophore by different Pepper mutant, the Pepper-1 sequence in F30-Pepper-1 was mutated according to Table 1. The Pepper RNA containing different mutations were prepared according to the commonly used experimental method (1). 1 μM III-3 was incubated with 5 M RNA and their fluorescence activation folds were determined according to the commonly used experimental method (5). The results showed that most of the F30-Pepper-1 mutants containing single mutation retained a strong fluorescence activation of III-3 (>10 times) (Table 2). several F30-Pepper-1 mutants containing 2-7 mutations still retained strong fluorescence activation of III-3 (>100 times) (Table 3). In summary, many Pepper mutants containing single and multiple mutants still retain the ability to activate the fluorescence of III-3 fluorophore.

TABLE 2

Activation of III-3 by Pepper mutants with single mutation

| Mutant | Activation folds | Mutant | Activation folds | Mutant | Activation folds |
|---|---|---|---|---|---|
| F30-Pepper-1 | 3600 | G10A | 847 | G18C | 1028 |
| C3G | 360 | G10C | 856 | A22U | 87 |
| C3A | 2484 | G11U | 1512 | A22G | 687 |
| C3U | 2016 | G11A | 1526 | A22C | 147 |
| A4U | 1836 | G11C | 325 | C23G | 65 |
| A4G | 2160 | C12G | 2125 | C23A | 547 |
| A4C | 2772 | C12A | 458 | G26U | 532 |
| A5G | 1800 | C12U | 2268 | C27G | 1875 |
| A5C | 2628 | G13U | 587 | C27A | 186 |
| U6A | 1872 | G13A | 792 | C27U | 3158 |
| U6G | 1980 | G13C | 1758 | G28U | 873 |
| U6C | 2088 | U14A | 1524 | G28A | 42 |
| C7A | 1044 | U14G | 3152 | G28C | 145 |
| C7U | 2268 | G15C | 15 | C29G | 2145 |

TABLE 2-continued

| Activation of III-3 by Pepper mutants with single mutation | | | | | |
|---|---|---|---|---|---|
| Mutant | Activation folds | Mutant | Activation folds | Mutant | Activation folds |
| G8C | 3168 | U16A | 28 | C29U | 1437 |
| G8A | 324 | U16G | 125 | C29A | 18 |
| U9A | 2124 | C17A | 52 | C30G | 145 |
| U9C | 72 | C17U | 1268 | C30U | 2587 |
| G10U | 900 | G18U | 1024 | C30A | 1596 |

Note:
F30-Pepper-1 in Table 2 is an aptamer with the sequence of SEQ ID NO:2.
Other aptamers are generated by mutating the corresponding nucleotide in FIG. 1A within the Pepper-1 sequence in F30-Pepper-1.

TABLE 3

| Activation of III-3 by Pepper mutants with multiple mutations | | | | | |
|---|---|---|---|---|---|
| Mutant | Activation folds | Mutant | Activation folds | Mutant | Activation folds |
| F30-Pepper-1 | 3600 | U9A/C27U | 478 | C17U/C29U | 125 |
| C2G/G31C | 3124 | U9A/C27G | 178 | C17U/C30U | 578 |
| C2U/G31A | 3256 | U9A/C27A | 17 | C17U/C30A | 268 |
| C2A/G31U | 3365 | G13C/C17U | 87 | C17U/C27U | 689 |
| G10A/C30U | 3147 | U14A/C17U | 256 | C17U/C27G | 876 |
| G10C/C30G | 3514 | U14G/C17U | 145 | G18U/C29G | 148 |
| G10U/C30A | 3254 | G11U/C17U | 478 | G18U/C27G | 547 |
| A5G/U6C | 500 | C12G/C30U | 445 | G18U/C27U | 789 |
| A5C/C7U | 368 | C12A/C29G | 14 | G18U/C30U | 698 |
| U6A/C27G | 457 | G11A/C29U | 456 | G18U/C30A | 789 |
| U6G/C27U | 880 | G11C/C29U | 15 | A22G/C30U | 157 |
| U6C/C27U | 758 | C12U/C30U | 568 | C23A/C29G | 78 |
| C7A/C29G | 245 | G13U/C17U | 125 | G26U/C27U | 89 |
| C7U/C29G | 356 | G13C/C17U | 87 | C27G/C29G | 1025 |
| G8C/C29G | 268 | U14A/C17U | 256 | C27G/C30U | 1278 |
| U9A/C30U | 248 | U13G/C16U | 145 | C27G/C30A | 785 |
| U9A/C30A | 356 | C17U/C29G | 457 | C27U/C29G | 1457 |
| C27U/C30U | 786 | C29G/C30U | 1203 | C29U/C30A | 536 |
| G28U/C29G | 99 | C29G/C30A | 986 | U6C/G8C/C2 | 256 |
| G28U/C30U | 125 | C29U/C30U | 487 | U9A/U14G/C | 258 |
| C2G/G31C/ A5G/U6C | 256 | C21U/C30U/ C17U/C27G | 324 | C2G/G31C/ G10U/C30A/ U6G/C27U | 652 |
| G10A/C30U/ C17U/C27U | 68 | C2U/G31A/ C27G/C29G | 126 | C2U/G31A/ G10A/C30U/ U6G/C27U | 458 |
| G10A/C30U/ C17U/C27U | 126 | C2U/G31A/ C12U/C30U | 245 | C2U/G31A/ G10C/C30G/ U6G/C27U | 796 |
| G10C/C30G/ U9A/C27U | 234 | C2A/G31U/ U6G/C27U | 158 | C2U/G31A/ G10U/C30A/ U6G/C27U | 564 |
| G10C/C30G/ U6G/C27U | 257 | C2A/G31U/ C12U/C30U | 59 | C2A/G31U/ G10A/C30U/ U6G/C27U | 358 |
| G10U/C30A/ C17U/C27U | 156 | C2U/G31A/ G10U/C30A | 2583 | C2A/G31U/ G10C/C30G/ U6G/C27U | 498 |
| G10U/C30A/ U6G/C27U | 87 | C2A/G31U/ G10A/C30U | 3105 | C2A/G31U/ G10U/C30A/ U6G/C27U | 786 |
| C2G/G31C/ G10A/C30U | 2365 | C2A/G31U/ G10C/C30G | 3475 | C2G/G31C/ G10A/C30U/ U9A/U14G/C | 236 |
| C2G/G31C/ G10C/C30G | 2684 | C2A/G31U/ G10U/C30A | 3024 | C2G/G31C/ G10C/C30G/ U9A/U14G/C | 245 |
| C2G/G31C/ G10U/C30A | 3125 | C2G/G31C/ G10A/C30U/ U6G/C27U | 758 | C2G/G31C/ G10U/C30A/ U9A/U14G/C | 198 |
| C2U/G31A/ G10A/C30U | 2578 | C2G/G31C/ G10C/C30G/ U6G/C27U | 736 | C2U/G31A/ G10A/C30U/ U9A/U14G/C | 178 |
| C2U/G31A/ G10C/C30G | 2986 | C2G/G31C/ G10U/C30A/ U6G/C27U | 652 | C2U/G31A/ G10C/C30G/ U9A/U14G/C | 196 |

TABLE 3-continued

| Activation of III-3 by Pepper mutants with multiple mutations | | | | | |
|---|---|---|---|---|---|
| Mutant | Activation folds | Mutant | Activation folds | Mutant | Activation folds |
| C2A/G31U/ G10A/C30U/ U9A/U14G/C | 216 | C2A/G31U/ G10C/C30G/ U9A/U14G/C | 103 | C2A/G31U/ G10U/C30A/ U9A/U14G/C | 156 |

Example 4. Base-Modified Pepper's Activating Effect on III-3

Figure 5:
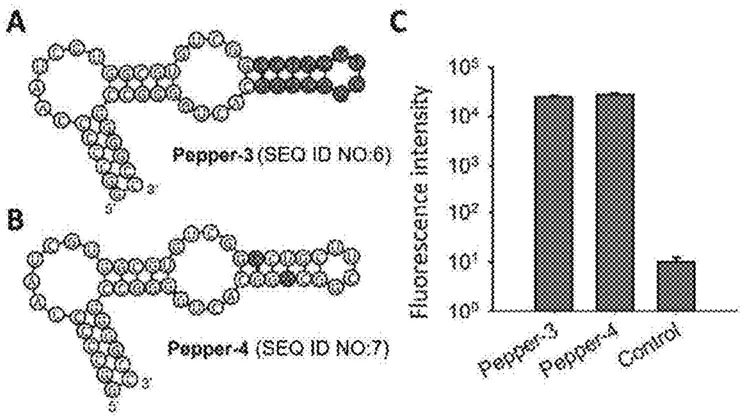
FIG. 5 Activation effect of Pepper modified with different bases on III-3. (A) The secondary structure diagram of Pepper-3 aptamers containing deoxyribonucleotides (dark color in the drawing); (B) the secondary structure diagram of Pepper-4 aptamers with 2'F modification (dark color in the drawing); (C) activation effects of Pepper with different modifications on III-3. "Control" is to replace Pepper-3 or Pepper-4 aptamer with buffer.

In order to detect the activation of III-3 by modified Pepper, base-modified Pepper-3 was synthesized (SEQ ID NO: 6, the underlined nucleotides in GGCCCC-CAAUCGUGGCGUGUCGGCCUGCUUCGGCAGGCA-CUGGCGCCGG GGCC contain deoxyribonucleotide bases) and Pepper-4 (SEQ ID NO: 7, the underlined nucleotides in GCCCCCCAAUCGUGGCGUGUCGGCCUGC-UUCGGCAGGCACUGGCGCCGG GGGCC contain 2'-F modification) (synthesized by Shanghai GenePharma Co., Ltd), which contain deoxyribonucleotides replacement (shaded bases in FIG. 5A) or 2'-F modification (shaded bases in FIG. 5B) in the stem-loop region of Pepper. Detection of the fluorescence activation of III-3 fluorophore by these modified Peppers was carried out according to the commonly used experimental method (5). The results showed that the modified Pepper-3 and Pepper-4 could still significantly activate the fluorescence of III-3 fluorophore (FIG. 5C).

Example 5. Pepper Tandem Arrays

In order to detect the fluorescence activation of III-3 by different Pepper arrays, Pepper is connected to form tandem arrays in different forms, including the following three types:

(1) "tandem array 1" (FIG. 6A), different copies of Pepper are connected via "head-to-tail" to generate nPepper (where n represents any copy number of Pepper). In this example, the cDNA encoding F30-2Pepper-5, F30-4Pepper-5, F30-8Pepper-5, F30-16Pepper-5 and F30-32 Pepper-2 (The sequences of the RNA aptamer are SEQ ID NO: 8, SEQ ID NO: 9, SEQ ID NO: 10, SEQ ID NO: 11, SEQ ID NO: 12, respectively). After PCR amplification, the RNA aptamers were prepared according to the commonly used experimental methods (1). 0.1 M RNA aptamer was incubated with 10 M III-3 and fluorescence was measured according to the commonly used experimental method (5). The results showed that the fluorescence of nPepper-III-3 increased along with the increasing copy number of Pepper (n) (FIG. 6D). When n>8, with the increase of n, the fluorescence of nPepper-III-3 did not increase along with the increasing n, but was still much higher than that of Pepper-III-3 (FIG. 6D), indicating that the "tandem array 1" can be used to increase the fluorescence intensity of Pepper-III-3 complex.

(2) "tandem array 2" (FIG. 6B), Pepper serves as a structural unit and is connected to generate n×Pepper (where n represents any copy number of Pepper). In this example, the cDNAs encoding 2×Pepper-6, 4×Pepper-6, 8×Pepper-6 and 16×Pepper-6 (The sequences of the RNA aptamer are SEQ ID NO: 13, SEQ ID NO: 14, SEQ ID NO:15 and SEQ ID NO:16 respectively) were commercial synthesized. The RNA aptamers were prepared according to the commonly used experimental methods (1). 0.1 μM RNA aptamer was incubated with 10 μM III-3 and fluorescence was measured according to the commonly used experimental method (5). The results showed that that the fluorescence of n×Pepper-III-3 also increased along with the increasing copy number of Pepper (n) (FIG. 6E), indicating that the fluorescence intensity of Pepper-III-3 complex can be increased through the form of "tandem array 2".

(3) "tandem array 3" (FIG. 6C), which is a combination of "tandem array 1"and" tandem array 2". nPepper generated from "tandem array 1" serves as a structural unit and is connected to generate n1×n2Pepper according to the form of "tandem array 2" (where n1 and n2 represent any copy number of Pepper). In this example, the cDNAs encoding 2×2Pepper-5, 4×2Pepper-5, and 8×2Pepper-5 (The sequences of the RNA aptamer are SEQ ID NO: 17, SEQ ID NO: 18 and SEQ ID NO: 19, respectively) were commercial synthesized. The RNA aptamers were prepared according to the commonly used experimental methods (1). 0.1 M RNA aptamer was incubated with 20 M III-3 and fluorescence was measured according to the commonly used experimental method (5). The results showed that the fluorescence intensity of Pepper-III-3 obtained by the form of "tandem array 3" was significantly higher than that of Pepper-III-3 (FIG. 6F), indicating that the fluorescence of Pepper-III complex can be improved by the form of "tandem array 3".

Example 6. Characterization of III-3 Analogues

F30-Pepper-1 RNA aptamer was prepared according to the commonly used experimental methods (1), and was used to detect the properties of III-3 analogues upon Pepper binding, including the fluorescence spectrum, extinction coefficient, quantum yield, fluorescence activation fold and the binding constant (Kd). The results were shown in Table 4. From the data shown in the table, F30-Pepper-1 still could activate the fluorescence of III-3 analogues. IDC-28 T2 M

TABLE 4

The properties of F30-Pepper-1 RNA aptamer with different fluorophores

| | $Ex_{max}$ (nm) | $Em_{max}$ (nm) | Extinction coefficient ($M^{-1}$ $cm^{-1}$) | Quantum yield | Activation fold | $K_d$ (nM) |
|---|---|---|---|---|---|---|
| F30-Pepper-1-III-7 | 443 | 485 | 49100 | 0.42 | 691 | 8.0 |
| F30-Pepper-1-III-6 | 435 | 497 | 54700 | 0.57 | 16601 | 6.7 |
| F30-Pepper-1-III-8 | 458 | 508 | 42500 | 0.30 | 9091 | 27.0 |

TABLE 4-continued

The properties of F30-Pepper-1 RNA aptamer with different fluorophores

| | $Ex_{max}$ (nm) | $Em_{max}$ (nm) | Extinction coefficient ($M^{-1}$ $cm^{-1}$) | Quantum yield | Activation fold | $K_d$ (nM) |
|---|---|---|---|---|---|---|
| F30-Pepper-1-III-4 | 458 | 514 | 44100 | 0.45 | 4748 | 12.0 |
| F30-Pepper-1-III-15 | 491 | 525 | 74100 | 0.70 | 585 | 3.8 |
| F30-Pepper-1-III-3 | 485 | 530 | 65300 | 0.66 | 3595 | 3.5 |
| F30-Pepper-1-III-18 | 515 | 599 | 54400 | 0.43 | 708 | 18.0 |
| F30-Pepper-1-III-21 | 577 | 620 | 100000 | 0.58 | 12600 | 6.1 |
| F30-Pepper-1-III-1 | 482 | 528 | 59600 | 0.62 | 1256 | 6.3 |
| F30-Pepper-1-III-2 | 481 | 527 | 62300 | 0.52 | 1563 | 12.3 |
| F30-Pepper-1-III-5 | 462 | 501 | 23000 | 0.19 | 697 | 45.3 |
| F30-Pepper-1-III-9 | 455 | 502 | 39600 | 0.23 | 1360 | 23.2 |
| F30-Pepper-1-III-10 | 459 | 506 | 40200 | 0.26 | 2365 | 18.3 |
| F30-Pepper-1-III-11 | 453 | 492 | 42000 | 0.15 | 596 | 53.3 |
| F30-Pepper-1-III-12 | 452 | 486 | 39600 | 0.16 | 650 | 63.2 |
| F30-Pepper-1-III-13 | 476 | 512 | 52300 | 0.23 | 853 | 35.1 |
| F30-Pepper-1-III-14 | 465 | 512 | 45600 | 0.18 | 453 | 64.3 |
| F30-Pepper-1-III-16 | 492 | 534 | 78600 | 0.76 | 698 | 6.1 |
| F30-Pepper-1-III-17 | 508 | 596 | 52300 | 0.51 | 584 | 23.2 |
| F30-Pepper-1-III-19 | 498 | 586 | 42500 | 0.36 | 542 | 36.5 |
| F30-Pepper-1-III-20 | 501 | 590 | 39600 | 0.31 | 365 | 67.3 |

Example 7. Labeling of Bacterial RNA Using Pepper-III-3 Complex

In order to test the effect of Pepper-III-3 in bacteria, a bacterial expression plasmid expressing F30-Pepper-1 was constructed. Primers were used to amplify F30-Pepper-1 in Example 2. Primers were used to amplify pET28a to remove the promoter and multiple cloning site regions. The obtained F30-Pepper-1 fragment and the linearized pET28a were ligated according to the commonly used experimental method (4). The obtained recombinant plasmid was named pET28a-T7-F30-Pepper-1.

The primers used to amplify the F30-Pepper-1 fragment are:

Forward primer (P1):

Forward primer (P1), set forth by SEQ ID NO: 32: 5'-GATCCCGCGAAATTAATACGACTCAC-TATAGGGTTGCCATGTG TATGTGGG-3'

Reverse primer (P2), set forth by SEQ ID NO: 33: 5'-CAAGGGGTTATGCTATTGCCATGAATGATCC-3'

The primers used to amplify and linearize the pET28a vector are:

Forward primer (P3), set forth by SEQ ID NO: 34: 5'-TAGCATAACCCCTTGGGGCCTCTAAACGGGTCTT-GAG-3'

Reverse primer (P4), set forth by SEQ ID NO: 35: 5'-ATTTCGCGGGATCGAGATCTCGATCCTC-TACGCCGGACG-3'

Figure 7:
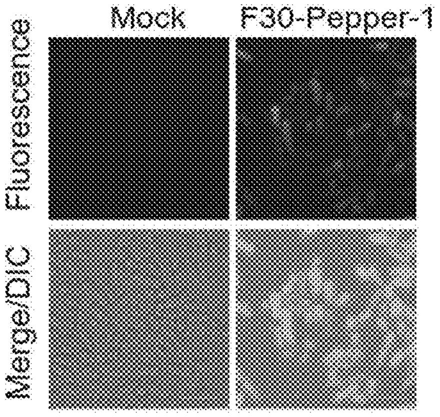
FIG. 7 The labeling effect of F30-Pepper-1-III-3 complex on RNA in bacteria.

The recombinant plasmid pET28a-T7-F30-Pepper-1was transformed into BL21(DE3, Star) *E. coli* strain. A single clone was picked and cultured at 37° C. to an $OD_{600}$ around 0.2 before addition of 1 mM IPTG to induce the expression of F30-Pepper-1. 4 hours after induction, the bacteria were harvested and resuspended in PBS solution containing 2 μM III-3. BL21 (DE3, Star) *E. coli* transformed with pET28a empty vector was used as the control. The results showed that bacteria exhibited bright yellow-green fluorescence only when F30-Pepper-1 was expressed and in the presence of III-3 (FIG. 7), indicating that Pepper-III-3 complex can be used for fluorescent labeling of RNA in bacteria.

Example 8. Labeling of Yeast RNA Using Pepper-III-3 Complex

In order to test the effect of Pepper-III-3 in yeast, a yeast expression plasmid expressing F30-Pepper-1 was constructed. The F30-Pepper-1 DNA fragment in Example 2 was amplified using primers, and the amplified F30-Pepper-1 fragment was inserted into the pYES2.1TOPO TA vector according to the commonly used experimental method (4). The obtained recombinant plasmid was named pYES2.1-F30-Pepper-1.

The primers used to amplify the F30-Pepper-1 fragment are:

Forward primer (P5), set forth by SEQ ID NO: 36: 5'-GGAATATTAAGCTCGCCCTTTTGC-CATGTGTATGTGGG-3'

Reverse primer (P6), set forth by SEQ ID NO: 37: 5'-TGACCTCGAAGCTCGCCCTTGTTGCCATGAAT-GATCC-3'

Figure 8:
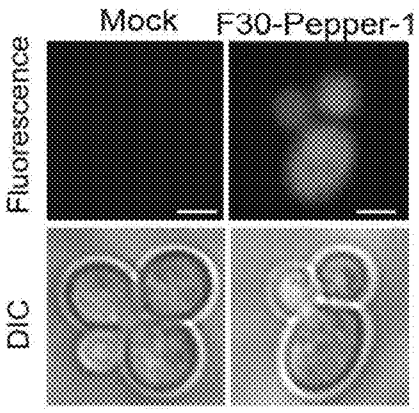
FIG. 8 The labeling effect of F30-Pepper-1-III-3 complex on RNA in yeast cells.

The recombinant plasmid pYES2.1-F30-Pepper-1 was transformed into BY4741 strain, and a single clone was picked and cultured at 30° C. to an OD600=0.1 before addition of 1 mM galactose to induce the expression of F30-Pepper-1. 10 hours after induction, the yeast cells were harvested and resuspended in PBS containing 2 μM III-3. The untreated BY4741 strain was used as the control. The results showed that yeast cells exhibited bright yellow-green fluorescence only when F30-Pepper-1 was expressed and in the presence of III-3 (FIG. 8), indicating that Pepper-III-3 complex can be used for RNA labeling in yeast cells.

Example 9. RNA Labeling in Mammalian Cells Using Pepper and III-3 and its Analogs In order to use Pepper and III-3 for RNA labeling in mammalian cells, the reported Broccoli and Corn aptamer (binding to DFHBI-1T and DFHO fluorophores, respectively) were used as the controls (Filonov et al. Journal of the American Chemical Society 2014. 136: 16299-16308; Song et al. Nature chemical biology 2017. 13: 1187-1194). The mammalian cell expression plasmids expressing the RNA aptamers were constructed. The primers P7 and P8 were used to amplify F30-Pepper-1 and F30-Broccoli in Example 2, and the primers P9 and P10 were used to amplify the synthesized tRNA-Corn cDNA fragment (the RNA sequence was SEQ ID No: 20). The obtained fragments were ligated into the pLKO.1 puro vector according to the commonly used experimental method (4). The obtained expression vectors were named pLKO.1-F30-Pepper-1, pLKO.1-F30-Broccoli and pLKO.1-tRNA-Corn, which express F30-Pepper-1, F30-Broccoli and tRNA-Corn RNA, respectively.

The primers used to amplify F30-Pepper-1 and F30-Broccoli are:

Forward primer (P7), set forth by SEQ ID NO: 38:
5'-GGAAAGGACGAAACTCTAGATTGC-CATGTGTATGTGGG-3'

Reverse primer (P8), set forth by SEQ ID NO: 39:
5'-TGTCTCGAGGTCGAGAATT-CAAAAAAAGTTGCCATGAATGAT CC-3'

The primers used to amplify tRNA-Corn are:

Forward primer (P9), set forth by SEQ ID NO: 40:
5'-GGAAAGGACGAAACTCTAGAGCCCGGA-TAGCTCAGTCGG-3'

Reverse primer (P10), set forth by SEQ ID NO: 41:
5'-TGTCTCGAGGTCGAGAATT-CAAAAAAATGGCGCCCGAACAGG GACTTGCGAGCTCAG-GATCCTTCCGTTTCGCACTGG-3'

In order to use Pepper and III-3 analogues for RNA labeling in mammalian cells, a mammalian expression plasmid expressing F30-8Pepper-5 was constructed. The primers P7 and P8 in this example were used to amplify the F30-8Pepper-5 fragment in Example 5, and the fragments was inserted into the pLKO.1 puro vector using the commonly used experimental method (4). The obtained expression vector was named pLKO.1-F30-8Pepper-5.

Figure 9:
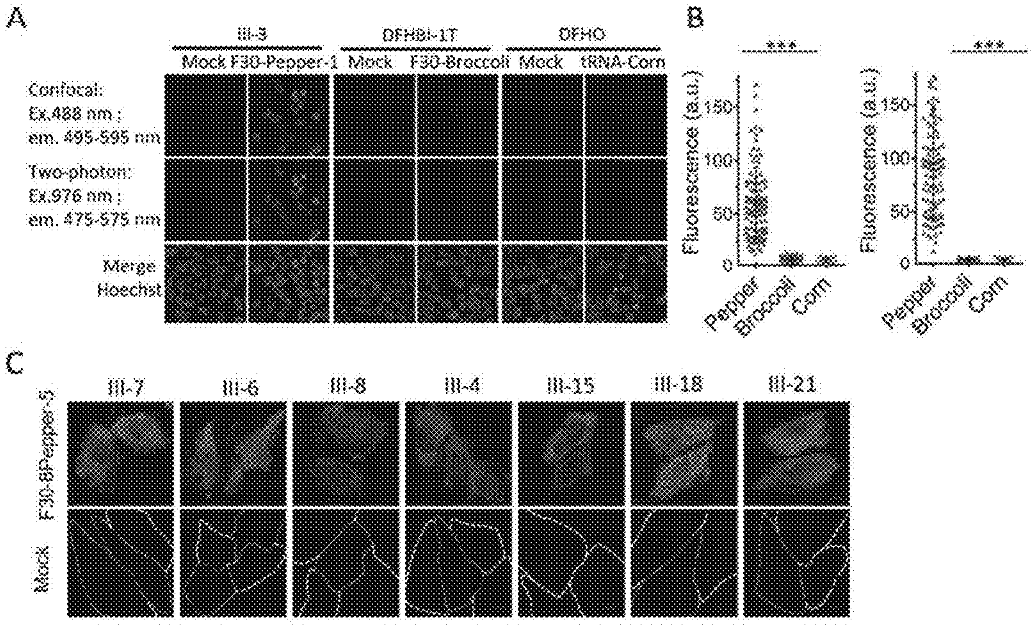
FIG. 9 The labeling effects of Pepper, III-3 and analogue thereof in labeling RNA in mammalian cells. (A) Comparison of the effects of F30-Pepper-1-III-3, F30-Broccoli-DFHBI-1T and tRNA-Corn-DFHO on RNA labeling in mammalian cell; (B) statistical results of fluorescence in FIG. (A); (C) effects of F30-8Pepper-5 and III-3 analogs on RNA labeling in mammalian cells.

The pLKO.1-F30-8Pepper-5 plasmid was transfected into 293T/17 cells. Different III-3 analogues were added into the culture for labeling 24 hours after transfection. Fluorescence imaging was performed according to the commonly used experimental method (3). The results showed that different III-3 analogs could be used to specifically label cells expressing F30-8Pepper-5, but not the control cells without expression of F30-8Pepper-5 (FIG. 9C), indicating that Pepper and III-3 and its analogs can be used to label RNA in mammalian cells.

Example 10. Construction of Pepper-Based Sensors

In order to construct Pepper-based sensors for detecting analytes, the nucleotides in the stem-loop region in the Pepper-1 (SEQ ID No: 2) structure were replaced with the aptamers that can specifically recognize and bind adenosine and guanosine (GTP), respectively. The aptamers Pepper-1 were fused by linkage with different lengths and different nucleotides (FIG. 10A). The RNA sensors were prepared according to the commonly used experimental method (1). The RNA sensors were incubated with III-3 fluorophore, and the fluorescence was measured in the presence or absence of adenosine or GTP using a multifunctional microplate reader. The results showed that, for the adenosine sensor, the activation fold could reach 88 folds when the linkage between the adenosine aptamer and Pepper-1 was linkage 2 in FIG. 10B. The corresponding sequence of the RNA sensor was SEQ ID No:21; for the GTP sensor, the activation fold could reach 10 folds when the linkage between the adenosine aptamer and Pepper-1 was linkage 3 in FIG. 10B. The corresponding sequence of the RNA sensor was SEQ ID No:22.

Example 11. Tracking of RNA Localization in Cells by Pepper

In order to use Pepper to track RNA localization in cells, chimeric RNA expression plasmids in which Pepper was fused to different RNAs were constructed. cDNA encoding 4Pepper-7 (the sequence of the RNA aptamer is SEQ ID No: 23) was synthesized and amplified using primers. The obtained fragment was inserted into the HindIII and XhoI sites of pCDNA3.1 hygro(+) vector to generate pCDNA3.1 hygro(+)-4Pepper-7 plasmid. The GAPDH and TMED2 gene fragments (the gene sequences of GAPDH and TMED2 are shown in Genebank: BC009081 and BC025957, respectively) were synthesized and amplified using primers. The obtained GAPDH and TMED2 gene fragments were inserted into the NheI and HindIII sites of pCDNA3.1 hygro(+)-4Pepper-7 vector to generate pCDNA3.1 hygro(+)-GAPDH-4Pepper-7 and pCDNA3.1 hygro(+)-TMED2-4Pepper-7 plasmids that express GAPDH-4Pepper-7 and TMED2-4Pepper-7 chimeric RNAs, respectively. The sequences of the chimeric RNAs are SEQ ID Nos: 24 and 25, respectively.

The primers used to amplify 4Pepper-7 are:

Forward primer (P11), set forth by SEQ ID NO: 42:
5'-TAGCGTTTAAACTTAAGCTTCCCACGGAG-GATCCCCAATC-3'

Reverse primer (P12), set forth by SEQ ID NO: 43:
5'-ACGGGCCCTCTAGACTCGAGCCCACGGAG-GATCCCGGCGCC-3'

The primers used to amplify GAPDH are:

Forward primer (P13), set forth by SEQ ID NO: 44:
5'-GGAGACCCAAGCTGGCTAGCATGGGGAAGGT-GAAGGTCGG-3'

Reverse primer (P14), set forth by SEQ ID NO: 45:
5'-GGATCCTCCGTGGGAAGCTTAAC-CATGCTCTAGCGAGTGTTA CTCCTTGGAGGC-CATGT-3'

The primers used to amplify TMED2 are:

Forward primer (P15), set forth by SEQ ID NO: 46:
5'-GGAGACCCAAGCTGGCTAG-CATGGTGACGCTTGCTGAACT-3'

Reverse primer (P16), set forth by SEQ ID NO: 47:
5'-GGATCCTCCGTGGGAAGCTTAAC-CATGCTCTAGCGAGTTAAA CAACTCTCCGGACTTC-3'

After construction of above plasmids, the inserted sequences were validated by sequencing to ensure correct insertion. The plasmids were extracted using a transfection-grade plasmid extraction kit for subsequent transfection experiments.

Figure 11:
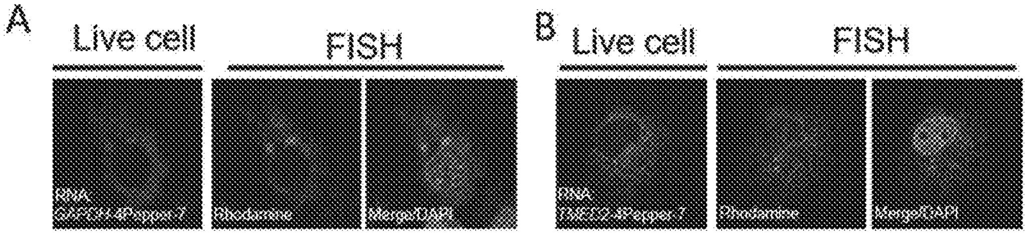
FIG. 11 RNA localization in tracer cells by using Pepper. (A) Detection of GAPDH mRNA localization by using Pepper; (B) detection of Pepper TMED2 mRNA localization by using Pepper.

The pCDNA3.1 hygro(+)-GAPDH-4Pepper-7 and pCDNA3.1 hygro(+)-TMED2-4Pepper-7 plasmids constructed in this example were co-transfected with pCDNA3.1 hygro(+)-BFP into COS-7 cells, respectively. 24 hours after transfection, the cells were imaged according to the fluorescence imaging method described in the commonly used experimental method (3). The imaging results showed that the fluorescence of GAPDH-4Pepper-7-III-3 was mainly localized in the cytoplasm, while the fluorescence of TMED2-4Pepper-7-III-3 exhibited endoplasmic reticulum enrichment, which was consistent with previous studies and the results obtained by fluorescent-labeled in situ hybridization (FISH) (FIG. 11). These results indicate that Pepper can be used to track RNA location.

Example 12. Detection of the Correlation Between mRNA and Protein by Pepper

In order to use Pepper to detect mRNA translation in cells, it was necessary to construct plasmids expressing different Pepper-fused mRNA. Primers were used to amplify mCherry and TagBFP gene fragments using mCherry2-N1

(Addgene: 54517) and EasyFusion T2A-H2B-TagBFP (Addgene: 113086) as the templates. The obtained gene fragments were inserted into the NheI and HindIII sites of pCDNA3.1 hygro(+)-GAPDH-4Pepper-7 vector to generate pCDNA3.1 hygro(+)-mCherry-4Pepper-7 and pCDNA3.1 hygro(+)-TagBFP-4Pepper-7 plasmids that encode mCherry-4Pepper-7 and TagBFP-4Pepper-7, respectively. The sequences of the chimeric RNAs are SEQ ID Nos: 26 and 27, respectively.

The primers used to amplify mCherry are:

Forward primer (P17), set forth by SEQ ID NO: 48:
5'-GGAGACCCAAGCTGGCTAGCATGGT-GAGCAAGGGCGAGGAGG-3'

Reverse primer (P18), set forth by SEQ ID NO: 49:
5'-GGATCCTCCGTGGGAAGCTTAAC-CATGCTCTAGCGAGTTACTT GTACAGCTCGTC-CATG-3'

The primers used to amplify TagBFP are:

Forward primer (P19), set forth by SEQ ID NO: 50:
5'-GGAGACCCAAGCTGGCTAGCATGAGCGAGCT-GATTAAGGA-3'

Reverse primer (P20), set forth by SEQ ID NO: 51:
5'-GGATCCTCCGTGGGAAGCTTCTCCCAAAC-CATGCTCTAGCGA GTGTTAATT-GAGCTTGTGCCCCA-3'

Figure 12:
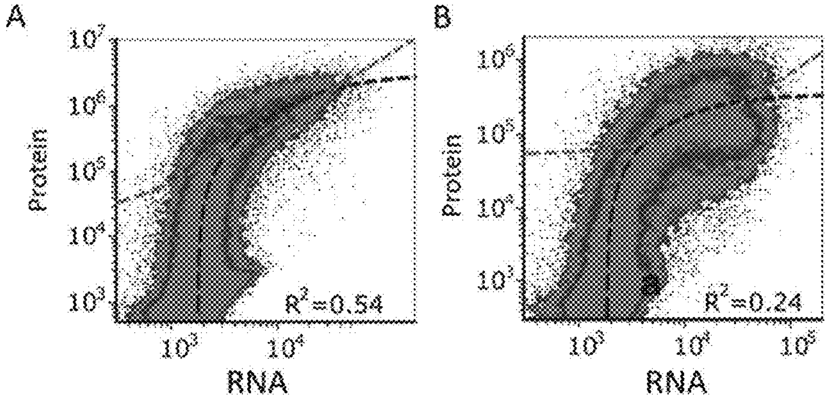
FIG. 12 Exploration of the relationship between mRNA and protein in cells by using Pepper. (A) Flow cytometry analysis result of BFP protein and RNA expression thereof; (B) flow cytometry analysis result of mCherry protein and RNA expression thereof.

The recombinant plasmids pCDNA3.1 hygro(+)-BFP-4Pepper-7 and pCDNA3.1 hygro(+)-mCherry-4Pepper-7 were transfected into COS-7 cells, respectively. 24 hours after transfection, the transfected cells were labeled with 0.2 M III-3 fluorophore. The fluorescence of mRNA (4Pepper-7-III-3) and fluorescence proteins (BFP and mCherry) was analyzed using flow cytometry. The fluorescence of mRNA and protein was fitted using the Michaelis equation to obtain $R^2$. The results showed that the translation efficiencies of different mRNAs varied significantly different (FIG. 12), indicating that Pepper can be used to detect the correlation between mRNA and protein.

Example 13. Detection of Genomic DNA by Pepper

Figure 13:
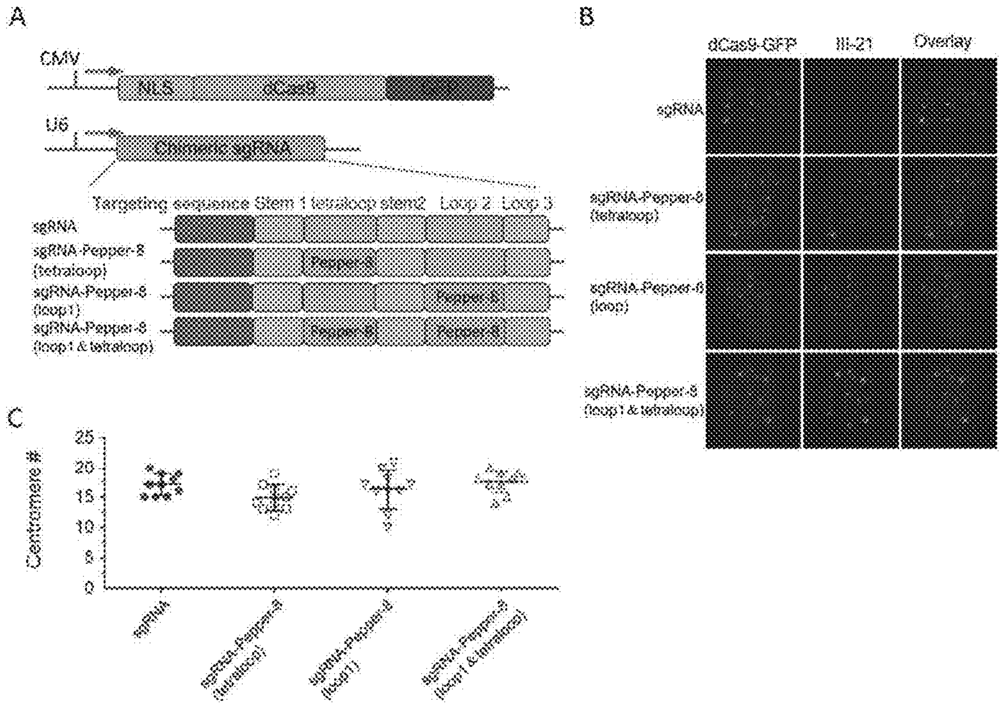
FIG. 13 Detection of genomic DNA by using Pepper. (A) Diagram of dCas9 and different chimeric sgRNA; (B) imaging results of genomic DNA by dCas9 and different chimeric sgRNA; (C) statistical results of bright spot particles in each cell in (B).

In order to use Pepper to detect genomic DNA, a recombinant plasmid expressing chimeric RNA of Pepper-8 and sgRNA was constructed. cDNAs encoding sgRNA-Pepper-8 (loop1), sgRNA-Pepper-8 (tetraloop) and sgRNA-Pepper-8 (loop1 and tetraloop) containing centromere targeting sequence were synthesized. The encoded RNA sequences are SEQ ID No: 28, 29 and 30, respectively. Primers P21 and P22 were used to amplify above cDNAs, primers P23 and P24 were used to amplify the psgRNA plasmid (Shao et al. Nucleic acids research 2016. 44: e86). The obtained cDNAs were inserted into the linearized psgRNA vector according to the commonly used experimental method (4) to generate psgRNA-Pepper-8 (loop1), psgRNA-Pepper-8 (loop2) and psgRNA-Pepper-8 (loop1 and tetraloop), respectively (FIG. 13A). Primers P25 and P26 were used to amplify the dCas9-GFP gene fragment using pSLQ1645(dCas9-GFP) (Shao et al. Nucleic acids research 2016. 44: e86) as the template. The obtained gene fragment was inserted into the HindIII and XhoI sites of pCDNA3.1 hygro(+) vector to generate pCDNA3.1 hygro(+)-dCas9-GFP according to the commonly used experimental method (4).

The primers used to amplify the cDNA encoding Pepper and sgRNA chimeric RNA are:

Forward primer (P21), set forth by SEQ ID NO: 52:
5'-AAAGGACGAAACACCGAATCTGCAAGTGGAT-ATTGTTTGAG-3

Reverse primer (P22), set forth by SEQ ID NO: 53:
5'-TGATCTAGAAAAAAAGCACCGACTCGGTGCCAC-3'

The primers used to amplify the psgRNA plasmid to linearize it are:

Forward primer (P23), set forth by SEQ ID NO: 54:
5'-TTTTTTTCTAGATCATAATCAGCCATACC-3'

Reverse primer (P24), set forth by SEQ ID NO: 55:
5'-GGTGTTTCGTCCTTTCCACAAG-3'

Reverse primer (P24): 5'-GGTGTTTCGTCCTTTC-CACAAG-3'

The primers used to amplify SpdCas9-GFP are:

Forward primer (P25), set forth by SEQ ID NO: 56:
5'-TAGCGTTTAAACT-TAAGCTTGTGCAGGCTGGCGCCACCATGG CCCC-3'

Reverse primer (P26), set forth by SEQ ID NO: 57:
5'-ACGGGCCCTCTAGACTCGAGTTACTTGTA-CAGCTCGTCCATGC-3' pCDNA3.1 hygro(+)-dCas9-GFP and psgRNA-Pepper-6 (loop1), psgRNA-Pepper-6 (loop2) and psgRNA-Pepper-6 (loop1 and tetraloop) were co-transfected into COS-7 cells, respectively. 24 hours after transfection, the cells were labeled with 1 μM III-21 and Hoechst, and the fluorescence of Pepper-8-III-21, GFP and Hoechst were imaged using a fluorescence microscope. The imaging results showed that the fluorescence of Pepper-8-III-21 was mainly localized in the nucleus to exhibit aggregates in dots (centromeres), which was almost completely overlayed with the fluorescence of dCas9-GFP (FIG. 13B). Furthermore, the number of dots was consistent with the sgRNA alone (FIG. 13C), indicating that Pepper can be used to image genetic DNA.

Example 14. Super-Resolution Imaging of RNA by Pepper

In order to use Pepper for super-resolution imaging of RNA, a plasmid that tethered RNA to the nucleus was constructed. The 4Pepper-9-MS2 DNA fragment (SEQ ID No: 31) was synthesized and amplified using primers P27 and P28. The obtained fragment was inserted into XbaI and EcoRI sites of pLKO.1 vector to generate pLKO.1-4Pepper-9-MS2 according to the commonly used experimental method (4). Primers were used to amplify H2B gene fragment using pCS-H2B-EGFP (Addgene: 53744) as the template, primers were used to amplify tdMCP gene fragments using pHAGE-Ubc-NLS-HA-tdMCP-GFP (Addgene: 40649) as the template, primers were used to amplify tagBFP gene fragment, the overlap PCR was used to fuse tdMCP, tagBFP and H2B gene fragments to obtain the tdMCP-tagBFP-H2B fusion fragment. The obtained tdMCP-tagBFP-H2B fragment was inserted into pmTurquoise2-Golgi (Addgene: 36205) to generate pH2B-tdMCP-tagBFP that encodes a nuclear-localized tdMCP-tagBFP according to the commonly used experimental method (4).

The primers used to amplify the 4Pepper-9-MS2 DNA fragment are:

Forward primer (P27), set forth by SEQ ID NO: 58:
5'-GGAAAGGACGAAACTCTAGAGGGGCCCCC-CAATCGTGG-3'

Reverse primer (P28), set forth by SEQ ID NO: 59:
5'-TGTCTCGAGGTCGAGAATT-CAAAAAAAGGGGCCCCCGGCGC CAGTG-3'

The primers used to amplify the tdMCP gene fragment are:

Forward primer (P29), set forth by SEQ ID NO: 60:
5'-GAACCGTCAGATCCGCTAGCCACCATGGGC-TACCCCTACGAC GTGCCCG-3'

Reverse primer (P30), set forth by SEQ ID NO: 61: 5'-TCCAGAATCCGCGTAGATGCCGG-3'

The primers used to amplify the tagBFP gene fragment are:

Forward primer (P31), set forth by SEQ ID NO: 62: 5'-CTACGCGGATTCTGGAGGCGGTGGATCCAT-GAGCGAGCTGAT TAAGGAG-3'

Reverse primer (P32), set forth by SEQ ID NO: 63: 5'-AGATCTATTGAGCTTGTGCCCCAGTTTG-3'

The primers used to amplify H2B gene fragment are:

Forward primer (P33), set forth by SEQ ID NO: 64: 5'-CAAGCTCAATAGATCTATGCCT-GAACCGGCAAAATCC-3'

Reverse primer (P34), set forth by SEQ ID NO: 65: 5'-GACTGCAGAATTCGAAGCTTACTTG-GAGCTGGTGTACTTG-3'

Figure 14:
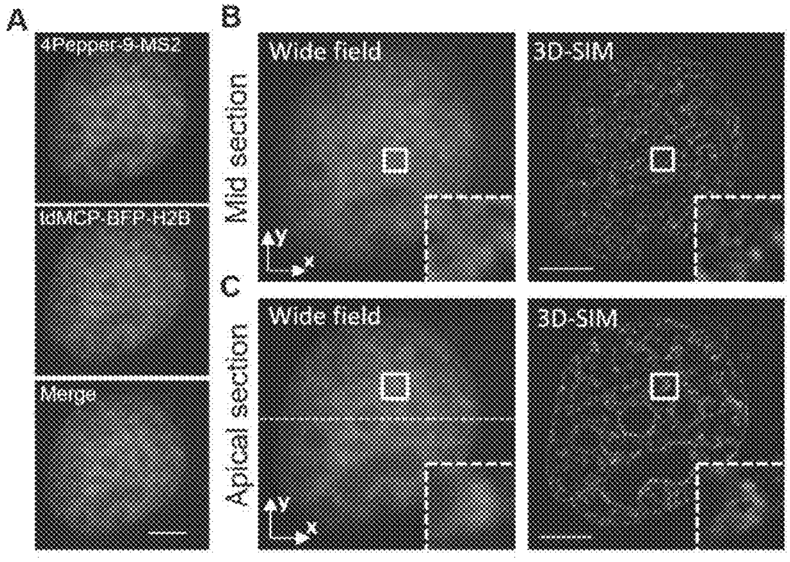
FIG. 14 Super-resolution imaging of RNA by using Pepper. (A) Co-localization of 4Pepper-9-MS2 RNA and tdMCP-BFP-H2B protein; (B) imaging results of wide field and SIM in nuclear middle layer; (C) imaging results of wide field and SIM in nuclear top layer.

The pLKO.1-4Pepper-9-MS2 and pH2B-tdPP7-tagBFP plasmids were co-transfected into COS-7 cells. 24 hours after transfection, the transfected cells were labeled with 11-21 fluorophore, and the fluorescence distribution of Pepper-III-21 complex was imaged using a Zeiss Elyra PS.1 super-resolution fluorescence microscope using an excitation of a 561 nm long-pass filter equipped with a Zeiss Plan-Apochromat 63×(NA, 1.4) Oil DIC M27 objective and a CMOS size of 1024×1024 pixels. The imaged were processed using a ZEN 2011 Black (Zeiss) software. The imaging results showed that the cells co-transfected with pLKO.1-4Pepper-9-MS2 and pH2B-tdMCP-tagBFP showed an obvious nucleopore structure (FIG. 14). The results indicate that Pepper can be used for super-resolution imaging of RNA.

Example 15. RNA Extraction and Purification by Pepper

In order to use Pepper for RNA extraction and purification, the pCDNA3.1 hygro(+)-TagBFP-4Pepper-7 and pCDNA3.1 hygro(+)-mCherry-4Pepper-7 plasmids in Example 12 were transfected into COS-7 cells, respectively. 24 hours after transfection, the cells were collected and the total RNA of the cells was extracted using the Easyp Super Total RNA Extraction Kit (Promega). The extracted total RNA was dissolved in buffer containing 40 mM HEPES, pH 7.4, 125 mM KCl, 5 mM $MgCl_2$. The RNA was incubated at 70° C. for 10 min and placed at room temperature for more than 30 min.

500 μL activated Thiol Sepharose 4B (GE Healthcare) was washed twice with 500 μL PBS, and then was incubated with PBS containing 10 mM TCEP (Sigma) for 1 h at room temperature. After washing twice with 500 μL PBS, maleamide conjugated III-3 fluorophore (Mal-III-3) was added to react for 30 min at room temperature, and was washed three times with 500 μL PBS. The treated total RNA was incubated with the treated beads at room temperature. After 30 minutes, the mixture was centrifuged at 4000 rpm for 2 minutes, and the supernatant was discarded. The agarose beads were washed with buffer containing 40 mM HEPES, pH 7.4, 125 mM KCl, and 5 mM $MgCl_2$ for 6 times, and the supernatant was removed by centrifugation each time. The beads were resuspended with DEPC water, treated at 70° C. for 10 min, and centrifuged at 4000 rpm for 2 min. Then the supernatant was collected. 1/10 volume of NaAc, 2.5 times volume of absolute ethanol was added into the collected supernatant and placed in a refrigerator at −80° C. for 20 min. The mixture was centrifuged at 14000 rpm at 4° C. for 10 min. The precipitate was collected and the supernatant was discarded. The pre-cooled 70% ethanol solution was used to wash the precipitate. The mixture was then centrifuged at 14000 rpm for 10 min at 4° C. The precipitate was collected and the supernatant was discarded. Such procedure was repeated once again. The precipitate was placed at room temperature for 5 minutes, and then a small volume of DEPC water was used to resuspend the precipitate after the alcohol was evaporated.

Figure 15:
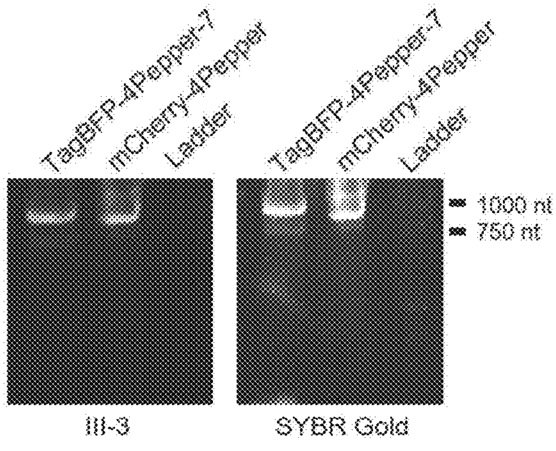
FIG. 15 Pepper serving as labels for RNA extraction and purification. The "ruler" is a single-stranded DNA standard used for calibrating size of the aptamer.

The recovered RNA was validated by electrophoresis. The gel was incubated with buffer containing 5 μM III-3 in 40 mM HEPES, pH 7.4, 125 mM KCl, and 5 mM $MgCl_2$ for 30 min, and the fluorescence of 4Pepper-III-3 in the gel was detected. The imaging results showed that two RNA bands in the gel exhibited bright Pepper-III-3 fluorescence signals, which were TagBFP-4Pepper and mCherry-4Pepper, respectively (FIG. 15), indicating that Pepper can be used as a tag for RNA extraction and purification.

Example 16: The Synthesis of Compound III-1 and its Analogues Compound III-1

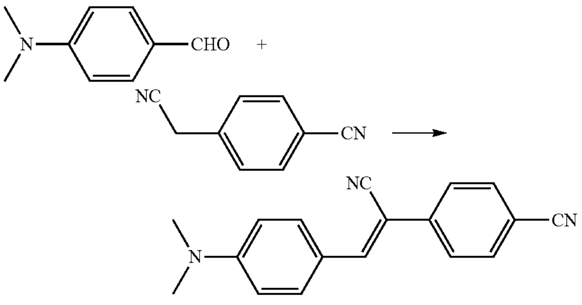

III-1

To a stirring solution of p-dimethylaminobenzaldehyde (0.35 g, 2.3 mmol) and 4-cyano-benzeneacetonitrile (0.4 g, 2.8 mmol) in 20 mL methanol, 2 drops of piperidine were added. After stirring at ambient temperature for 2 h, the mixture was cool to room temperature. A large amount of precipitate was appeared. Then the precipitate was obtained by filtration and washed with cold EtOH three times. The orange solid was obtained after dried under vacuum (0.60 g, yield 95%). $^1H$ NMR (400 MHz, DMSO-$d_6$): δ=3.05 (s, 6H), 6.83 (d, J=9.2 Hz, 2H), 7.84-7.94 (m, 6H), 8.02 ppm (s, 1H). HRMS (ESI-TOF): Calcd. For $C_{18}H_{16}O_3[M+H]^+$: 274.1344. Found: 274.1345.

Compound III-2:

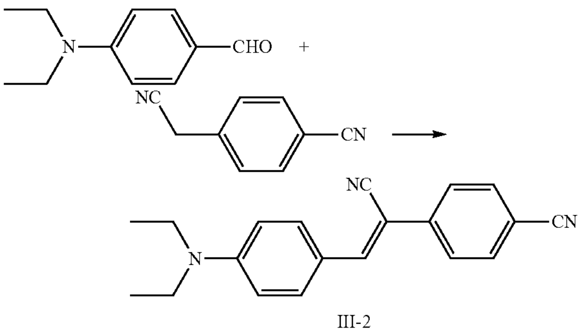

III-2

With reference to the synthetic method of compound III-1 (0.34, yield 89%). $^1$H NMR (400 MHz, DMSO-d$_6$): δ=1.23 (t, J=7.60 Hz, 6H), 3.05 (t, J=7.60 Hz, 4H), 6.84 (d, J=9.2 Hz, 2H), 7.84-7.95 (m, 6H), 8.09 ppm (s, 1H). HRMS (ESI-TOF): Calcd. For $C_{20}H_{20}O_3$[M+H]$^+$: 302.1657. Found: 302.1658.

Compound III-3:

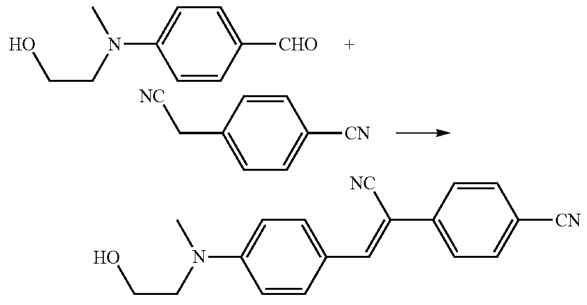

III-3

With reference to the synthetic method of compound III-1 (0.33 g, yield 95%). $^1$H NMR (400 MHz, DMSO-d$_6$): δ=7.96 (s, 1H), 7.85 (d, J=16.0 Hz, 6H), 6.81 (d, J=8.0 Hz, 2H), 4.77 (s, 1H), 3.55 (d, J=28.0 Hz, 4H), 3.04 (s, 1H). HRMS (ESI-TOF): Calcd. For $C_{19}H_{18}N_3O$ [M+H]$^+$: 304.1450. Found: 304.1451.

Compound III-4

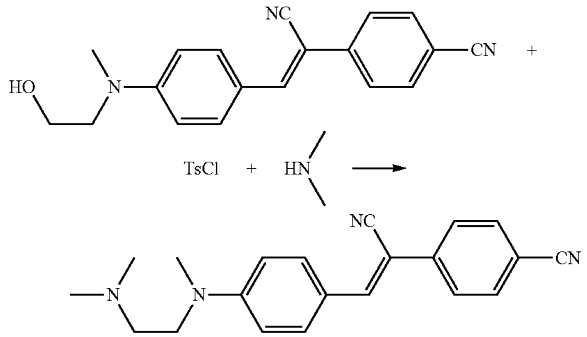

III-4

To stirring solution of compound III-3 (0.61 g, 2.0 mmol) and TEA (0.25 g, 2.2 mmol) in 40 mL dried DCM, 4-tosyl chloride (0.38 g, 2.0 mmol) in 10 mL DCM was added slowly under 0° C. The resulting mixture was stirred under Ar atom and was permitted to warm to room temperature. After complete the reaction, the mixture was quenched by 2 mL of water. The reaction mixture was extracted three times and the organic phase was dried with anhydrous $Na_2SO_4$ and evaporation under reduced pressure, the residue was used in the next step without purified.

To a stirring solution of the residue in 20 mL $CH_3CN$, 1 ml MeNH2 was added under Ar atmosphere. The mixture was heated to refluxed overnight. Upon completing the reaction, the reaction mixture was cooled to room temperature and the organic liquid was removed under reduce pressure. Then the residue was dissolved in 50 mL DCM and the organic phase was washed with water and brine (2×100 ml). Upon drying over anhydrous $Na_2SO_4$ and evaporation under reduced pressure, the residue was purified by column chromatography on silica gel to afford orangered solid. (0.54 g, 82%). $^1$H NMR (400 MHz, $CDCl_3$): δ=7.88 (d, J=9.0 Hz, 2H), 7.74-7.65 (m, 4H), 7.48 (s, 1H), 6.73 (d, J=9.1 Hz, 2H), 3.60-3.55 (m, 2H), 3.08 (s, 3H), 2.57-2.52 (m, 2H), 2.34 (s, 6H). HRMS (ESI-TOF): Calcd. For $C_{21}H_{23}N_4$[M+H]$^+$: 331.1923. Found: 331.1925.

Compound III-5

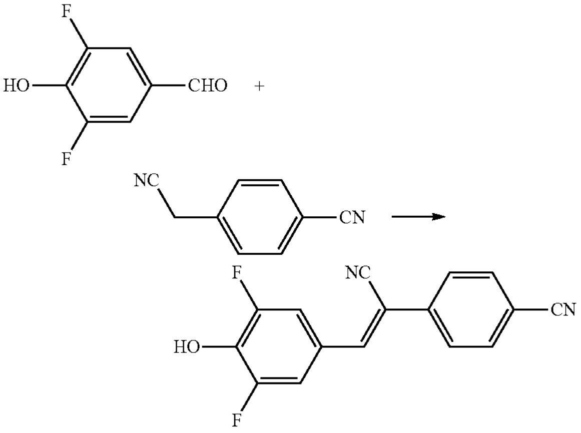

III-5

To a stirring solution of 3,5-difluoro-4-hydroxybenzaldehyde (0.32 g, 2.0 mmol) and 4-cyano-benzeneacetonitrile (0.35 g, 2.4 mmol) in 40 mL anhydrous EtOH, 2 drops of piperidine were added. After stirring at ambient temperature for 2 h, the mixture was cool to room temperature. A large amount of precipitate was appeared. Then the precipitate was obtained by filtration and washed with cold EtOH three times. The orange solid was obtained after dried under vacuum. $^1$H NMR (400 MHz, $CDCl_3$): δ=7.80 (d, J=9.0 Hz, 2H), 7.74-7.66 (m, 4H), 7.48 (s, 1H). HRMS (ESI-TOF): Calcd. For $C_{16}H_9F_2N_2O$ [M+H]$^+$: 283.0683. Found: 283.0684.

Compound Compound III-6:

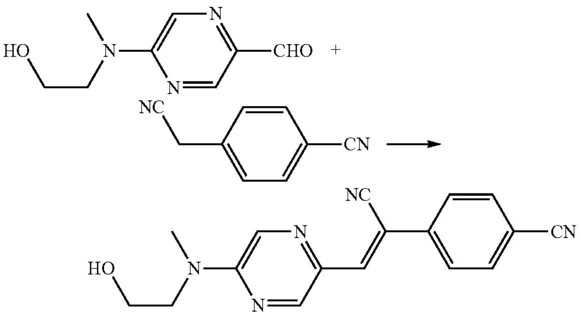

III-6

Wherein compound 5-(N-methyl-N-(2-hydroxyethyl) amino) pyrazine-2-carbaldehyde:

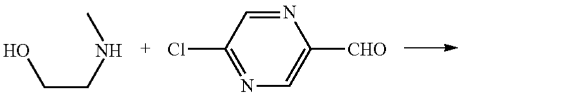

-continued

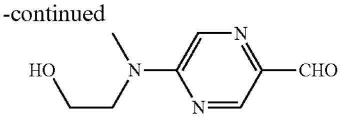

To a stirring solution of N-methyl-N-(2-hydroxyethyl) amino (2.6 g, 35 mmol) and 5-chloro-pyrazine-2-carbaldehyde (0.50 g, 3.5 mmol) in 20 mL dry $CH_3CN$, $K_2CO_3$ (0.71 g, 5.3 mmol) was added in one portion. The mixture was heated to reflux under Ar atmosphere. The mixture was heated to refluxed for 24 h. Upon completing the reaction, the reaction mixture was cooled to room temperature and the organic liquid was removed under reduce pressure. Then the residue was dissolved in 100 mL DCM and the organic phase was washed with water and brine (2×100 ml). Upon drying over anhydrous $Na_2SO_4$ and evaporation under reduced pressure, the residue was purified by column chromatography on silica gel to afford target compound. (0.48 g, 76%). $^1$H NMR (400 MHz, $CDCl_3$): δ 9.88 (s, 1H), 8.62 (d, J=1.2 Hz, 1H), 8.14 (d, J=1.1 Hz, 1H), 3.92 (m, 2H), 3.88-3.83 (m, 2H), 3.28 (s, 3H). HRMS (ESI-TOF): Calcd. For $C_8H_{12}N_3O_2$ $[M+H]^+$: 182.1. Found: 182.1.

Compound III-6 was synthesized with reference to the synthetic method of compound III-1 (0.36 g, 96%). $^1$H NMR (400 MHz, $CDCl_3$): δ 8.39 (s, 1H), 8.30 (s, 1H), 7.80 (d, J=8.5 Hz, 2H), 7.72 (d, J=8.4 Hz, 2H), 7.51 (s, 1H), 3.93 (t, J=4.9 Hz, 2H), 3.88-3.83 (m, 2H), 3.29 (s, 3H). HRMS (ESI-TOF): Calcd. For $C_{17}H_{16}N_5O$ $[M+H]^+$: 306.1355. Found: 306.1357.

Compound III-7

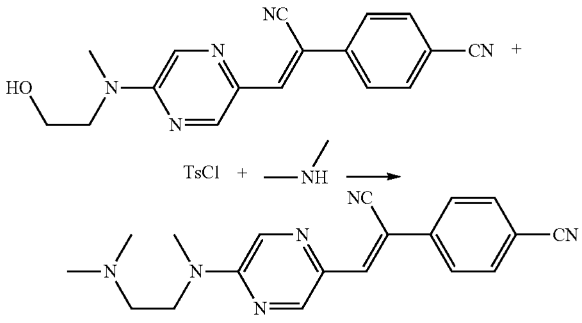

III-7

With reference to the synthetic method of compound III-4, (0.21 g, 67%)$_{\circ}$ $^1$H NMR (400 MHz, DMSO-$d_6$): δ 8.37 (d, J=5.2 Hz, 2H), 8.06 (s, 1H), 8.00-7.85 (m, 4H), 3.77 (t, J=6.5 Hz, 2H), 3.20 (s, 3H), 2.56 (m, 2H), 2.23 (s, 6H). HRMS (ESI-TOF): Calcd. For $C_{19}H_{21}N_6[M+H]^+$: 333.1828. Found: 333.1829.

Compound 11-8:

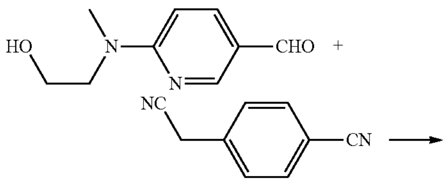

-continued

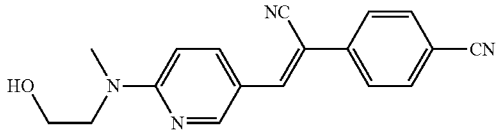

III-8

Wherein, compound 6-(N-methyl-N-(2-hydroxyethyl) amino) pyridine-2-carbaldehyde:

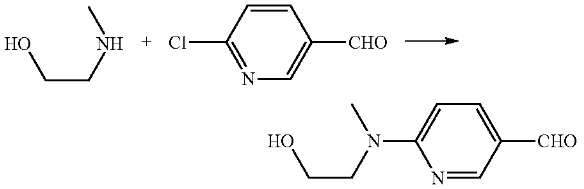

With reference to the synthetic method of Compound 5-(N-methyl-N-(2-hydroxyethyl)amino) pyrazine-2-carbaldehyde: (0.45 g, 68%) $^1$H NMR (400 MHz, $CDCl_3$): δ=9.69 (s, 1H), 8.43 (d, J=2.1 Hz, 1H), 7.86 (dd, J=9.0, 2.3 Hz, 1H), 6.56 (d, J=9.1 Hz, 1H), 3.86-3.79 (m, 4H), 3.15 (s, 3H). HRMS (ESI-TOF): Calcd. For $C_9H_{13}O_2N_2$ $[M+H]^+$: 181.1. Found: 181.1.

Compound III-8 was synthesized with reference to the synthetic method of compound III-1, (0.39 g, 89%)$_{\circ}$ $^1$H NMR (400 MHz, DMSO-$d_6$): δ=8.54 (d, J=4.0 Hz, 1H), 8.30 (dd, J=9.3, 2.5 Hz, 1H), 8.03 (s, 1H), 7.92 (d, J=8.0 Hz, 2H), 7.85 (d, J=8.0 Hz, 2H), 6.84 (d, J=8.0 Hz, 1H), 4.77 (t, J=5.4 Hz, 1H), 3.67 (t, J=5.3 Hz, 2H), 3.60 (q, J=5.4 Hz, 2H), 3.15 (s, 3H). HRMS (ESI-TOF): Calcd. For $C_{18}H_{27}N_4O$ $[M+H]^+$: 305.1402. Found: 305.1401.

Compound III-9:

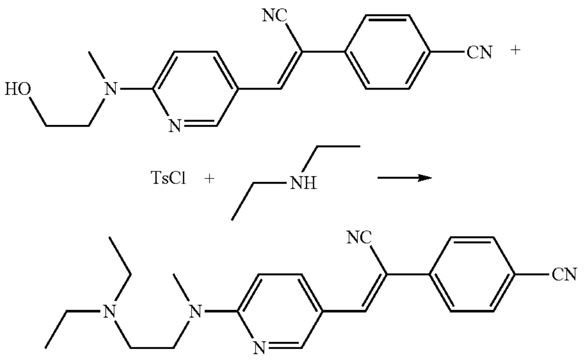

III-9

With reference to the synthetic method of compound III-4, (0.31 g, 92%)$_{\circ}$ $^1$H NMR (400 MHz, DMSO-$d_6$): δ=8.55 (d, J=4.0 Hz, 1H), 8.31 (dd, J=9.3, 2.5 Hz, 1H), 8.05 (s, 1H), 7.93 (d, J.=8.0 Hz, 2H), 7.84 (d, J=8.0 Hz, 2H), 6.85 (d, J=8.0 Hz, 1H), 4.78 (t, J=5.4 Hz, 1H), 3.67 (t, J=5.3 Hz, 2H), 3.60 (q, J=5.4 Hz, 2H), 3.17 (t, J=8.0 Hz, 4H), 1.17 (t, J=8.0 Hz, 6H). HRMS (ESI-TOF): Calcd. For $C_{22}H_{26}N_5$ $[M+H]^+$: 360.2188. Found: 360.2187.

Compound III-10:

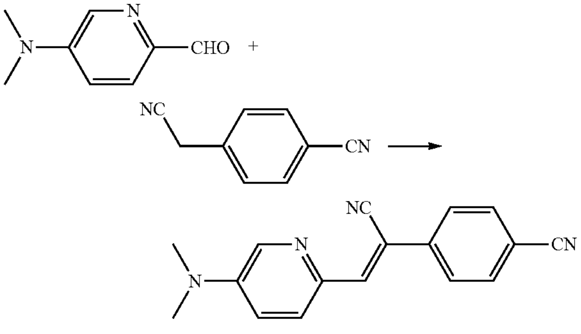

III-10

Wherein, Compound 4-(N,N-dimethylamino)-pyrazine-6-carbaldehyde

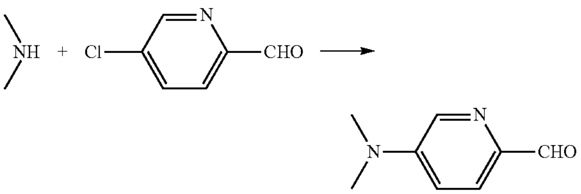

With reference to the synthetic method of compound III-4, (0.31 g, 49%). $^{1}H$ NMR (400 MHz, DMSO-$d_6$): δ=9.86 (d, J=0.6 Hz, 1H), 8.17 (d, J=2.9 Hz, 1H), 7.83 (d, J=8.9 Hz, 1H), 6.94 (dd, J=8.8, 2.9 Hz, 1H), 3.10 (s, 6H). HRMS (ESI-TOF): Calcd. For $C_8H_{11}N_2O$ $[M+H]^+$: 151.1. Found: 151.1.

Compound III-10 was synthesised with reference to the synthetic method of compound III-1, (0.36 g, 96%). $^{1}H$ NMR (400 MHz, DMSO-$d_6$): δ=9.86 (d, J=0.6 Hz, 1H), 8.26 (s, 1H), 8.17 (d, J=2.9 Hz, 1H), 7.83 (d, J=8.9 Hz, 1H), 7.46 (m, 4H), 6.94 (dd, J=8.8, 2.9 Hz, 1H), 3.10 (s, 6H). HRMS (ESI-TOF): Calcd. For $C_{17}H$ is $N_4$ $[M+H]^+$: 275.1297. Found: 275.1298.

Compound 11:

Compound III-11:

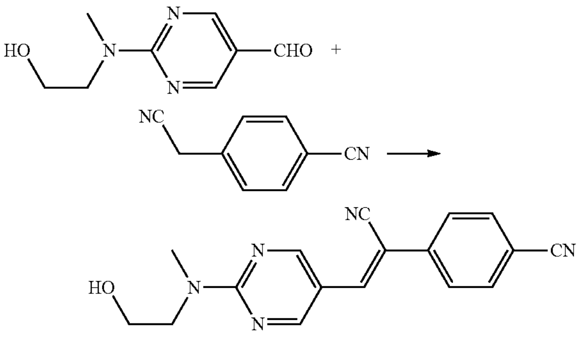

III-11

Wherein, compound 2-(N-methyl-N-(2-hydroxyethyl) amino) pyrimidine-5-carbaldehyde:

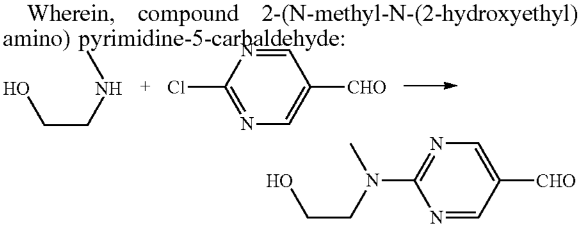

With reference to the synthetic method of compound III-4, (0.42 g, 72%). $^{1}H$ NMR (400 MHz, DMSO-$d_6$): δ=9.89 (s, 1H), 8.73 (s, 2H), 3.64 (t, J=8.9 Hz, 2H), 3.45 (t, J=8.8 Hz, 2H), 3.10 (s, 3H). HRMS (ESI-TOF): Calcd. For $C_8H_{12}N_3O$ $[M+H]^+$: 182.1. Found: 182.1.

Compound III-11 was synthesised with reference to the synthetic method of compound III-1, (0.36 g, 96%)。 $^{1}H$ NMR (400 MHz, DMSO-$d_6$): δ=8.26 (s, 1H), 8.73 (s, 2H), 7.64 (m, 4H), 3.64 (t, J=8.9 Hz, 2H), 3.44 (t, J=8.8 Hz, 2H), 3.11 (s, 3H). HRMS (ESI-TOF): Calcd. For $C_{17}H_{16}N_5O$ $[M+H]^+$: 306.1355. Found: 306.1356.

Compound 12:

Compound III-12:

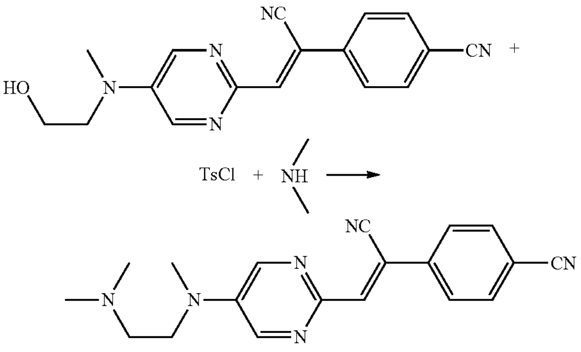

III-12

Wherein, compound 5-(N-methyl-N-(2-hydroxyethyl) amino) pyrimidine-2-carbaldehyde:

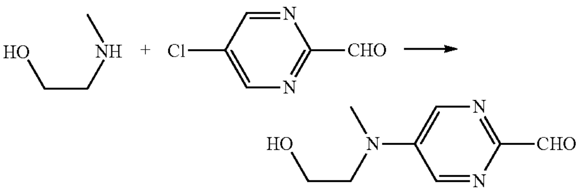

With reference to the synthetic method of compound III-4, (0.42 g, 72%)。 $^{1}H$ NMR (400 MHz, DMSO-$d_6$): δ=9.98 (s, 1H), 8.21 (s, 2H), 3.64 (t, J=8.9 Hz, 2H), 3.44 (t, J=8.8 Hz, 2H), 3.12 (s, 3H). HRMS (ESI-TOF): Calcd. For $C_8H_{12}N_3O_2$$[M+H]^+$: 182.1. Found: 182.1.

4-(1-cyano-2-(5-((2-hydroxyethyl)(methyl)amino) pyrimidin-2-yl)vinyl)benzonitrile1

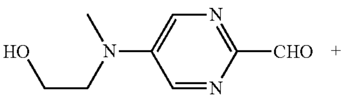

-continued

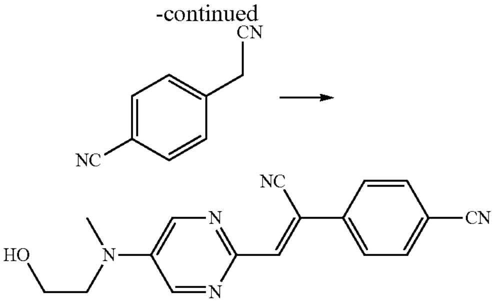

With reference to the synthetic method of compound III-1, (0.56 g, 89%). $^1H$ NMR (400 MHz, DMSO-$d_6$): δ=8.21 (s, 2H), 7.99 (s, 1H), 7.64 (s, 4H), 3.64 (t, J=8.9 Hz, 2H), 3.44 (t, J=8.8 Hz, 2H), 3.12 (s, 3H). HRMS (ESI-TOF): Calcd. For $C_{17}H_6N_5O$ $[M+H]^{30}$: 306.1. Found: 306.1.

Compound III-12 was synthesised with reference to the synthetic method of compound III-4, (0.36 g, 96%). $^1H$ NMR (400 MHz, DMSO-$d_6$): δ=8.21 (s, 2H), 7.99 (s, 1H), 7.64 (s, 4H), 3.77 (t, J=6.5 Hz, 2H), 3.20 (s, 3H), 2.56 (m, 2H), 2.23 (s, 6H). HRMS (ESI-TOF): Calcd. For $C_{19}H_{21}N_6$ $[M+H]^{30}$: 333.1828. Found: 333.1829.

Compound 13:

Compound III-13:

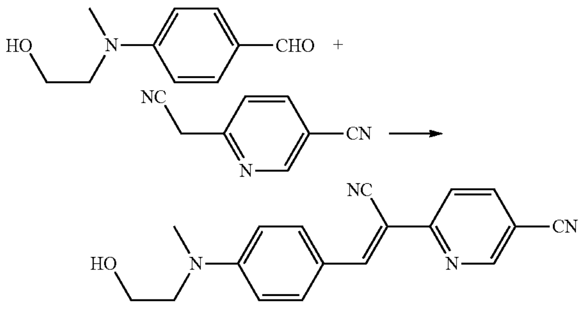

III-13

Wherein, 5-cyano-2-acetonitrile-pyridine: C-55 C3

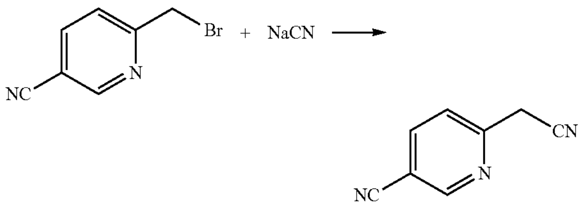

To a stirring solution of 2-(bromomethyl)-benzonitrile (0.50 g, 2.5 mmol) in 50 mL THF, 10 ml NaCN aqueous solution (2 M) was added. The mixture was reflexed for 12 h under Ar atmosphere. Upon cooling to room temperature, the reaction mixture was extracted with DCM (3×100 ml). The organic phase was washed with water and brine (2×100 ml). Upon drying over anhydrous $Na_2SO_4$ and evaporation under reduced pressure, the residue was purified by column chromatography on silica gel to afford target compound. (0.19 g, 56%)$_0$'H NMR (400 MHz, DMSO-$d_6$): δ=8.78 (s, 1H), 7.95 (m, 1H), 7.56 (m, 1H), 4.01 (s, 2H). HRMS (ESI-TOF): Calcd. For $C_8H_6N_3$ $[M+H]^+$: 144.1. Found: 144.1.

Compound III-13 was synthesised with reference to the synthetic method of compound III-1, (0.45 g, 95%). $^1H$ NMR (400 MHz, DMSO-$d_6$): δ=8.78 (s, 1H), 8.21 (s, 1H), 7.94 (m, 1H), 7.86 (d, J=8.0 Hz, 2H), 7.57 (m, 1H), 6.80 (d, J=8.0 Hz, 2H), 3.64 (t, J=8.9 Hz, 2H), 3.44 (t, J=8.8 Hz, 2H), 3.12 (s, 3H). HRMS (ESI-TOF): Calcd. For $C_{18}H_{17}N_4O$ $[M+H]^+$: 305.1402. Found: 305.1403.

Compound 14:

Compound III-14:

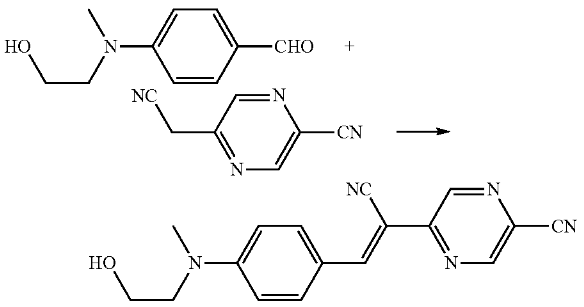

III-14

Wherein, 5-cyano-2-acetonitrile-pyrazine:

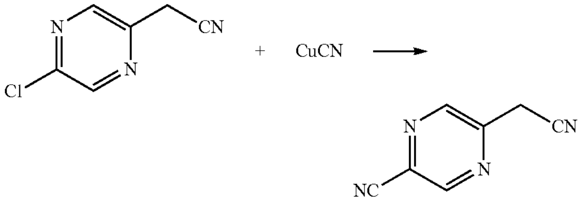

To a stirring solution of 2-(5-chloropyrazin-2-yl)acetonitrile (0.32 g, 2.0 mmol) in dry 30 mL DMSO, CuCN (0.93 g, 10.0 mmol) was added in one portation. The mixture was heated for 12 h under Ar atmosphere. Upon cooling to room temperature, the reaction mixture was poured into 100 mL water, then extracted with DCM (4×50 ml). The organic phase was washed with water and brine (2×100 ml). Upon drying over anhydrous $Na_2SO_4$ and evaporation under reduced pressure, the residue was purified by column chromatography on silica gel to afford target compound (0.20 g, 69%). $^1H$ NMR (400 MHz, DMSO-$d_6$): δ=8.60 (s, 1H), 8.48 (s, 1H), 3.92 (s, 2H). HRMS (ESI-TOF): Calcd. For $C_7H_5N_4$ $[M+H]^+$: 145.1. Found: 145.1.

Compound III-14 was synthesised with reference to the synthetic method of compound III-1, (0.25 g, 91%). $^1H$ NMR (400 MHz, DMSO-$d_6$): δ=8.60 (s, 1H), 8.48 (s, 1H), 8.11 (s, 1H), 7.81 (d, J=8.2 Hz, 2H), 6.84 (d, J=8.2 Hz, 2H), 3.60 (t, J=9.2 Hz, 2H), 3.46 (t, J=9.2 Hz, 2H), 3.12 (s, 3H). HRMS (ESI-TOF): Calcd. For $C_{17}H_{16}N_5O$ $[M+H]^+$: 306.1355. Found: 306.1354.

Compound 15:

Compound III-15:

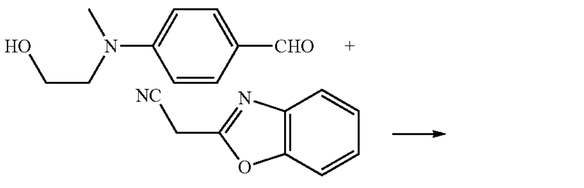

-continued

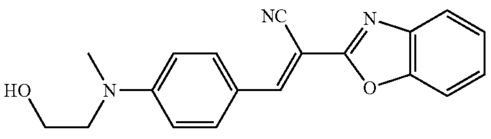

III-15

With reference to the synthetic method of compound III-1, (0.25 g, 91%) $^{1}$H NMR (400 MHz, DMSO-$d_6$): δ=8.22 (s, 1H), 8.00 (d, J=9.1 Hz, 1H), 7.77-7.69 (m, 1H), 7.43-7.34 (m, 1H), 6.88 (d, J=9.1 Hz, 1H), 4.81 (t, J=5.2 Hz, 1H), 3.64-3.52 (m, 3H), 3.09 (s, 1H). LR-HRMS (ESI-TOF): Calcd. For $C_{19}H_{18}N_3O_2$ $[M+H]^+$: 320.1399. Found: 320.1397.

Compound II-16:

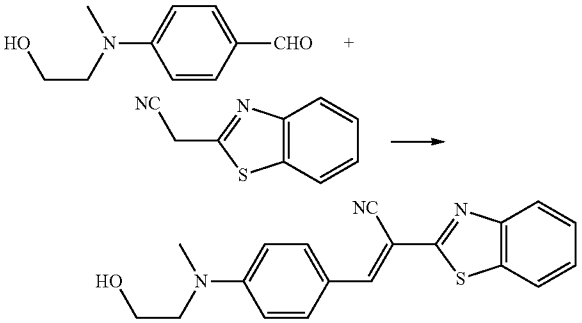

III-16

With reference to the synthetic method of compound III-1, (0.29 g, 94%). $^{1}$H NMR (400 MHz, DMSO-$d_6$): δ=8.11 (2H, d, J=10.4 Hz), 7.99 (3H, dd, J=8.6, 3.0 Hz), 7.54 (1H, dd, J=8.0, 8.0 Hz), 7.44 (1H, dd, J=8.0, 8.0 Hz), 6.88 (2H, d, J=9.2 Hz), 4.82 (1H, bt, t, J=5.2 Hz), 3.60 (2H, t, J=5.2 Hz), 3.56 (2H, t, J=5.2 Hz), 3.09 (3H, s). LR-HRMS (ESI-TOF): Calcd. For $C_{19}H_{18}N_3OS$ $[M+H]^+$: 336.1171. Found: 336.1170.

Compound III-17:

Compound III-17:

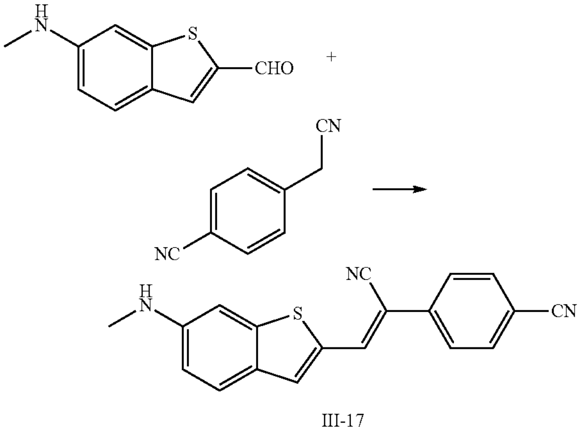

III-17

Wherein, 6-(methylamino)benzo[b]thiophene-2-carbaldehyde:

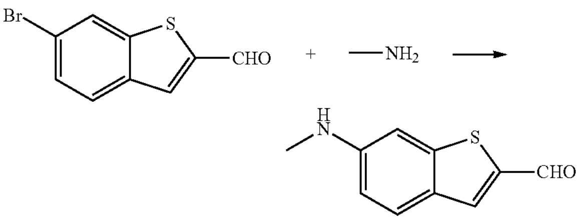

6-(methylamino)benzo[b]thiophene-2-carbaldehyde (0.42 g, 1.7 mmol), 40% aqueous N,N-Dimethylethylamin solution (lg, 8.9 mmol), CuI (13.9 mg, 0.073 mmol), $K_3PO_4 \cdot H_2O$ (155.4 mg, 0.73 mmol), 1 mL 33% aqueous methylamine solution and stirring bar was sealed in a screwed tube and stirred at 60° C. for 12 h. upon cooling to room temperature, the mixture was poured into 50 mL water. The organic layer was separated and the aqueous layer was extracted with DCM (3×100 ml). Combined the organic phase and dried over anhydrous $Na_2SO_4$ and evaporation under reduced pressure, the residue was purified by column chromatography on silica gel to afford target compound(0.23 g, 68%). $^{1}$H NMR (400 MHz, DMSO-$d_6$): δ=9.92 (1H, s), 8.14 (1H, s), 7.82 (1H, d, J=9.1 Hz), 7.18 (1H, d, J=2.1 Hz), 7.01 (1H, dd, J=9.1, 2.3 Hz), 3.05 (3H, s). HRMS (ESI-TOF): Calcd. For $C_{10}H_{10}NOS$ $[M+H]^+$: 192.0. Found: 192.0.

Compound III-17 was synthesised with reference to the synthetic method of compound III-1, (0.29 g, 94%). $^{1}$H NMR (400 MHz, DMSO-$d_6$): δ=8.45 (s, 1H), 7.92 (d, J=8.6 Hz, 2H), 7.85 (d, J=8.3 Hz, 3H), 7.73 (dd, J=8.6, 3.9 Hz, 1H), 7.21 (d, J=1.9 Hz, 1H), 7.21 (d, J=1.9 Hz, 1H), 6.96 (dd, J=9.1, 2.3 Hz, 1H), 3.05 (s, 3H). HRMS (ESI-TOF): Calcd. For $C_{19}H_{14}N_3S$ $[M+H]^+$: 360.1171. Found: 360.1173.

Compound III-18:

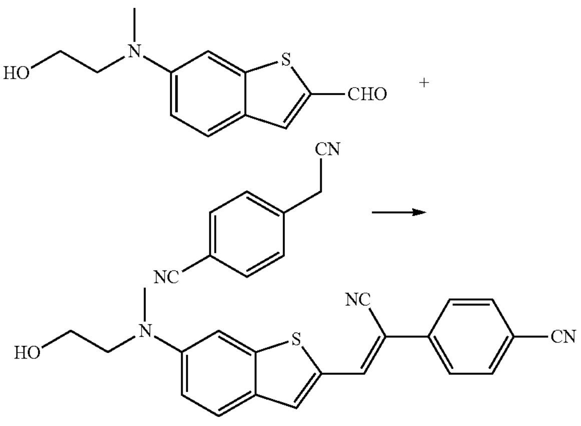

III-18

Wherein, 6-((2-hydroxyethyl)(methyl)amino)benzo[b]thiophene-2-carbaldehyde:

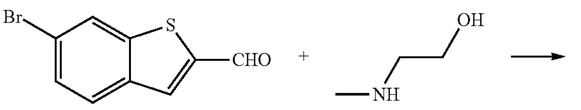

-continued

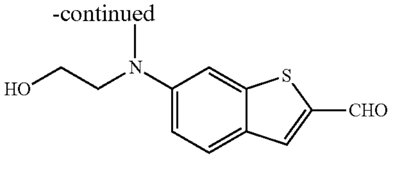

With reference to the synthetic method of compound 6-(methylamino)benzo[b]thiophene-2-carbaldehyde, (0.54 g, 79%). $^1$H NMR (400 MHz, DMSO-$d_6$): δ=9.91 (s, 1H), 8.14 (s, 1H), 7.81 (d, J=5.2 Hz, 1H), 7.17 (d, J=2.0 Hz, 1H), 7.01 (dd, J=2.0, 8.8 Hz, 1H), 4.76 (t, J=5.6 Hz, 1H), 3.58 (t, J=4.2 Hz, 2H), 3.52 (t, J=4.2 Hz, 2H), 3.04 (s, 3H). HRMS (ESI-TOF):m/z Calcd. For $C_{12}H_{14}NO_2S$, $[M+H]^+$: 235.1. Found 236.1.

Compound III-18 was synthesised with reference to the synthetic method of compound III-1, (0.21 g, 95%). $^1$H NMR (400 MHz, DMSO-$d_6$): δ=8.45 (s, 1H), 7.92 (d, J=8.6 Hz, 2H), 7.85 (d, J=8.3 Hz, 3H), 7.73 (dd, J=8.6, 3.9 Hz, 1H), 7.21 (d, J=1.9 Hz, 1H), 7.21 (d, J=1.9 Hz, 1H), 6.96 (dd, J=9.1, 2.3 Hz, 1H), 3.63-3.57 (m, 2H), 3.52 (t, J=5.7 Hz, 2H), 3.05 (s, 3H). HRMS (ESI-TOF): Calcd. For $C_{21}H_{19}N_3OS$ $[M+H]^+$: 360.1171. Found: 360.1173.

Compound III-19:

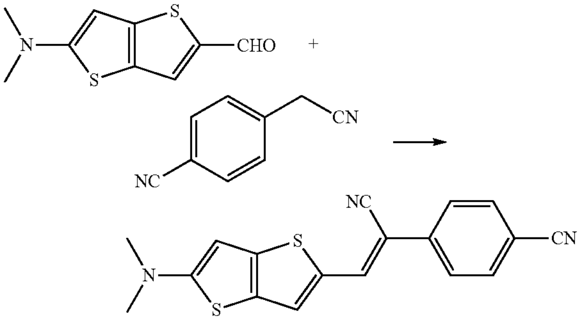

III-19

Wherein, 5-(N,N-dimethylamino)-thieno[3,2-b]thiophene-2-carbaldehyde

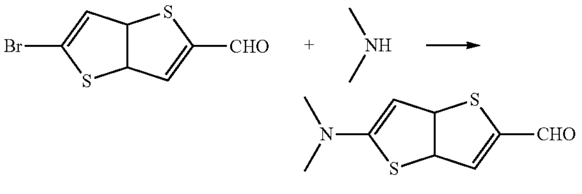

With reference to the synthetic method of compound 6-((2-hydroxyethyl)(methyl)amino)benzo[b]thiophene-2-carbaldehyde, (0.54 g, 79%)。 $^1$H NMR (400 MHz, DMSO-$d_6$): δ=9.66 (s, 1H), 8.05 (s, 1H), 6.30 (s, 1H), 4.88 (bt, 1H), 3.07 (s, 6H). HRMS (ESI-TOF): m/z Calcd. For $C_9H_{12}NOS_2$ $[M+H]^+$: 214.0; found 214.0.

Compound III-19 was synthesised with reference to the synthetic method of compound III-1, (0.31 g, 90%)。 $^1$H NMR (400 MHz, DMSO-$d_6$): δ=8.34 (s, 1H), 7.86 (d, J=8.0 Hz, 2H), 7.81 (s, 1H), 7.77 (d, J=8.0 Hz, 2H), 6.32 (s, 1H), 4.88 (t, J=4.0 Hz, 1H), 3.08 (s, 6H). HRMS (ESI-TOF): Calcd. For $C_{18}H_{14}N_3S_2$ $[M+H]^+$: 336.0629. Found: 336.0630.

Compound III-20:

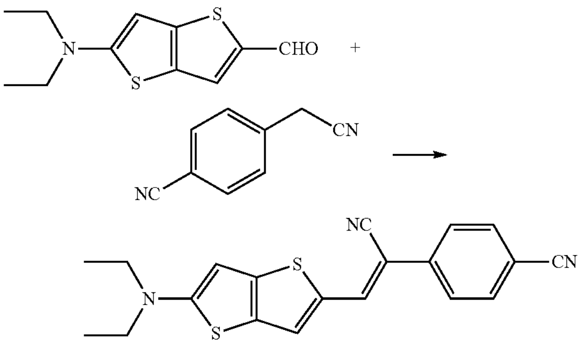

III-20

Wherein, 5-(N,N-diethylamino)-thieno[3,2-b]thiophene-2-carbaldehyde:

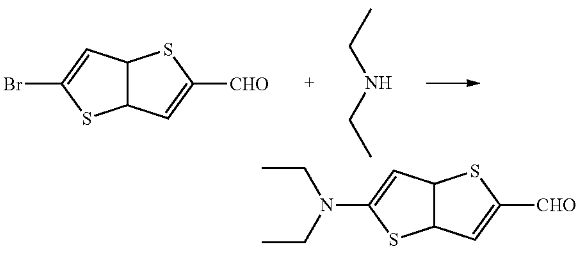

With reference to the synthetic method of compound 5-(N,N-dimethylamino)-thieno[3,2-b]thiophene-2-carbaldehyde, (0.44 g, 75%). $^1$H NMR (400 MHz, DMSO-$d_6$): δ=9.78 (s, 1H), 8.09 (s, 1H), 6.30 (s, 1H), 4.87 (bt, 1H), 3.27 (t, J=8.4 Hz, 4H), 1.26 (t, J=8.4 Hz, 4H). HRMS (ESI-TOF): m/z Calcd. For $C_9H_{12}NOS_2$ $[M+H]^{30}$: 214.0; found 214.0.

Compound III-20 was synthesised with reference to the synthetic method of compound III-1, (0.31 g, 90%). $^1$H NMR (400 MHz, DMSO-$d_6$): δ=8.34 (s, 1H), 7.86 (d, J=8.0 Hz, 2H), 7.81 (s, 1H), 7.77 (d, J=8.0 Hz, 2H), 6.32 (s, 1H), 4.88 (t, J=4.0 Hz, 1H), 3.27 (t, J=8.4 Hz, 4H), 1.26 (t, J=8.4 Hz, 4H). HRMS (ESI-TOF): Calcd. For $C_{20}H_{18}N_3S_2$ $[M+H]^+$: 364.0942. Found: 364.0943.

Compound III-21:

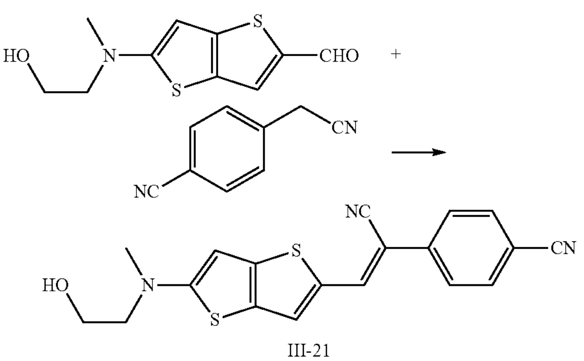

III-21

Wherein, 5-((2-hydroxyethyl)(methyl)amino)-thieno[3,2-b]thiophene-2-carbaldehyde:

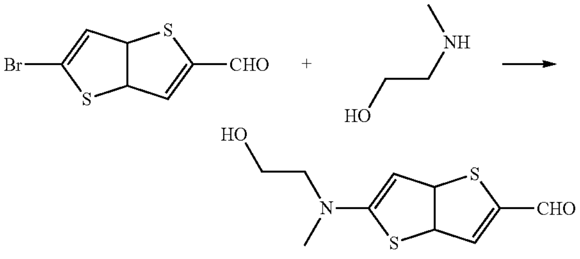

With reference to the synthetic method of compound 6-((2-hydroxyethyl)(methyl)amino)benzo[b]thiophene-2-carbaldehyde, (0.44 g, 75%). $^1$H NMR (400 MHz, DMSO-$d_6$): δ=9.66 (s, 1H), 8.05 (s, 1H), 6.30 (s, 1H), 4.88 (bt, 1H), 3.64 (t, J=5.6 Hz, 2H), 3.44 (t, J=5.6 Hz, 2H), 3.07 (s, 3H). HRMS (ESI-TOF): m/z Calcd. For $C_{10}H_{12}NO_2S_2$ $[M+H]^+$: 241.0; found 242.0.

Compound III-21 was synthesised with reference to the synthetic method of compound III-1, (0.31 g, 90%)$_0$ 1H NMR (400 MHz, DMSO-$d_6$): δ 8.34 (s, 1H), 7.86 (d, J=8.0 Hz, 2H), 7.81 (s, 1H), 7.77 (d, J=8.0 Hz, 2H), 6.32 (s, 1H), 4.88 (t, J=4.0 Hz, 1H), 3.65 (q, J=5.5 Hz, 2H), 3.44 (t, J=5.5 Hz, 2H), 3.34 (s, 1H), 3.08 (s, 3H). HRMS (ESI-TOF): Calcd. For $C_{19}H_{16}N_3OS_2$ $[M+H]^+$: 366.0735. Found: 366.0736.

It will be understood that the dosages, reaction conditions, etc., in the examples are approximate values unless noted otherwise, and they can be exactly changed base on the situations to obtain similar results. All of the professional terms used in the Description, except those specially defined, have identical meanings to those known by persons skilled in the art. All the references referred to are incorporated into the application as a whole. The preferable embodiments are only exemplified for the illustration of the invention. Those skilled in the art can adopt similar methods or materials to obtain similar results. All the changes and modifications are within the scope of the attached claims.

What is claimed is:

1. A nucleic acid aptamer comprising a sequence of any of SEQ ID NOs: 1-3, 6-19, 21-23.

* * * * *

SEQUENCE LISTING

```
<160> NUMBER OF SEQ ID NOS: 143

<210> SEQ ID NO 1
<211> LENGTH: 49
<212> TYPE: RNA
<213> ORGANISM: Artificial Sequence
<220> FEATURE:
<223> OTHER INFORMATION: Synthetic sequence

<400> SEQUENCE: 1

uccccaaucg uggcgugucg gccugcuucg gcaggcacug gcgccggga                49


<210> SEQ ID NO 2
<211> LENGTH: 101
<212> TYPE: RNA
<213> ORGANISM: Artificial Sequence
<220> FEATURE:
<223> OTHER INFORMATION: Synthetic sequence

<400> SEQUENCE: 2

uugccaugug uauguggguu cgcccacaua cucugaugau ccccaaucgu ggcgugucgg     60

ccugcuucgg caggcacugg cgccgggauc auucauggca a                        101


<210> SEQ ID NO 3
<211> LENGTH: 114
<212> TYPE: RNA
<213> ORGANISM: Artificial Sequence
<220> FEATURE:
<223> OTHER INFORMATION: Synthetic sequence

<400> SEQUENCE: 3

gcccggauag cucagucggu agagcagcgc ugccaaucgu ggcgugucgg ccugcuucgg     60

caggcacugg cgccgcagcg cggguccagg guucaagucc cuguucgggc gcca          114


<210> SEQ ID NO 4
<211> LENGTH: 105
<212> TYPE: RNA
<213> ORGANISM: Artificial Sequence
<220> FEATURE:
<223> OTHER INFORMATION: Synthetic sequence

<400> SEQUENCE: 4
```

-continued uugccaugug uaugugggu cgcccacaua cucugaugau ccagacgguc ggguccagau 60
auucguaucu gucgaguaga gugugggcug gaucauucau ggcaa 105

<210> SEQ ID NO 5
<211> LENGTH: 234
<212> TYPE: RNA
<213> ORGANISM: Artificial Sequence
<220> FEATURE:
<223> OTHER INFORMATION: Synthetic sequence

<400> SEQUENCE: 5
uugccaugug uaugugggag acggucgggu ccaucugaga cggucggguc cagauauucg 60
uaucugucga guagagugug ggcucagaug ucgaguagag ugugggcucc cacauacucu 120
gaugauccag acggucgggu ccaucugaga cggucggguc cagauauucg uaucugucga 180
guagagugug ggcucagaug ucgaguagag ugugggcugg aucauucaug gcaa 234

<210> SEQ ID NO 6
<211> LENGTH: 53
<212> TYPE: RNA
<213> ORGANISM: Artificial Sequence
<220> FEATURE:
<223> OTHER INFORMATION: Synthetic sequence

<400> SEQUENCE: 6
ggcccccaau cguggcgugu cggccugcuu cggcaggcac uggcgccggg gcc 53

<210> SEQ ID NO 7
<211> LENGTH: 55
<212> TYPE: RNA
<213> ORGANISM: Artificial Sequence
<220> FEATURE:
<223> OTHER INFORMATION: Synthetic sequence

<400> SEQUENCE: 7
ggccccccaa ucguggcgug ucggccugcu ucggcaggca cuggcgccgg gggcc 55

<210> SEQ ID NO 8
<211> LENGTH: 144
<212> TYPE: RNA
<213> ORGANISM: Artificial Sequence
<220> FEATURE:
<223> OTHER INFORMATION: Synthetic sequence

<400> SEQUENCE: 8
uugccaugug uaugugggu cgcccacaua cucugaugau ccccaaucgu ggcgugucgg 60
ccucucccaa ucguggcgug ucggccucuc uucggagagg cacuggcgcc ggagaggcac 120
uggcgccggg aucauucaug gcaa 144

<210> SEQ ID NO 9
<211> LENGTH: 226
<212> TYPE: RNA
<213> ORGANISM: Artificial Sequence
<220> FEATURE:
<223> OTHER INFORMATION: Synthetic sequence

<400> SEQUENCE: 9
uugccaugug uaugugggu cgcccacaua cucugaugau ccccaaucgu ggcgugucgg 60
ccucucccaa ucguggcgug ucggccucuc ccaaucgugg cgugucggcc ucucccaauc 120
guggcguguc ggccucucuu cggagaggca cuggcgccgg agaggcacug gcgccggaga 180

-continued

```
ggcacuggcg ccggagaggc acuggcgccg ggaucauuca uggcaa                 226


<210> SEQ ID NO 10
<211> LENGTH: 390
<212> TYPE: RNA
<213> ORGANISM: Artificial Sequence
<220> FEATURE:
<223> OTHER INFORMATION: Synthetic sequence

<400> SEQUENCE: 10

uugccaugug uaugugggu u cgcccacaua cucugaugau ccccaaucgu ggcgugucgg    60

ccucucccaa ucguggcgug ucggccucuc ccaaucgugg cgugucggcc ucucccaauc   120

guggcguguc ggccucuccc aaucguggcg ugucggccuc ucccaaucgu ggcgugucgg   180

ccucucccaa ucguggcgug ucggccucuc ccaaucgugg cgugucggcc ucucuucgga   240

gaggcacugg cgccggagag gcacuggcgc cggagaggca cuggcgccgg agaggcacug   300

gcgccggaga ggcacuggcg ccggagaggc acuggcgccg gagaggcacu ggcgccggag   360

aggcacuggc gccgggauca uucauggcaa                                    390


<210> SEQ ID NO 11
<211> LENGTH: 718
<212> TYPE: RNA
<213> ORGANISM: Artificial Sequence
<220> FEATURE:
<223> OTHER INFORMATION: Synthetic sequence

<400> SEQUENCE: 11

uugccaugug uaugugggu u cgcccacaua cucugaugau ccccaaucgu ggcgugucgg    60

ccucucccaa ucguggcgug ucggccucuc ccaaucgugg cgugucggcc ucucccaauc   120

guggcguguc ggccucuccc aaucguggcg ugucggccuc ucccaaucgu ggcgugucgg   180

ccucucccaa ucguggcgug ucggccucuc ccaaucgugg cgugucggcc ucucccaauc   240

guggcguguc ggccucuccc aaucguggcg ugucggccuc ucccaaucgu ggcgugucgg   300

ccucucccaa ucguggcgug ucggccucuc ccaaucgugg cgugucggcc ucucccaauc   360

guggcguguc ggccucuccc aaucguggcg ugucggccuc ucccaaucgu ggcgugucgg   420

ccucucuucg gagaggcacu ggcgccggag aggcacuggc gccggagagg cacuggcgcc   480

ggagaggcac uggcgccgga gaggcacugg cgccggagag gcacuggcgc cggagaggca   540

cuggcgccgg agaggcacug gcgccggaga ggcacuggcg ccggagaggc acuggcgccg   600

gagaggcacu ggcgccggag aggcacuggc gccggagagg cacuggcgcc ggagaggcac   660

uggcgccgga gaggcacugg cgccggagag gcacuggcgc cgggaucauu cauggcaa     718


<210> SEQ ID NO 12
<211> LENGTH: 1374
<212> TYPE: RNA
<213> ORGANISM: Artificial Sequence
<220> FEATURE:
<223> OTHER INFORMATION: Synthetic sequence

<400> SEQUENCE: 12

uugccaugug uaugugggu u cgcccacaua cucugaugau ccccaaucgu ggcgugucgg    60

ccucucccaa ucguggcgug ucggccucuc ccaaucgugg cgugucggcc ucucccaauc   120

guggcguguc ggccucuccc aaucguggcg ugucggccuc ucccaaucgu ggcgugucgg   180

ccucucccaa ucguggcgug ucggccucuc ccaaucgugg cgugucggcc ucucccaauc   240

guggcguguc ggccucuccc aaucguggcg ugucggccuc ucccaaucgu ggcgugucgg   300
```

ccucucccaa ucguggcgug ucggccucuc ccaaucgugg cgugucggcc ucucccaauc 360
guggcguguc ggccucuccc aaucguggcg ugucggccuc ucccaaucgu ggcgugucgg 420
ccucucccaa ucguggcgug ucggccucuc ccaaucgugg cgugucggcc ucucccaauc 480
guggcguguc ggccucuccc aaucguggcg ugucggccuc ucccaaucgu ggcgugucgg 540
ccucucccaa ucguggcgug ucggccucuc ccaaucgugg cgugucggcc ucucccaauc 600
guggcguguc ggccucuccc aaucguggcg ugucggccuc ucccaaucgu ggcgugucgg 660
ccucucccaa ucguggcgug ucggccucuc ccaaucgugg cgugucggcc ucucccaauc 720
guggcguguc ggccucuccc aaucguggcg ugucggccuc ucccaaucgu ggcgugucgg 780
ccucucccaa ucguggcgug ucggccucuc uucggagagg cacuggcgcc ggagaggcac 840
uggcgccgga gaggcacugg cgccggagag gcacuggcgc cggagaggca cuggcgccgg 900
agaggcacug gcgccggaga ggcacuggcg ccggagaggc acuggcgccg gagaggcacu 960
ggcgccggag aggcacuggc gccggagagg cacuggcgcc ggagaggcac uggcgccgga 1020
gaggcacugg cgccggagag gcacuggcgc cggagaggca cuggcgccgg agaggcacug 1080
gcgccggaga ggcacuggcg ccggagaggc acuggcgccg gagaggcacu ggcgccggag 1140
aggcacuggc gccggagagg cacuggcgcc ggagaggcac uggcgccgga gaggcacugg 1200
cgccggagag gcacuggcgc cggagaggca cuggcgccgg agaggcacug gcgccggaga 1260
ggcacuggcg ccggagaggc acuggcgccg gagaggcacu ggcgccggag aggcacuggc 1320
gccggagagg cacuggcgcc ggagaggcac uggcgccggg aucauucaug gcaa 1374

<210> SEQ ID NO 13
<211> LENGTH: 177
<212> TYPE: RNA
<213> ORGANISM: Artificial Sequence
<220> FEATURE:
<223> OTHER INFORMATION: Synthetic sequence

<400> SEQUENCE: 13
cugcaggucg acucuagaaa ggcccccaau cguggcgugu cggccugcuu cggcaggcac 60
uggcgccggg gcccugcagu auucccgggu ucauuagauc cuaagguacc uaauugccua 120
gaaaggcccc caaucguggc gugucggccu gcuucggcag gcacuggcgc cggggcc 177

<210> SEQ ID NO 14
<211> LENGTH: 354
<212> TYPE: RNA
<213> ORGANISM: Artificial Sequence
<220> FEATURE:
<223> OTHER INFORMATION: Synthetic sequence

<400> SEQUENCE: 14
cugcaggucg acucuagaaa ggcccccaau cguggcgugu cggccugcuu cggcaggcac 60
uggcgccggg gcccugcagu auucccgggu ucauuagauc cuaagguacc uaauugccua 120
gaaaggcccc caaucguggc gugucggccu gcuucggcag gcacuggcgc cggggcccug 180
caggucgacu cuagaaaggc ccccaaucgu ggcgugucgg ccugcuucgg caggcacugg 240
cgccggggcc cugcaguauu cccggguuca uuagauccua agguaccuaa uugccuagaa 300
aggcccccaa ucguggcgug ucggccugcu ucggcaggca cuggcgccgg ggcc 354

<210> SEQ ID NO 15
<211> LENGTH: 708
<212> TYPE: RNA

-continued

<213> ORGANISM: Artificial Sequence
<220> FEATURE:
<223> OTHER INFORMATION: Synthetic sequence

<400> SEQUENCE: 15
cugcaggucg acucuagaaa ggcccccaau cguggcgugu cggccugcuu cggcaggcac 60
uggcgccggg gcccugcagu auucccgggu ucauuagauc cuaagguacc uaauugccua 120
gaaaggcccc caaucguggc gugucggccu gcuucggcag gcacuggcgc cggggcccug 180
caggucgacu cuagaaaggc ccccaaucgu ggcgugucgg ccugcuucgg caggcacugg 240
cgccggggcc cugcaguauu cccggguuca uuagauccua agguaccuaa uugccuagaa 300
aggcccccaa ucguggcgug ucggccugcu ucggcaggca cuggcgccgg ggcccugcag 360
gucgacucua gaaaggcccc caaucguggc gugucggccu gcuucggcag gcacuggcgc 420
cggggcccug caguauuccc ggguucauua gauccuaagg uaccuaauug ccuagaaagg 480
cccccaaucg uggcgugucg gccugcuucg gcaggcacug gcgccggggc ccugcagguc 540
gacucuagaa aggcccccaa ucguggcgug ucggccugcu ucggcaggca cuggcgccgg 600
ggcccugcag uauucccggg uucauuagau ccuaagguac cuaauugccu agaaaggccc 660
ccaaucgugg cgugucggcc ugcuucggca ggcacuggcg ccggggcc 708

<210> SEQ ID NO 16
<211> LENGTH: 1416
<212> TYPE: RNA
<213> ORGANISM: Artificial Sequence
<220> FEATURE:
<223> OTHER INFORMATION: Synthetic sequence

<400> SEQUENCE: 16
cugcaggucg acucuagaaa ggcccccaau cguggcgugu cggccugcuu cggcaggcac 60
uggcgccggg gcccugcagu auucccgggu ucauuagauc cuaagguacc uaauugccua 120
gaaaggcccc caaucguggc gugucggccu gcuucggcag gcacuggcgc cggggcccug 180
caggucgacu cuagaaaggc ccccaaucgu ggcgugucgg ccugcuucgg caggcacugg 240
cgccggggcc cugcaguauu cccggguuca uuagauccua agguaccuaa uugccuagaa 300
aggcccccaa ucguggcgug ucggccugcu ucggcaggca cuggcgccgg ggcccugcag 360
gucgacucua gaaaggcccc caaucguggc gugucggccu gcuucggcag gcacuggcgc 420
cggggcccug caguauuccc ggguucauua gauccuaagg uaccuaauug ccuagaaagg 480
cccccaaucg uggcgugucg gccugcuucg gcaggcacug gcgccggggc ccugcagguc 540
gacucuagaa aggcccccaa ucguggcgug ucggccugcu ucggcaggca cuggcgccgg 600
ggcccugcag uauucccggg uucauuagau ccuaagguac cuaauugccu agaaaggccc 660
ccaaucgugg cgugucggcc ugcuucggca ggcacuggcg ccggggcccu gcaggucgac 720
ucuagaaagg cccccaaucg uggcgugucg gccugcuucg gcaggcacug gcgccggggc 780
ccugcaguau ucccggguuc auuagauccu aagguaccua auugccuaga aaggccccca 840
aucguggcgu gucggccugc uucggcaggc acuggcgccg gggcccugca ggucgacucu 900
agaaaggccc ccaaucgugg cgugucggcc ugcuucggca ggcacuggcg ccggggcccu 960
gcaguauucc cggguucauu agauccuaag guaccuaauu gccuagaaag gcccccaauc 1020
guggcguguc ggccugcuuc ggcaggcacu ggcgccgggg cccugcaggu cgacucuaga 1080
aaggccccca aucguggcgu gucggccugc uucggcaggc acuggcgccg gggcccugca 1140
guauucccgg guucauuaga uccuaaggua ccuaauugcc uagaaaggcc cccaaucgug 1200

-continued gcgugucggc cugcuucggc aggcacuggc gccggggccc ugcaggucga cucuagaaag 1260
gcccccaauc guggcguguc ggccugcuuc ggcaggcacu ggcgccgggg cccugcagua 1320
uucccggguu cauuagaucc uaagguaccu aauugccuag aaaggccccc aaucguggcg 1380
ugucggccug cuucggcagg cacuggcgcc ggggcc 1416

<210> SEQ ID NO 17
<211> LENGTH: 263
<212> TYPE: RNA
<213> ORGANISM: Artificial Sequence
<220> FEATURE:
<223> OTHER INFORMATION: Synthetic sequence

<400> SEQUENCE: 17
cugcaggucg acucuagaaa ggcccccaau cguggcgugu cggccucucc caaucguggc 60
gugucggccu cucuucggag aggcacuggc gccggagagg cacuggcgcc ggggcccugc 120
aguauucccg gguucauuag auccuaaggu accuaauugc cuagaaaggc ccccaaucgu 180
ggcgugucgg ccucucccaa ucguggcgug ucggccucuc uucggagagg cacuggcgcc 240
ggagaggcac uggcgccggg gcc 263

<210> SEQ ID NO 18
<211> LENGTH: 526
<212> TYPE: RNA
<213> ORGANISM: Artificial Sequence
<220> FEATURE:
<223> OTHER INFORMATION: Synthetic sequence

<400> SEQUENCE: 18
cugcaggucg acucuagaaa ggcccccaau cguggcgugu cggccucucc caaucguggc 60
gugucggccu cucuucggag aggcacuggc gccggagagg cacuggcgcc ggggcccugc 120
aguauucccg gguucauuag auccuaaggu accuaauugc cuagaaaggc ccccaaucgu 180
ggcgugucgg ccucucccaa ucguggcgug ucggccucuc uucggagagg cacuggcgcc 240
ggagaggcac uggcgccggg gcccugcagg ucgacucuag aaaggccccc aaucguggcg 300
ugucggccuc ucccaaucgu ggcgugucgg ccucucuucg gagaggcacu ggcgccggag 360
aggcacuggc gccggggccc ugcaguauuc ccggguucau uagauccuaa gguaccuaau 420
ugccuagaaa ggcccccaau cguggcgugu cggccucucc caaucguggc gugucggccu 480
cucuucggag aggcacuggc gccggagagg cacuggcgcc ggggcc 526

<210> SEQ ID NO 19
<211> LENGTH: 1052
<212> TYPE: RNA
<213> ORGANISM: Artificial Sequence
<220> FEATURE:
<223> OTHER INFORMATION: Synthetic sequence

<400> SEQUENCE: 19
cugcaggucg acucuagaaa ggcccccaau cguggcgugu cggccucucc caaucguggc 60
gugucggccu cucuucggag aggcacuggc gccggagagg cacuggcgcc ggggcccugc 120
aguauucccg gguucauuag auccuaaggu accuaauugc cuagaaaggc ccccaaucgu 180
ggcgugucgg ccucucccaa ucguggcgug ucggccucuc uucggagagg cacuggcgcc 240
ggagaggcac uggcgccggg gcccugcagg ucgacucuag aaaggccccc aaucguggcg 300
ugucggccuc ucccaaucgu ggcgugucgg ccucucuucg gagaggcacu ggcgccggag 360

-continued

```
aggcacuggc gccggggccc ugcaguauuc ccggguucau uagauccuaa gguaccuaau    420

ugccuagaaa ggcccccaau cguggcgugu cggccucucc caaucguggc gugucggccu    480

cucuucggag aggcacuggc gccggagagg cacuggcgcc ggggcccugc aggucgacuc    540

uagaaaggcc cccaaucgug gcgugucggc cucucccaau cguggcgugu cggccucucu    600

ucggagaggc acuggcgccg gagaggcacu ggcgccgggg cccugcagua uucccggguu    660

cauuagaucc uaagguaccu aauugccuag aaaggccccc aaucguggcg ugucggccuc    720

ucccaaucgu ggcgugucgg ccucucuucg gagaggcacu ggcgccggag aggcacuggc    780

gccggggccc ugcaggucga cucuagaaag gcccccaauc guggcguguc ggccucuccc    840

aaucguggcg ugucggccuc ucuucggaga ggcacuggcg ccggagaggc acuggcgccg    900

gggcccugca guauucccgg guucauuaga uccuaaggua ccuaauugcc uagaaaggcc    960

cccaaucgug gcgugucggc cucucccaau cguggcgugu cggccucucu ucggagaggc   1020

acuggcgccg gagaggcacu ggcgccgggg cc                                 1052
```

<210> SEQ ID NO 20
<211> LENGTH: 101
<212> TYPE: RNA
<213> ORGANISM: Artificial Sequence
<220> FEATURE:
<223> OTHER INFORMATION: Synthetic sequence

<400> SEQUENCE: 20

```
gcccggauag cucagucggu agagcagcgg ccgcgaggaa ggaggucuga ggaggucacu     60

gcggccgcgg guccaggguu caagucccug uucgggcgcc a                        101
```

<210> SEQ ID NO 21
<211> LENGTH: 65
<212> TYPE: RNA
<213> ORGANISM: Artificial Sequence
<220> FEATURE:
<223> OTHER INFORMATION: Synthetic sequence

<400> SEQUENCE: 21

```
uccccaaucg uggcgugucg gcggaagaaa cuguggcacu ucggugccag gcacuggcgc     60

cggga                                                                 65
```

<210> SEQ ID NO 22
<211> LENGTH: 57
<212> TYPE: RNA
<213> ORGANISM: Artificial Sequence
<220> FEATURE:
<223> OTHER INFORMATION: Synthetic sequence

<400> SEQUENCE: 22

```
uccccaaucg uggcgugucg uaagaagagc acguauacgc aauaacuggc gccggga        57
```

<210> SEQ ID NO 23
<211> LENGTH: 196
<212> TYPE: RNA
<213> ORGANISM: Artificial Sequence
<220> FEATURE:
<223> OTHER INFORMATION: Synthetic sequence

<400> SEQUENCE: 23

```
cccacggagg auccccaauc guggcguguc ggccucuccc aaucguggcg ugucggccuc     60

ucccaaucgu ggcgugucgg ccucucccaa ucguggcgug ucggccucuc uucggagagg    120

cacuggcgcc ggagaggcac uggcgccgga gaggcacugg cgccggagag gcacuggcgc    180
```

-continued cgggauccuc cguggg 196

<210> SEQ ID NO 24
<211> LENGTH: 1227
<212> TYPE: RNA
<213> ORGANISM: Artificial Sequence
<220> FEATURE:
<223> OTHER INFORMATION: Synthetic sequence

<400> SEQUENCE: 24
auggggaagg ugaaggucgg agucaacgga uuuggucgua uugggcgccu ggucaccagg 60
gcugcuuuua acucugguaa aguggauauu guugccauca augaccccuu cauugaccuc 120
aacuacaugg uuuacauguu ccaauaugau uccacccaug gcaaauucca uggcaccguc 180
aaggcugaga acgggaagcu ugucaucaau ggaaauccca ucaccaucuu ccaggagcga 240
gaucccucca aaaucaagug gggcgaugcu ggcgcugagu acgucgugga guccacuggc 300
gucuucacca ccauggagaa ggcuggggcu cauuugcagg ggggagccaa aagggucauc 360
aucucugccc ccucugcuga ugcccccaug uucgucaugg gugugaacca ugagaaguau 420
gacaacagcc ucaagaucau cagcaaugcc uccugcacca ccaacugcuu agcaccccug 480
gccaagguca uccaugacaa cuuugguauc guggaaggac ucaugaccac aguccaugcc 540
aucacugcca cccagaagac uguggauggc cccuccggga aacuguggcg ugauggccgc 600
ggggcucucc agaacaucau cccugccucu acuggcgcug ccaaggcugu gggcaagguc 660
aucccugagc ugaacgggaa gcucacuggc auggccuucc guguccccac ugccaacgug 720
ucaguggugg accugaccug ccgucuagaa aaaccugcca aauaugauga caucaagaag 780
guggugaagc aggcgucgga gggcccccuc aagggcaucc ugggcuacac ugagcaccag 840
guggucuccu cugacuucaa cagcgacacc cacuccucca ccuuugacgc uggggcuggc 900
auugcccuca acgaccacuu ugucaagcuc auuuccuggu augacaacga auuuggcuac 960
agcaacaggg ugguggaccu cauggcccac auggccucca aggaguaacu cgcuagagca 1020
ugguuaagcu ucccacggag gauccccaau cguggcgugu cggccucucc caaucguggc 1080
gugucggccu cucccaaucg uggcgugucg gccucuccca aucguggcgu gucggccucu 1140
cuucggagag gcacuggcgc cggagaggca cuggcgccgg agaggcacug gcgccggaga 1200
ggcacuggcg ccgggauccu ccguggg 1227

<210> SEQ ID NO 25
<211> LENGTH: 595
<212> TYPE: RNA
<213> ORGANISM: Artificial Sequence
<220> FEATURE:
<223> OTHER INFORMATION: Synthetic sequence

<400> SEQUENCE: 25
ugggaaauac acauuugcug cucacaugga uggaacauac aaauuuuguu uuaguaaccg 60
gauguccacc augacuccaa aaauagugau guucaccauu gauauugggg aggcuccaaa 120
aggacaagau auggaaacag aagcucacca gaacaagcua gaagaaauga ucaaugagcu 180
agcaguggcg augacagcug uaaagcacga acaggaauac auggaagucc gggagagaau 240
acacagagcc aucaacgaca acacaaacag cagaguggus cuuugguccu ucuuugaagc 300
ucuuguucua guugccauga cauugggaca gaucuacuac cugaagagau uuuuugaagu 360
ccggagaguu guuuaacucg cuagagcaug guuaagcuuc ccacggagga uccccaaucg 420

```
uggcgugucg gccucuccca aucguggcgu gucggccucu cccaaucgug gcgugucggc    480

cucucccaau cguggcgugu cggccucucu ucggagaggc acuggcgccg gagaggcacu    540

ggcgccggag aggcacuggc gccggagagg cacuggcgcc gggauccucc guggg         595


<210> SEQ ID NO 26
<211> LENGTH: 930
<212> TYPE: RNA
<213> ORGANISM: Artificial Sequence
<220> FEATURE:
<223> OTHER INFORMATION: Synthetic sequence

<400> SEQUENCE: 26

auggugagca agggcgagga ggauaacaug gccaucauca aggaguucau gcgcuucaag     60

gugcacaugg agggcuccgu gaacggccac gaguucgaga ucgagggcga gggcgagggc    120

cgccccuacg agggcaccca gaccgccaag cugaagguga ccaagggugg cccccugccc    180

uucgccuggg acauccuguc cccucaguuc auguacggcu ccaaggccua cgugaagcac    240

cccgccgaca uccccgacua cuugaagcug uccuuccccg agggcuucaa gugggagcgc    300

gugaugaacu ucgaggacgg cggcguggug accgugaccc aggacuccuc ccugcaggac    360

ggcgaguuca ucuacaaggu gaagcugcgc ggcaccaacu uccccuccga cggccccgua    420

augcagaaga agaccauggg cugggaggcc uccuccgagc ggauguaccc cgaggacggc    480

gcccugaagg gcgagaucaa gcagaggcug aagcugaagg acggcggcca cuacgacgcu    540

gaggucaaga ccaccuacaa ggccaagaag cccgugcagc ugcccggcgc cuacaacguc    600

aacaucaagu uggacaucac cucccacaac gaggacuaca ccaucgugga acaguacgaa    660

cgcgccgagg gccgccacuc caccggcggc auggacgagc uguacaagua acucgcuaga    720

gcaugguuaa gcuucccacg gaggaucccc aaucguggcg ugucggccuc ucccaaucgu    780

ggcgugucgg ccucucccaa ucguggcgug ucggccucuc ccaaucgugg cgugucggcc    840

ucucuucgga gaggcacugg cgccggagag gcacuggcgc cggagaggca cuggcgccgg    900

agaggcacug gcgccgggau ccuccguggg                                     930


<210> SEQ ID NO 27
<211> LENGTH: 935
<212> TYPE: RNA
<213> ORGANISM: Artificial Sequence
<220> FEATURE:
<223> OTHER INFORMATION: Synthetic sequence

<400> SEQUENCE: 27

augagcgagc ugauuaagga gaacaugcac augaagcugu acauggaggg caccguggac     60

aaccaucacu ucaagugcac auccgagggc gaaggcaagc ccuacgaggg cacccagacc    120

augagaauca agguggucga gggcggcccu cuccccuucg ccuucgacau ccuggcuacu    180

agcuuccucu acggcagcaa gaccuucauc aaccacaccc agggcauccc cgacuucuuc    240

aagcaguccu ucccugaggg cuucacaugg gagagaguca ccacauacga agacgggggc    300

gugcugaccg cuacccagga caccagccuc caggacggcu gccucaucua caacgucaag    360

aucagagggg ugaacuucac auccaacggc ccugugaugc agaagaaaac acucggcugg    420

gaggccuuca ccgagacgcu guaccccgcu gacggcggcc uggaaggcag aaacgacaug    480

gcccugaagc ucgugggcgg gagccaucug aucgcaaaca ucaagaccac auauagaucc    540

aagaaacccg cuaagaaccu caagaugccu ggcgucuacu auguggacua cagacuggaa    600

agaaucaagg aggccaacaa cgagaccuac gucgagcagc acgagguggc aguggccaga    660
```

-continued

```
uacugcgacc ucccuagcaa acuggggcac aagcucaauu aacacucgcu agagcauggu    720

ugguaccgua gucaagcuuc ccacggagga uccccaaucg uggcgugucg gccucuccca    780

aucguggcgu gucggccucu cccaaucgug gcgugucggc cucucccaau cguggcgugu    840

cggccucucu ucggagaggc acuggcgccg gagaggcacu ggcgccggag aggcacuggc    900

gccggagagg cacuggcgcc gggauccucc guggg                               935
```

```
<210> SEQ ID NO 28
<211> LENGTH: 142
<212> TYPE: RNA
<213> ORGANISM: Artificial Sequence
<220> FEATURE:
<223> OTHER INFORMATION: Synthetic sequence

<400> SEQUENCE: 28

gaaucugcaa guggauauug uuugagagcu aggccccaau cguggcgugu cggccugcuu     60

cggcaggcac uggcgccggg ccuagcaagu ucaaauaagg cuaguccguu aucaacuuga    120

aaaaguggca ccgagucggu gc                                             142
```

```
<210> SEQ ID NO 29
<211> LENGTH: 142
<212> TYPE: RNA
<213> ORGANISM: Artificial Sequence
<220> FEATURE:
<223> OTHER INFORMATION: Synthetic sequence

<400> SEQUENCE: 29

gaaucugcaa guggauauug uuugagagcu agaaauagca aguucaaaua aggcuagucc     60

guucucaacu uggccccaau cguggcgugu cggccugcuu cggcaggcac uggcgccggg    120

ccaaguggca ccgagucggu gc                                             142
```

```
<210> SEQ ID NO 30
<211> LENGTH: 189
<212> TYPE: RNA
<213> ORGANISM: Artificial Sequence
<220> FEATURE:
<223> OTHER INFORMATION: Synthetic sequence

<400> SEQUENCE: 30

gaaucugcaa guggauauug uuugagagcu aggccccaau cguggcgugu cggccugcuu     60

cggcaggcac uggcgccggg ccuagcaagu ucaaauaagg cuaguccguu cucaacuugg    120

ccccaaucgu ggcgugucgg ccugcuucgg caggcacugg cgccgggcca aguggcaccg    180

agucggugc                                                            189
```

```
<210> SEQ ID NO 31
<211> LENGTH: 214
<212> TYPE: RNA
<213> ORGANISM: Artificial Sequence
<220> FEATURE:
<223> OTHER INFORMATION: Synthetic sequence

<400> SEQUENCE: 31

ggggcccccc aaucguggcg ugucggccuc ucccaaucgu ggcgugucgg ccucucccaa     60

ucguggcgug ucggccucuc ccaaucgugg cgugucggcc ucucggccaa caugaggauc    120

acccaugucu gcagggccga gaggcacugg cgccggagag gcacuggcgc cggagaggca    180

cuggcgccgg agaggcacug gcgccggggg cccc                                214
```

<210> SEQ ID NO 32
<211> LENGTH: 51
<212> TYPE: DNA
<213> ORGANISM: Artificial Sequence
<220> FEATURE:
<223> OTHER INFORMATION: Synthetic sequence

<400> SEQUENCE: 32
gatcccgcga aattaatacg actcactata gggttgccat gtgtatgtgg g 51

<210> SEQ ID NO 33
<211> LENGTH: 31
<212> TYPE: DNA
<213> ORGANISM: Artificial Sequence
<220> FEATURE:
<223> OTHER INFORMATION: Synthetic sequence

<400> SEQUENCE: 33
caaggggtta tgctattgcc atgaatgatc c 31

<210> SEQ ID NO 34
<211> LENGTH: 37
<212> TYPE: DNA
<213> ORGANISM: Artificial Sequence
<220> FEATURE:
<223> OTHER INFORMATION: Synthetic sequence

<400> SEQUENCE: 34
tagcataacc ccttggggcc tctaaacggg tcttgag 37

<210> SEQ ID NO 35
<211> LENGTH: 39
<212> TYPE: DNA
<213> ORGANISM: Artificial Sequence
<220> FEATURE:
<223> OTHER INFORMATION: Synthetic sequence

<400> SEQUENCE: 35
atttcgcggg atcgagatct cgatcctcta cgccggacg 39

<210> SEQ ID NO 36
<211> LENGTH: 38
<212> TYPE: DNA
<213> ORGANISM: Artificial Sequence
<220> FEATURE:
<223> OTHER INFORMATION: Synthetic sequence

<400> SEQUENCE: 36
ggaatattaa gctcgccctt ttgccatgtg tatgtggg 38

<210> SEQ ID NO 37
<211> LENGTH: 37
<212> TYPE: DNA
<213> ORGANISM: Artificial Sequence
<220> FEATURE:
<223> OTHER INFORMATION: Synthetic sequence

<400> SEQUENCE: 37
tgacctcgaa gctcgccctt gttgccatga atgatcc 37

<210> SEQ ID NO 38
<211> LENGTH: 38
<212> TYPE: DNA
<213> ORGANISM: Artificial Sequence
<220> FEATURE:
<223> OTHER INFORMATION: Synthetic sequence

<400> SEQUENCE: 38
ggaaaggacg aaactctaga ttgccatgtg tatgtggg 38

<210> SEQ ID NO 39
<211> LENGTH: 44
<212> TYPE: DNA
<213> ORGANISM: Artificial Sequence
<220> FEATURE:
<223> OTHER INFORMATION: Synthetic sequence

<400> SEQUENCE: 39
tgtctcgagg tcgagaattc aaaaaaagtt gccatgaatg atcc 44

<210> SEQ ID NO 40
<211> LENGTH: 39
<212> TYPE: DNA
<213> ORGANISM: Artificial Sequence
<220> FEATURE:
<223> OTHER INFORMATION: Synthetic sequence

<400> SEQUENCE: 40
ggaaaggacg aaactctaga gcccggatag ctcagtcgg 39

<210> SEQ ID NO 41
<211> LENGTH: 78
<212> TYPE: DNA
<213> ORGANISM: Artificial Sequence
<220> FEATURE:
<223> OTHER INFORMATION: Synthetic sequenc

<400> SEQUENCE: 41
tgtctcgagg tcgagaattc aaaaaaatgg cgcccgaaca gggacttgcg agctcaggat 60
ccttccgttt cgcactgg 78

<210> SEQ ID NO 42
<211> LENGTH: 40
<212> TYPE: DNA
<213> ORGANISM: Artificial Sequence
<220> FEATURE:
<223> OTHER INFORMATION: Synthetic sequence

<400> SEQUENCE: 42
tagcgtttaa acttaagctt cccacggagg atccccaatc 40

<210> SEQ ID NO 43
<211> LENGTH: 41
<212> TYPE: DNA
<213> ORGANISM: Artificial Sequence
<220> FEATURE:
<223> OTHER INFORMATION: Synthetic sequence

<400> SEQUENCE: 43
acgggccctc tagactcgag cccacggagg atcccggcgc c 41

<210> SEQ ID NO 44
<211> LENGTH: 40
<212> TYPE: DNA
<213> ORGANISM: Artificial Sequence
<220> FEATURE:
<223> OTHER INFORMATION: Synthetic sequence

<400> SEQUENCE: 44
ggagacccaa gctggctagc atggggaagg tgaaggtcgg 40

-continued

<210> SEQ ID NO 45
<211> LENGTH: 59
<212> TYPE: DNA
<213> ORGANISM: Artificial Sequence
<220> FEATURE:
<223> OTHER INFORMATION: Synthetic sequence

<400> SEQUENCE: 45
ggatcctccg tgggaagctt aaccatgctc tagcgagtgt tactccttgg aggccatgt 59

<210> SEQ ID NO 46
<211> LENGTH: 40
<212> TYPE: DNA
<213> ORGANISM: Artificial Sequence
<220> FEATURE:
<223> OTHER INFORMATION: Synthetic sequence

<400> SEQUENCE: 46
ggagacccaa gctggctagc atggtgacgc ttgctgaact 40

<210> SEQ ID NO 47
<211> LENGTH: 58
<212> TYPE: DNA
<213> ORGANISM: Artificial Sequence
<220> FEATURE:
<223> OTHER INFORMATION: Synthetic sequence

<400> SEQUENCE: 47
ggatcctccg tgggaagctt aaccatgctc tagcgagtta aacaactctc cggacttc 58

<210> SEQ ID NO 48
<211> LENGTH: 42
<212> TYPE: DNA
<213> ORGANISM: Artificial Sequence
<220> FEATURE:
<223> OTHER INFORMATION: Synthetic sequence

<400> SEQUENCE: 48
ggagacccaa gctggctagc atggtgagca agggcgagga gg 42

<210> SEQ ID NO 49
<211> LENGTH: 58
<212> TYPE: DNA
<213> ORGANISM: Artificial Sequence
<220> FEATURE:
<223> OTHER INFORMATION: Synthetic sequence

<400> SEQUENCE: 49
ggatcctccg tgggaagcta accatgctct agcgagttac ttgtacagct cgtccatg 58

<210> SEQ ID NO 50
<211> LENGTH: 40
<212> TYPE: DNA
<213> ORGANISM: Artificial Sequence
<220> FEATURE:
<223> OTHER INFORMATION: Synthetic sequence

<400> SEQUENCE: 50
ggagacccaa gctggctagc atgagcgagc tgattaagga 40

<210> SEQ ID NO 51
<211> LENGTH: 65
<212> TYPE: DNA
<213> ORGANISM: Artificial Sequence
<220> FEATURE:
<223> OTHER INFORMATION: Synthetic sequence -continued

<400> SEQUENCE: 51
ggatcctccg tgggaagctt ctcccaaacc atgctctagc gagtgttaat tgagcttgtg 60
cccca 65

<210> SEQ ID NO 52
<211> LENGTH: 41
<212> TYPE: DNA
<213> ORGANISM: Artificial Sequence
<220> FEATURE:
<223> OTHER INFORMATION: Synthetic sequence

<400> SEQUENCE: 52
aaaggacgaa acaccgaatc tgcaagtgga tattgtttga g 41

<210> SEQ ID NO 53
<211> LENGTH: 33
<212> TYPE: DNA
<213> ORGANISM: Artificial Sequence
<220> FEATURE:
<223> OTHER INFORMATION: Synthetic sequence

<400> SEQUENCE: 53
tgatctagaa aaaaagcacc gactcggtgc cac 33

<210> SEQ ID NO 54
<211> LENGTH: 29
<212> TYPE: DNA
<213> ORGANISM: Artificial Sequence
<220> FEATURE:
<223> OTHER INFORMATION: Synthetic sequence

<400> SEQUENCE: 54 ttttttcta gatcataatc agccatacc 29

<210> SEQ ID NO 55
<211> LENGTH: 22
<212> TYPE: DNA
<213> ORGANISM: Artificial Sequence
<220> FEATURE:
<223> OTHER INFORMATION: Synthetic sequence

<400> SEQUENCE: 55
ggtgtttcgt cctttccaca ag 22

<210> SEQ ID NO 56
<211> LENGTH: 46
<212> TYPE: DNA
<213> ORGANISM: Artificial Sequence
<220> FEATURE:
<223> OTHER INFORMATION: Synthetic sequence

<400> SEQUENCE: 56
tagcgtttaa acttaagctt gtgcaggctg gcgccaccat ggcccc 46

<210> SEQ ID NO 57
<211> LENGTH: 43
<212> TYPE: DNA
<213> ORGANISM: Artificial Sequence
<220> FEATURE:
<223> OTHER INFORMATION: Synthetic sequence

<400> SEQUENCE: 57
acgggccctc tagactcgag ttacttgtac agctcgtcca tgc 43

<210> SEQ ID NO 58
<211> LENGTH: 38
<212> TYPE: DNA
<213> ORGANISM: Artificial Sequence
<220> FEATURE:
<223> OTHER INFORMATION: Synthetic sequence

<400> SEQUENCE: 58
ggaaaggacg aaactctaga ggggcccccc aatcgtgg 38

<210> SEQ ID NO 59
<211> LENGTH: 46
<212> TYPE: DNA
<213> ORGANISM: Artificial Sequence
<220> FEATURE:
<223> OTHER INFORMATION: Synthetic sequence

<400> SEQUENCE: 59
tgtctcgagg tcgagaattc aaaaaaaggg gcccccggcg ccagtg 46

<210> SEQ ID NO 60
<211> LENGTH: 49
<212> TYPE: DNA
<213> ORGANISM: Artificial Sequence
<220> FEATURE:
<223> OTHER INFORMATION: Synthetic sequence

<400> SEQUENCE: 60
gaaccgtcag atccgctagc caccatgggc tacccctacg acgtgcccg 49

<210> SEQ ID NO 61
<211> LENGTH: 23
<212> TYPE: DNA
<213> ORGANISM: Artificial Sequence
<220> FEATURE:
<223> OTHER INFORMATION: Synthetic sequence

<400> SEQUENCE: 61
tccagaatcc gcgtagatgc cgg 23

<210> SEQ ID NO 62
<211> LENGTH: 49
<212> TYPE: DNA
<213> ORGANISM: Artificial Sequence
<220> FEATURE:
<223> OTHER INFORMATION: Synthetic sequence

<400> SEQUENCE: 62
ctacgcggat tctggaggcg gtggatccat gagcgagctg attaaggag 49

<210> SEQ ID NO 63
<211> LENGTH: 28
<212> TYPE: DNA
<213> ORGANISM: Artificial Sequence
<220> FEATURE:
<223> OTHER INFORMATION: Synthetic sequence

<400> SEQUENCE: 63
agatctattg agcttgtgcc ccagtttg 28

<210> SEQ ID NO 64
<211> LENGTH: 37
<212> TYPE: DNA
<213> ORGANISM: Artificial Sequence
<220> FEATURE:
<223> OTHER INFORMATION: Synthetic sequence

<400> SEQUENCE: 64
caagctcaat agatctatgc ctgaaccggc aaaatcc 37

<210> SEQ ID NO 65
<211> LENGTH: 40
<212> TYPE: DNA
<213> ORGANISM: Artificial Sequence
<220> FEATURE:
<223> OTHER INFORMATION: Synthetic sequence

<400> SEQUENCE: 65
gactgcagaa ttcgaagctt acttggagct ggtgtacttg 40

<210> SEQ ID NO 66
<211> LENGTH: 53
<212> TYPE: DNA
<213> ORGANISM: Artificial Sequence
<220> FEATURE:
<223> OTHER INFORMATION: Combined DNA/RNA molecule

<400> SEQUENCE: 66
ggcccccaau cguggcgugu cggcctgctt cggcaggcac uggggccggg gcc 53

<210> SEQ ID NO 67
<211> LENGTH: 53
<212> TYPE: RNA
<213> ORGANISM: Artificial Sequence
<220> FEATURE:
<223> OTHER INFORMATION: Synthetic sequence Figure 5B

<400> SEQUENCE: 67
ggcccccaau cguggcgugu cggccugcuu cggcaggcac uggggccggg gcc 53

<210> SEQ ID NO 68
<211> LENGTH: 49
<212> TYPE: RNA
<213> ORGANISM: Artificial Sequence
<220> FEATURE:
<223> OTHER INFORMATION: Synthetic sequence Figure 10(1)

<400> SEQUENCE: 68
uccccaaucg uggcgugucg gccugcuucg gcaggcacug gggccggga 49

<210> SEQ ID NO 69
<211> LENGTH: 28
<212> TYPE: RNA
<213> ORGANISM: Artificial Sequence
<220> FEATURE:
<223> OTHER INFORMATION: Synthetic sequence Figure 10(2)

<400> SEQUENCE: 69
ggaagaaacu guggcacuuc ggugccag 28

<210> SEQ ID NO 70
<211> LENGTH: 20
<212> TYPE: RNA
<213> ORGANISM: Artificial Sequence
<220> FEATURE:
<223> OTHER INFORMATION: Synthetic sequence Figure 10(3)

<400> SEQUENCE: 70
agaagagcac guauacgcaa 20

<210> SEQ ID NO 71

-continued

<211> LENGTH: 32
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 71
nccaaucgug gcgugucgnn nacuggcgcc gn 32

<210> SEQ ID NO 72
<211> LENGTH: 32
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 72
ncaaaucgug gcgugucgnn nacuggcgcc gn 32

<210> SEQ ID NO 73
<211> LENGTH: 32
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 73
ncuaaucgug gcgugucgnn nacuggcgcc gn 32

<210> SEQ ID NO 74
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (32)..(32)
<223> OTHER INFORMATION: r encodes n, n are nucleotide fragments greater
      than or equal to 1 in length

<400> SEQUENCE: 74
rccaatcgtg gcgtgtcgrr ractggcgcc gn 32

<210> SEQ ID NO 75
<211> LENGTH: 52
<212> TYPE: RNA
<213> ORGANISM: Artificial Sequence
<220> FEATURE:
<223> OTHER INFORMATION: F30 scaffold RNA
<220> FEATURE:
<221> NAME/KEY: misc_structure
<222> LOCATION: (1)..(52)

<400> SEQUENCE: 75

-continued uugccaugug uauguggguu cgcccacaua cucugaugau cauucauggc aa 52

<210> SEQ ID NO 76
<211> LENGTH: 65
<212> TYPE: RNA
<213> ORGANISM: Artificial Sequence
<220> FEATURE:
<223> OTHER INFORMATION: tRNA scaffold RNA
<220> FEATURE:
<221> NAME/KEY: tRNA
<222> LOCATION: (1)..(65)

<400> SEQUENCE: 76
gcccggauag cucagucggu agagcagcgc gcggguccag gguucaaguc ccuguucggg 60
cgcca 65

<210> SEQ ID NO 77
<211> LENGTH: 49
<212> TYPE: RNA
<213> ORGANISM: Artificial Sequence
<220> FEATURE:
<223> OTHER INFORMATION: Pepper-2

<400> SEQUENCE: 77
cugccaaucg uggcgugucg gccugcuucg gcaggcacug gccaggccg 49

<210> SEQ ID NO 78
<211> LENGTH: 32
<212> TYPE: RNA
<213> ORGANISM: Artificial Sequence
<220> FEATURE:
<223> OTHER INFORMATION: Pepper (A4U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 78
nccuaucgug gcgugucgnn nacuggcgcc gn 32

<210> SEQ ID NO 79
<211> LENGTH: 32
<212> TYPE: RNA
<213> ORGANISM: Artificial Sequence
<220> FEATURE:
<223> OTHER INFORMATION: Pepper (A4G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 79
nccgaucgug gcgugucgnn nacuggcgcc gn 32

<210> SEQ ID NO 80
<211> LENGTH: 32
<212> TYPE: RNA
<213> ORGANISM: Artificial Sequence
<220> FEATURE:
<223> OTHER INFORMATION: Pepper (A4C)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 80
ncccaucgug gcgugucgnn nacuggcgcc gn 32

<210> SEQ ID NO 81
<211> LENGTH: 32
<212> TYPE: RNA
<213> ORGANISM: Artificial Sequence
<220> FEATURE:
<223> OTHER INFORMATION: Pepper (A5G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 81
nccagucgug gcgugucgnn nacuggcgcc gn 32

<210> SEQ ID NO 82
<211> LENGTH: 32
<212> TYPE: RNA
<213> ORGANISM: Artificial Sequence
<220> FEATURE:
<223> OTHER INFORMATION: Pepper (A5C)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 82
nccacucgug gcgugucgnn nacuggcgcc gn 32

<210> SEQ ID NO 83
<211> LENGTH: 32
<212> TYPE: RNA
<213> ORGANISM: Artificial Sequence
<220> FEATURE:
<223> OTHER INFORMATION: Pepper (U6A)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 83
nccaaacgug gcgugucgnn nacuggcgcc gn 32

<210> SEQ ID NO 84
<211> LENGTH: 32
<212> TYPE: RNA
<213> ORGANISM: Artificial Sequence
<220> FEATURE:
<223> OTHER INFORMATION: Pepper (U6G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 84
nccaagcgug gcgugucgnn nacuggcgcc gn 32

<210> SEQ ID NO 85
<211> LENGTH: 32
<212> TYPE: RNA
<213> ORGANISM: Artificial Sequence
<220> FEATURE:
<223> OTHER INFORMATION: Pepper (U6C)
<220> FEATURE:

```
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 85

nccaaccgug gcgugucgnn nacuggcgcc gn                              32


<210> SEQ ID NO 86
<211> LENGTH: 32
<212> TYPE: RNA
<213> ORGANISM: Artificial Sequence
<220> FEATURE:
<223> OTHER INFORMATION: Pepper (C7A)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 86

nccaauagug gcgugucgnn nacuggcgcc gn                              32


<210> SEQ ID NO 87
<211> LENGTH: 32
<212> TYPE: RNA
<213> ORGANISM: Artificial Sequence
<220> FEATURE:
<223> OTHER INFORMATION: Pepper (C7U)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 87

nccaauugug gcgugucgnn nacuggcgcc gn                              32


<210> SEQ ID NO 88
<211> LENGTH: 32
<212> TYPE: RNA
<213> ORGANISM: Artificial Sequence
<220> FEATURE:
<223> OTHER INFORMATION: Pepper (G8C)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 88

nccaauccug gcgugucgnn nacuggcgcc gn                              32


<210> SEQ ID NO 89
<211> LENGTH: 32
<212> TYPE: RNA
<213> ORGANISM: Artificial Sequence
<220> FEATURE:
<223> OTHER INFORMATION: Pepper (U9A)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 89

nccaaucgag gcgugucgnn nacuggcgcc gn                              32


<210> SEQ ID NO 90
```

```
<211> LENGTH: 32
<212> TYPE: RNA
<213> ORGANISM: Artificial Sequence
<220> FEATURE:
<223> OTHER INFORMATION: Pepper (G11A)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 90

nccaaucgug acgugucgnn nacuggcgcc gn                                  32


<210> SEQ ID NO 91
<211> LENGTH: 32
<212> TYPE: RNA
<213> ORGANISM: Artificial Sequence
<220> FEATURE:
<223> OTHER INFORMATION: Pepper (G11U)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 91

nccaaucgug ucgugucgnn nacuggcgcc gn                                  32


<210> SEQ ID NO 92
<211> LENGTH: 32
<212> TYPE: RNA
<213> ORGANISM: Artificial Sequence
<220> FEATURE:
<223> OTHER INFORMATION: Pepper (C12G)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 92

nccaaucgug gggugucgnn nacuggcgcc gn                                  32


<210> SEQ ID NO 93
<211> LENGTH: 32
<212> TYPE: RNA
<213> ORGANISM: Artificial Sequence
<220> FEATURE:
<223> OTHER INFORMATION: Pepper (C12A)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 93

nccaaucgug gagugucgnn nacuggcgcc gn                                  32


<210> SEQ ID NO 94
<211> LENGTH: 32
<212> TYPE: RNA
<213> ORGANISM: Artificial Sequence
<220> FEATURE:
<223> OTHER INFORMATION: Pepper (C12U)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length
```

<400> SEQUENCE: 94
nccaaucgug gugugucgnn nacuggcgcc gn 32

<210> SEQ ID NO 95
<211> LENGTH: 32
<212> TYPE: RNA
<213> ORGANISM: Artificial Sequence
<220> FEATURE:
<223> OTHER INFORMATION: Pepper (G13C)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 95
nccaaucgug gccugucgnn nacuggcgcc gn 32

<210> SEQ ID NO 96
<211> LENGTH: 32
<212> TYPE: RNA
<213> ORGANISM: Artificial Sequence
<220> FEATURE:
<223> OTHER INFORMATION: Pepper (U14A)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 96
nccaaucgug gcgagucgnn nacuggcgcc gn 32

<210> SEQ ID NO 97
<211> LENGTH: 32
<212> TYPE: RNA
<213> ORGANISM: Artificial Sequence
<220> FEATURE:
<223> OTHER INFORMATION: Pepper (U14G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 97
nccaaucgug gcgggucgnn nacuggcgcc gn 32

<210> SEQ ID NO 98
<211> LENGTH: 32
<212> TYPE: RNA
<213> ORGANISM: Artificial Sequence
<220> FEATURE:
<223> OTHER INFORMATION: Pepper (C17U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 98
nccaaucgug gcguguugnn nacuggcgcc gn 32

<210> SEQ ID NO 99
<211> LENGTH: 32
<212> TYPE: RNA
<213> ORGANISM: Artificial Sequence
<220> FEATURE:
<223> OTHER INFORMATION: Pepper (G18U)

<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 99
nccaaucgug gcgugucunn nacuggcgcc gn 32

<210> SEQ ID NO 100
<211> LENGTH: 32
<212> TYPE: RNA
<213> ORGANISM: Artificial Sequence
<220> FEATURE:
<223> OTHER INFORMATION: Pepper (G18C)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 100
nccaaucgug gcguguccnn nacuggcgcc gn 32

<210> SEQ ID NO 101
<211> LENGTH: 32
<212> TYPE: RNA
<213> ORGANISM: Artificial Sequence
<220> FEATURE:
<223> OTHER INFORMATION: Pepper (C27G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 101
nccaaucgug gcgugucgnn nacuggggcc gn 32

<210> SEQ ID NO 102
<211> LENGTH: 32
<212> TYPE: RNA
<213> ORGANISM: Artificial Sequence
<220> FEATURE:
<223> OTHER INFORMATION: Pepper (C27U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 102
nccaaucgug gcgugucgnn nacuggugcc gn 32

<210> SEQ ID NO 103
<211> LENGTH: 32
<212> TYPE: RNA
<213> ORGANISM: Artificial Sequence
<220> FEATURE:
<223> OTHER INFORMATION: Pepper (G28U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 103
nccaaucgug gcgugucgnn nacuggcucc gn 32

<210> SEQ ID NO 104
<211> LENGTH: 32
<212> TYPE: RNA
<213> ORGANISM: Artificial Sequence
<220> FEATURE:
<223> OTHER INFORMATION: Pepper (C29G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 104
nccaaucgug gcgugucgnn nacuggcggc gn 32

<210> SEQ ID NO 105
<211> LENGTH: 32
<212> TYPE: RNA
<213> ORGANISM: Artificial Sequence
<220> FEATURE:
<223> OTHER INFORMATION: Pepper (C29U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 105
nccaaucgug gcgugucgnn nacuggcguc gn 32

<210> SEQ ID NO 106
<211> LENGTH: 32
<212> TYPE: RNA
<213> ORGANISM: Artificial Sequence
<220> FEATURE:
<223> OTHER INFORMATION: Pepper (C30A)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 106
nccaaucgug gcgugucgnn nacuggcgca gn 32

<210> SEQ ID NO 107
<211> LENGTH: 32
<212> TYPE: RNA
<213> ORGANISM: Artificial Sequence
<220> FEATURE:
<223> OTHER INFORMATION: Pepper (C30U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 107
nccaaucgug gcgugucgnn nacuggcgcu gn 32

<210> SEQ ID NO 108
<211> LENGTH: 32
<212> TYPE: RNA
<213> ORGANISM: Artificial Sequence
<220> FEATURE:
<223> OTHER INFORMATION: Pepper (C2G/G31C)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 108
ngcaaucgug gcgugucgnn nacuggcgcc cn 32

<210> SEQ ID NO 109
<211> LENGTH: 32
<212> TYPE: RNA
<213> ORGANISM: Artificial Sequence
<220> FEATURE:
<223> OTHER INFORMATION: Pepper (C2U/G31A)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 109
nucaaucgug gcgugucgnn nacuggcgcc an 32

<210> SEQ ID NO 110
<211> LENGTH: 32
<212> TYPE: RNA
<213> ORGANISM: Artificial Sequence
<220> FEATURE:
<223> OTHER INFORMATION: Pepper (C2A/G31U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 110
nacaaucgug gcgugucgnn nacuggcgcc un 32

<210> SEQ ID NO 111
<211> LENGTH: 32
<212> TYPE: RNA
<213> ORGANISM: Artificial Sequence
<220> FEATURE:
<223> OTHER INFORMATION: Pepper (C10A/C30U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 111
nccaaucgua gcgugucgnn nacuggcgcu gn 32

<210> SEQ ID NO 112
<211> LENGTH: 32
<212> TYPE: RNA
<213> ORGANISM: Artificial Sequence
<220> FEATURE:
<223> OTHER INFORMATION: Pepper (C10C/C30G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 112
nccaaucguc gcgugucgnn nacuggcgcg gn 32

<210> SEQ ID NO 113
<211> LENGTH: 32
<212> TYPE: RNA
<213> ORGANISM: Artificial Sequence
<220> FEATURE:

```
<223> OTHER INFORMATION: Pepper (C10U/C30A)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 113

nccaaucguu gcgugucgnn nacuggcgca gn                              32


<210> SEQ ID NO 114
<211> LENGTH: 32
<212> TYPE: RNA
<213> ORGANISM: Artificial Sequence
<220> FEATURE:
<223> OTHER INFORMATION: Pepper (C2G/G31/C3A)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 114

ngaaaucgug gcgugucgnn nacuggcgcc cn                              32


<210> SEQ ID NO 115
<211> LENGTH: 32
<212> TYPE: RNA
<213> ORGANISM: Artificial Sequence
<220> FEATURE:
<223> OTHER INFORMATION: Pepper (C2G/G31C/A4C)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 115

ngccaucgug gcgugucgnn nacuggcgcc cn                              32


<210> SEQ ID NO 116
<211> LENGTH: 32
<212> TYPE: RNA
<213> ORGANISM: Artificial Sequence
<220> FEATURE:
<223> OTHER INFORMATION: Pepper (C2G/G31C/A5C)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 116

ngcacucgug gcgugucgnn nacuggcgcc cn                              32


<210> SEQ ID NO 117
<211> LENGTH: 32
<212> TYPE: RNA
<213> ORGANISM: Artificial Sequence
<220> FEATURE:
<223> OTHER INFORMATION: Pepper (C2G/G31C/G8C)
<220> FEATURE:
<221> NAME/KEY: misc_feature
<222> LOCATION: (1, 19, 20, 21, 32)
<223> OTHER INFORMATION: n are nucleotide fragments greater than or
      equal to 1 in length

<400> SEQUENCE: 117

ngcaauccug gcgugucgnn nacuggcgcc cn                              32
```

<210> SEQ ID NO 118
<211> LENGTH: 32
<212> TYPE: RNA
<213> ORGANISM: Artificial Sequence
<220> FEATURE:
<223> OTHER INFORMATION: Pepper (C2G/G31C/C12U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 118
ngcaaucgug gugugucgnn nacuggcgcc cn 32

<210> SEQ ID NO 119
<211> LENGTH: 32
<212> TYPE: RNA
<213> ORGANISM: Artificial Sequence
<220> FEATURE:
<223> OTHER INFORMATION: Pepper (C2G/G31C/U14G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 119
ngcaaucgug gcgggucgnn nacuggcgcc cn 32

<210> SEQ ID NO 120
<211> LENGTH: 32
<212> TYPE: RNA
<213> ORGANISM: Artificial Sequence
<220> FEATURE:
<223> OTHER INFORMATION: Pepper (C2G/G31C/C27U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 120
ngcaaucgug gcgugucgnn nacuggugcc cn 32

<210> SEQ ID NO 121
<211> LENGTH: 32
<212> TYPE: RNA
<213> ORGANISM: Artificial Sequence
<220> FEATURE:
<223> OTHER INFORMATION: Pepper (C2G/G31C/C29G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 121
ngcaaucgug gcgugucgnn nacuggcggc cn 32

<210> SEQ ID NO 122
<211> LENGTH: 32
<212> TYPE: RNA
<213> ORGANISM: Artificial Sequence
<220> FEATURE:
<223> OTHER INFORMATION: Pepper (C2G/G31C/C30U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 122
ngcaaucgug gcgugucgnn nacuggcgcu cn 32

<210> SEQ ID NO 123
<211> LENGTH: 32
<212> TYPE: RNA
<213> ORGANISM: Artificial Sequence
<220> FEATURE:
<223> OTHER INFORMATION: Pepper (C2G/G31C/G10A/C30U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 123
ngcaaucgua gcgugucgnn nacuggcgcu cn 32

<210> SEQ ID NO 124
<211> LENGTH: 32
<212> TYPE: RNA
<213> ORGANISM: Artificial Sequence
<220> FEATURE:
<223> OTHER INFORMATION: Pepper (C2G/G31C/G10C/C30G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 124
ngcaaucguc gcgugucgnn nacuggcgcg cn 32

<210> SEQ ID NO 125
<211> LENGTH: 32
<212> TYPE: RNA
<213> ORGANISM: Artificial Sequence
<220> FEATURE:
<223> OTHER INFORMATION: Pepper (C2G/G31C/G10U/C30A)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 125
ngcaaucguu gcgugucgnn nacuggcgca cn 32

<210> SEQ ID NO 126
<211> LENGTH: 32
<212> TYPE: RNA
<213> ORGANISM: Artificial Sequence
<220> FEATURE:
<223> OTHER INFORMATION: Pepper (C2U/G31A/G10C/C30G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 126
nucaaucguc gcgugucgnn nacuggcgcg an 32

<210> SEQ ID NO 127
<211> LENGTH: 32
<212> TYPE: RNA
<213> ORGANISM: Artificial Sequence
<220> FEATURE:
<223> OTHER INFORMATION: Pepper (C2U/G31A/G10U/C30A)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 127
nucaaucguu gcgugucgnn nacuggcgca an 32

<210> SEQ ID NO 128
<211> LENGTH: 32
<212> TYPE: RNA
<213> ORGANISM: Artificial Sequence
<220> FEATURE:
<223> OTHER INFORMATION: Pepper (C2A/G31U/G10A/C30U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 128
nacaaucgua gcgugucgnn nacuggcgcu un 32

<210> SEQ ID NO 129
<211> LENGTH: 32
<212> TYPE: RNA
<213> ORGANISM: Artificial Sequence
<220> FEATURE:
<223> OTHER INFORMATION: Pepper (C2A/G31U/G10C/C30G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 129
nacaaucguc gcgugucgnn nacuggcgcg un 32

<210> SEQ ID NO 130
<211> LENGTH: 32
<212> TYPE: RNA
<213> ORGANISM: Artificial Sequence
<220> FEATURE:
<223> OTHER INFORMATION: Pepper (C2A/G31U/G10U/C30A)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 130
nacaaucguu gcgugucgnn nacuggcgca un 32

<210> SEQ ID NO 131
<211> LENGTH: 32
<212> TYPE: RNA
<213> ORGANISM: Artificial Sequence
<220> FEATURE:
<223> OTHER INFORMATION: Pepper (C2G/G31C/G10C/C30G/C3A)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 131
ngaaaucguc gcgugucgnn nacuggcgcg cn 32

<210> SEQ ID NO 132
<211> LENGTH: 32
<212> TYPE: RNA
<213> ORGANISM: Artificial Sequence
<220> FEATURE:
<223> OTHER INFORMATION: Pepper (C2G/G31C/G10C/C30G/A4C)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 132
ngccaucguc gcgugucgnn nacuggcgcg cn 32

<210> SEQ ID NO 133
<211> LENGTH: 32
<212> TYPE: RNA
<213> ORGANISM: Artificial Sequence
<220> FEATURE:
<223> OTHER INFORMATION: Pepper (C2G/G31C/G10C/C30G/A5C)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 133
ngcacucguc gcgugucgnn nacuggcgcg cn 32

<210> SEQ ID NO 134
<211> LENGTH: 32
<212> TYPE: RNA
<213> ORGANISM: Artificial Sequence
<220> FEATURE:
<223> OTHER INFORMATION: Pepper (C2G/G31C/G10C/C30G/G8C)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 134
ngcaauccuc gcgugucgnn nacuggcgcg cn 32

<210> SEQ ID NO 135
<211> LENGTH: 32
<212> TYPE: RNA
<213> ORGANISM: Artificial Sequence
<220> FEATURE:
<223> OTHER INFORMATION: Pepper (C2G/G31C/G10C/C30G/C12U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 135
ngcaaucguc gugugucgnn nacuggcgcg cn 32

<210> SEQ ID NO 136
<211> LENGTH: 32
<212> TYPE: RNA
<213> ORGANISM: Artificial Sequence
<220> FEATURE:
<223> OTHER INFORMATION: Pepper (C2G/G31C/G10C/C30G/U14G)
<220> FEATURE:
<221> NAME/KEY: misc_feature
<222> LOCATION: (1, 19, 20, 21, 32)

<223> OTHER INFORMATION: n are nucleotide fragments greater than or equal to 1 in length

<400> SEQUENCE: 136
ngcaaucguc gcgggucgnn nacuggcgcg cn 32

<210> SEQ ID NO 137
<211> LENGTH: 32
<212> TYPE: RNA
<213> ORGANISM: Artificial Sequence
<220> FEATURE:
<223> OTHER INFORMATION: Pepper (C2G/G31C/G10C/C30G/C27U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 137
ngcaaucguc gcgggucgnn nacuggugcg cn 32

<210> SEQ ID NO 138
<211> LENGTH: 32
<212> TYPE: RNA
<213> ORGANISM: Artificial Sequence
<220> FEATURE:
<223> OTHER INFORMATION: Pepper (C2G/G31C/G10C/C30G/C29G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 138
ngcaaucguc gcgggucgnn nacuggcggg cn 32

<210> SEQ ID NO 139
<211> LENGTH: 32
<212> TYPE: RNA
<213> ORGANISM: Artificial Sequence
<220> FEATURE:
<223> OTHER INFORMATION: Pepper (C2G/G31C/G10C/C30G/C29G)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 139
ngcaaucguc gcgggucgnn nacuggcggg cn 32

<210> SEQ ID NO 140
<211> LENGTH: 32
<212> TYPE: RNA
<213> ORGANISM: Artificial Sequence
<220> FEATURE:
<223> OTHER INFORMATION: Pepper (C2G/G31C/G10A/C30U/U6G/C27U)
<220> FEATURE:
<221> NAME/KEY: misc_feature
<222> LOCATION: (1, 19, 20, 21, 32)
<223> OTHER INFORMATION: n are nucleotide fragments greater than or equal to 1 in length

<400> SEQUENCE: 140
ngcaagcgua gcgugucgnn nacuggugcu cn 32

<210> SEQ ID NO 141
<211> LENGTH: 32
<212> TYPE: RNA
<213> ORGANISM: Artificial Sequence
<220> FEATURE:
<223> OTHER INFORMATION: Pepper (C2G/G31C/G10C/C30G/U6G/C27U)
<220> FEATURE:
<221> NAME/KEY: misc_feature
<222> LOCATION: (1, 19, 20, 21, 32)
<223> OTHER INFORMATION: n are nucleotide fragments greater than or
equal to 1 in length

<400> SEQUENCE: 141
ngcaagcguc gcgugucgnn nacuggugcg cn 32

<210> SEQ ID NO 142
<211> LENGTH: 32
<212> TYPE: RNA
<213> ORGANISM: Artificial Sequence
<220> FEATURE:
<223> OTHER INFORMATION: Pepper (C2G/G31C/G10U/C30A/U9A/U14G/C27U)
<220> FEATURE:
<221> NAME/KEY: misc_feature
<222> LOCATION: (1, 19, 20, 21, 32)
<223> OTHER INFORMATION: n are nucleotide fragments greater than or
equal to 1 in length

<400> SEQUENCE: 142
ngcaaucgau gcgggucgnn nacuggugca cn 32

<210> SEQ ID NO 143
<211> LENGTH: 32
<212> TYPE: RNA
<213> ORGANISM: Artificial Sequence
<220> FEATURE:
<223> OTHER INFORMATION: Pepper (C2A/G31U/G10U/C30A/U9A/U14G/C27U)
<220> FEATURE:
<221> NAME/KEY: misc_feature
<222> LOCATION: (1, 19, 20, 21, 32)
<223> OTHER INFORMATION: n are nucleotide fragments greater than or
equal to 1 in length

<400> SEQUENCE: 143
nacaaucgau gcgggucgnn nacuggugca un 32